US009737075B2

(12) United States Patent
Benkovic et al.

(10) Patent No.: US 9,737,075 B2
(45) Date of Patent: Aug. 22, 2017

(54) SYNERGISTIC BENZOXABOROLE-CONTAINING ANTI-FUNGICIDAL COMPOSITION

(71) Applicants: Stephen Benkovic, State College, PA (US); Chunyu Liu, State College, PA (US)

(72) Inventors: Stephen Benkovic, State College, PA (US); Chunyu Liu, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 15/093,331

(22) Filed: Apr. 7, 2016

(65) Prior Publication Data

US 2016/0324160 A1 Nov. 10, 2016

Related U.S. Application Data

(60) Provisional application No. 62/145,179, filed on Apr. 9, 2015.

(51) Int. Cl.
*A01N 55/08* (2006.01)
*A01N 25/02* (2006.01)
*A01N 25/08* (2006.01)

(52) U.S. Cl.
CPC ............. *A01N 55/08* (2013.01); *A01N 25/02* (2013.01); *A01N 25/08* (2013.01)

(58) Field of Classification Search
CPC ........................................................ A01N 55/08
USPC ............................................................. 514/64
See application file for complete search history.

(56) References Cited

U.S. PATENT DOCUMENTS 3,873,279 A * 3/1975 Singer ........................ C02F 1/50 44/314
7,582,621 B2 * 9/2009 Baker ....................... C07F 5/02 514/64
7,767,657 B2 * 8/2010 Baker ...................... C07F 5/025 514/64
7,816,344 B2 * 10/2010 Baker .................... A61K 31/69 514/64
8,106,031 B2 * 1/2012 Lee ......................... C07F 5/025 514/64
8,115,026 B2 2/2012 Baker
8,168,614 B2 * 5/2012 Baker .................... A61K 31/69 514/64
8,669,207 B1 3/2014 Jacobson et al.
8,722,917 B2 5/2014 Baker
9,101,136 B2 8/2015 Satchivi
2011/0059985 A1 3/2011 Schmidts
2014/0259230 A1 9/2014 Bobbio

FOREIGN PATENT DOCUMENTS

WO WO 2014-173880 10/2014

OTHER PUBLICATIONS

Chou, *Pharmacol Rev* 58:621-681 (2006).
Odds, *J. Antimicrob. Chemother.* 52:1 (2003).
Liu, et al. (2014) *Bioorg. Med. Chem.* 22:4462-4473.
PCT/US2016/026451 International Search Report and Written Opinion.

* cited by examiner

*Primary Examiner* — Raymond Henley, III
(74) *Attorney, Agent, or Firm* — Husch Blackwell LLP

(57) ABSTRACT

An anti-fungal composition for the control of one or more target fungi (or a similar heterotrophic, hyphae-producing organism) that infect plant materials and are (is) separately controllable by a benzoxaborole and an anti-fungal compound of a preselected FRAC Target Site Code is disclosed, as is a method of its use. A composition contains a diluent medium having dissolved or dispersed therein a synergistic effective amount of each of a first and a second anti-fungal compound. The first anti-fungal compound is a benzoxaborole of Formula I. The second anti-fungal compound is other than a benzoxaborole and is known to control said one or more target species of fungus when utilized as the sole anti-fungal compound at a concentration greater than the synergistic effective amount and has a preselected FRAC Target Site Code of B, C, D, E, G, H, or M.

25 Claims, No Drawings

SYNERGISTIC BENZOXABOROLE-CONTAINING ANTI-FUNGICIDAL COMPOSITION

CROSS-REFERENCE TO RELATED APPLICATION

This application claims priority to U.S. application Ser. No. 62/145,179, filed on Apr. 9, 2015, whose disclosures are incorporated herein by reference.

TECHNICAL FIELD

The present invention contemplates a composition containing synergistic amounts of two anti-fungal agents, the first of which is a benzoxaborole compound and the second of which is other than a benzoxaborole compound, as well as a method for reducing the growth of one or more fungi by contacting the fungi with synergistic amounts of each of the above two anti-fungal agents.

BACKGROUND ART

Fungal infection of agricultural crops including cereals and grains, leaf crops and horticultural crops causes serious losses of value and nutrition around the world. Anti-fungal agents can be costly to purchase and use, and can be toxic or otherwise detrimental to some off-target animals and vegetation near to the site of application and in runoff affecting the watershed. It is therefore beneficial to farmers, consumers and their surrounding communities to use as little anti-fungal agent as possible, while continuing to control fungal growth to maximize crop yield. One way to to minimize the use of anti-fungal agents is to utilize anti-fungal compositions whose anti-fungal agents synergize with each other to provide an equal or better fungal control while using lessened amounts of anti-fungal agents used to accomplish that goal.

However, large-scale experimental drug combination studies have found that synergistic drug pairs are extremely complex and rare, with only a 4-10% probability of finding synergistic drug pairs [Yin et al., *PLOS* 9:e93960 (2014); Cokol et al., *Mol. Systems Biol.* 7:544 (2011)]. In fact, a systematic screening of about 120,000 two-component drug combinations based on reference-listed drugs found fewer than 10% synergistic pairs, as well as only 5% synergistic two-component pairs for fluconazole, a triazole anti-fungal compound similar to compounds in the FRAC Code G1, discussed below, that has the same mode of action [Borisy et al., *Proc. Natl Acad. Sci.* 100:7977-7982 (2003)].

Due to the complex nature of drug-drug interaction, synergy needs to be determined, not predicted. Determination of synergy can be efficiently performed through high throughput screening, but prediction of synergy is difficult. According to Dr. Chou, "If synergy is predictable, then there would be no need to conduct drug combination studies. Sometimes, the prediction might be correct by luck but it will not be quantitative. Frequently, predictions were done after the observed facts retrospectively, as can be seen in the biomedical literature" [Chou, *Cancer Res.* 70:440-446 (2010)].

A median-effect equation for a single drug effect has been extended to a multiple drug effect equation for n drugs. The equation provides the theoretical basis for the fractional inhibitory concentration index (FICI) isobologram equation that permits quantitative determination of drug interactions, where FICI <1, =1, and >1 indicate synergism, additive effect, and antagonism, respectively. Based on these algorithms, computer software has been developed to permit automated determination of synergism and antagonism at all dose or effect levels.

Such data analyses have facilitated dose-effect analysis for single drug evaluation or carcinogen and radiation risk assessment, as well as for drug or other entity combinations in a vast field of disciplines of biomedical and agricultural sciences. The merging of the mass-action law principle with mathematical induction-deduction has been shown to be a unique and effective scientific method for general theory development. Chou, *Pharmacol Rev* 58:621-681 (2006).

One of the major objectives of having a synergistic drug combination is to reduce the dose of the drug used, thereby reducing the toxicity while maintaining efficacy. The concept of the dose-reduction index [DRI] was formally introduced by Chou and co-workers in 1988 [Chou et al., *Pharmacologist* 30:A231 (1988)] and has since been used in many publications. The DRI is a measure of how many-fold the dose of each drug in a synergistic combination can be reduced at a given effect level compared with the doses of each drug alone.

Chou and Talalay in 1983 [Chou et al., *Trends Pharmacol* 4:450-454 (1983)] used the term combination index (CI, now often referred to as FICI or fractional inhibitory concentration index) for quantification of synergism or antagonism for two drugs where FICI <1, =1, and >1, indicate synergism, additive effect, and antagonism, respectively. The equation for determining FICI is shown below, where $D_1$ and $D_2$ are the two doses of active agents. In the denominator, $(D_x)_1$ is for $D_1$ $$FICI = \frac{(D)_1}{(D_x)_1} + \frac{(D)_2}{(D_x)_2}$$

"alone" that inhibits a system x %, and $(D_x)_2$ is for $D_2$ "alone" that inhibits a system x %. The $(D_x)_1$ and $(D_x)_2$ values can be calculated as discussed in Chou, *Pharmacol Rev* 58:621-681 (2006). In the numerators, $(D)_1+(D)_2$ "in combination" also inhibit x %. If the sum of these two fractional terms is equal to 1, additive action is indicated. If the FICI value is smaller than 1, synergism is indicated, and if the FICI value is greater than 1, antagonism is indicated.

The dose reduction index (DRI) is obtained by inverting each term of the above equation. Thus, for a two drug combination:

$$FICI = \frac{(D)_1}{(D_x)_1} + \frac{(D)_2}{(D_x)_2} = \frac{1}{(DRI)_1} + \frac{1}{(DRI)_2}$$

Although DRI >1 is beneficial, it does not necessarily indicate synergism because, from the above equation, an additive effect or even slight antagonism can also lead to DRI >1. As noted in Chou, *Pharmacol Rev* 58:621-681 (2006), Table 4 on page 637, numerical values for FICI have been developed that are indicative of synergy, additivity or antagonism. The values shown in that table are set out below. Computer software developed

| Range of FICI | Description |
|---|---|
| <0.1 | Very strong synergism |
| 0.1-0.3 | Strong synergism |
| 0.3-0.7 | Synergism |
| 0.7-0.85 | Moderate synergism |
| 0.85-0.90 | Slight synergism |
| 0.90-1.10 | Nearly additive |
| 1.10-1.20 | Slight Antagonism |
| 1.20-1.45 | Moderate Antagonism |
| 1.45-3.3 | Antagonism |
| 3.3-10 | Strong antagonism |
| >10 | Very strong antagonism |

by Chou and co-workers is also available commercially from ComboSyn, Inc. of Paramus, N.J., for use in calculating the CI and DRI values.

The designations based on FICI values of Chou's Table 4, above, notwithstanding, others have taken a more conservative approach to use of such values to assert the presence of synergy. Thus, the article of Odds [*J. Antimicrob. Chemother.* 52:1 (2003)] notes that for several reasons, that journal will require authors submitting papers containing FICI data to use the interpretations of 'synergy' (FICI ≤0.5), 'antagonism' (FICI >4.0) and 'no interaction' (FICI >0.5-4.0). That usage was said to also foster conservative interpretations of the data, in that some combinations of agents can exert inhibitory effects that are more than the sum of their effects alone (FICI <1.0) or less than their effects alone (FICI >1.0). Comparatively, the more conservative approach excludes the "Moderate synergism" and "Slight synergism" taught in Chou, *Pharmacol Rev* 58:621-681 (2006). The publication by Barbee et al. [*Antimicrob. Agents Chemother.*, 69:1572-1578 (2014)] utilizes that measure.

Fungal infections of substrates such as plants, animals, food stuffs and drinks such as wine and beer can have both positive and negative financial, health and other effects upon society, depending on what it is that is infected. Several anti-fungal compounds have been developed and approved for use on those infected substrates where such an infection can have a detrimental effect.

Anti-fungal agents have been found to act by one or more mechanisms and are frequently grouped or classed by the mechanism of action by which the agent kills fungi or inhibits fungal growth. One classification system used widely in the industry is that of FRAC, the Fungicide Resistance Action Committee, which is a specialist technical group of Crop Life International (CLI). CLI is itself a global network of companies and associations that deal in plant biotechnology and crop protection.

The Fungicide Resistance Action Committee (FRAC) is an international organization made up of representatives of the agrochemical industry whose mission is to provide fungicide resistance management guidelines to prolong the effectiveness of fungicides and to limit crop losses should resistance occur. FRAC publishes a Code List (version updated on February 2015) of different letters (A to I, with added numbers) that are used to distinguish fungicide compositions according to their biochemical mode of action (MOA) in fungal plant pathogens. The grouping was made according to processes in metabolism ranging from nucleic acid synthesis (A) to secondary metabolism, e.g. melanin synthesis (I) at the end of the list, followed by host plant defense inducers (P), recent molecules with an unknown mode of action and unknown resistance risk (U, transient status, mostly not longer than 8 years, until information about mode of action and mechanism of resistance becomes available), and multi-site inhibitors (M).

Within a given mode of action such as "nucleic acid synthesis" inhibitors, the FRAC code also lists a target site and code such as "A1: RNA polymerase I", "A2: adenosine deaminase", "A3: DNA/RNA synthesis", etc. A group name is also provided for each code number such as "fungicides" for A1, and the groups can be sub-divided by "chemical group", which for A1 are three: "acylalanines", "oxazolidinones" and "butyrolactones". The common names of various commercially available antifungal compounds in each chemical group are also provided. A FRAC Code number is also provided for each target site and letter-number code, although the FRAC code "number" and the letter-number code for the P group and the M group are each the same letter-number codes.

According to *FRAC recommendations for fungicide mixtures designed to delay resistance evolution*, FRAC, page 2, January 2010, fungicides are often combined as co-formulations or tank mixes for several reasons that can be conveniently divided into three categories:

1. Improved disease control. Mixtures can be used to broaden the spectrum of disease control of a product.

2. Disease control security when resistance is present.

3. Resistance management. When used for resistance management it is necessary for at least two components of the mixture to have activity against the field populations of the target pathogen when used alone. Note that none of these address synergism, which is not understood to be a commonly applied criterion in the use of anti-fungals to control plant pathogens.

Although the FRAC code identifiers were originally intended for use in minimizing crop resistance to fungicides by their mode of action (MOA), the FRAC codes and the fungicides associated with those codes have other uses as are discussed hereinafter. The fungal species and/or strain that can be controlled (whose growth can be inhibited or stopped) by a particular fungicide is known in the art from the product label, licensing by governmental agencies such as the Environmental Protection Agency (EPA) in the United States, and the Pest Management Regulatory Agency (PMRA) in Canada, as well as by literature reports, and can be correlated back to the MOA of that fungicide and thereby to a FRAC code.

Anti-fungal agents are or can be looked upon as pharmaceutical products. Such agents can cause harmful side effects if used on one substrate and then ingested or contacted with the skin or eyes of an animal such as a human.

Captan, a phthalimide with a FRAC code of M4, is among the largest selling fungicides, and is reported to be relatively non-toxic to humans and birds, but is toxic to fish. Captan has been found to cause cancer in male and female mice at high doses and is chemically similar to pesticides that have been shown to cause cancer.

Triazoles, with a FRAC Code of G1, and strobilurins, with a FRAC Code of C3, inhibit C14-demethylase in sterol biosynthesis and cytochrome bc1, respectively, account for about 35 percent of the 8.9 billion dollar fungicide market as of 2005. These compounds are typically sprayed on to crops. Each of those chemical groups encompasses several different fungicides. Fishel, [*Document PI*-68, Agronomy Department, UF/IFAS Extension, original publication September 2005, revised March 2014] reported that the triazoles are relatively non-toxic orally to mammals, but some are listed as possible human carcinogens. Like captan, the triazoles as a group are generally not toxic to birds nor to bees, but are moderately to highly toxic to fish. A study of three widely-used strobilurins indicated potential toxic effects on the early development of grass carp. [Liu et al., *Ecotoxica Environ Saf* 98:297-302 (December 2013).]

Benzoxyborole preparations and uses are the subject of several US patents, including U.S. Pat. No. 7,582,621; U.S. Pat. No. 7,767,657; U.S. Pat. No. 7,816,344; and U.S. Pat. No. 8,168,614. Many of the uses of those compounds are as antibiotics, with U.S. Pat. No. 7,816,344 teaching at column 1, lines 37-41, certain classes of oxaboroles of Formula A that are monosubstituted at the -3, 6- or

A

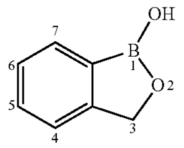

-7 position or disubstituted at the 3-/6-, or -3/-7 positions are surprisingly effective antibacterials.

U.S. Pat. No. 7,767,657 teaches and claims that a 5-fluorobenzoxyborole of Formula B and its salts

B

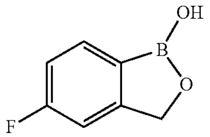

are useful in a composition for topical or foliar administration to an animal suffering from an infection from a microorganism, and particularly exemplifies yeasts and molds as the microorganism treated.

US Patent Publication No. 20140259230 published Sep. 11, 2014 teaches the use of several oxaborole compounds for protecting plants and plant propagation materials from phytopathogens. One group of oxaboroles were disclosed to be those of Formula B-1

B-1

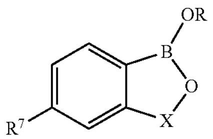

in which the possible combinations of R, $R^7$ and X amount to more than 100 million compounds. Those substituents in a further preferred embodiment were F for $R^7$, $CH_2$ for X and R was H, $C_1$-$C_4$alkyl optionally substituted by —$NR^3R^4$ wherein $R^3$ and $R^4$ are each independently hydrogen, optionally substituted $C_1$-$C_4$alkyl. A composition containing a compound of Formula B-1 was said to be useful in a method of protecting plants or plant propagation materials against phytopathogenic fungi belonging to several classes. The above published application teaches the use of several oxaboroles at concentrations ranging from 200 to 20 parts per million (ppm) to obtain between 80 and 20 percent control of fungal growth on infected plants, seeds and plant propagation materials.

Benzoxaboroles of Formula B-1 are known to inhibit aminoacyl tRNA synthetases, which are a family of enzymes responsible for attaching specific amino acids to the appropriate tRNAs. The ribosome then transfers the amino acids from the tRNAs onto the protein being synthesized. Benzoxaboroles selectively target the editing domain of the enzyme, leading to mis-incorporation of amino acids into proteins and subsequent failure of normal protein production needed for cell survival [Liu, et al. (2014) *Bioorg. Med. Chem.* 22:4462-4473].

Although benzoxaboroles have been known to be general anti-microbial agents by disrupting the target organism's DNA translation processes, not much is known regarding how disruption of DNA translation might affect other biological systems within the same organism. More specifically, it is not known how the disruption of DNA translation by benzoxaboroles might affect the target organism's sensitivity to other anti-microbial chemicals that disrupt biological processes other than those mediated by Leucyl-tRNA synthetase. If benzoxaborole and another non-benzoxaborole compound can separately disrupt two or more distinct biological processes, they can have an effect greater than the sum of that induced in separate treatments of the target organism. Thus, identifying synergistic combinations is an important strategy for obtaining effective biological controls.

Synergism can potentially also work by cooperativity if two anti-microbial compounds affect each other's binding at different sites on the same molecule. Such cooperativity occurs naturally in biological systems and has powerful effects on e.g. ligand-gated ion channels and the function of hemoglobin in gas exchange, yet the complexity of protein structure makes cooperative and allosteric effects extremely difficult to predict. Cooperative interactions of multiple distinct drugs binding to different sites on the same target molecule are known [Hartman et al., *Biochem Pharmacol.* 97(3):341-349 (Oct. 1, 2015)] but are apparently not common or expected.

In view of the ancillary toxicity and potential carcinogenicity exhibited by fungicides along with the beneficial crop-saving and disease fighting attributes of the same materials, it would be advantageous if the potential for the detrimental side effects of fungicidal use could be minimized, while maintaining high anti-fungal activity and use of less of those compounds. The present invention that is described hereinafter provides one means for maintaining or enhancing benefits and minimizing detriments of the use of particular fungicidal groups with specific fungi.

BRIEF SUMMARY OF THE INVENTION

The present invention contemplates an anti-fungal composition for the control of one or more target fungi (or a similar heterotrophic, hyphae-producing organism) that infect plant materials and are (is) separately controllable by a benzoxaborole and an anti-fungal compound of a preselected biochemical mode of action (MOA) as described by a FRAC Target Site Code. The composition comprises an agriculturally acceptable diluent medium having dissolved or dispersed therein a synergistic effective amount of each of a first and a second anti-fungal compound.

The first anti-fungal compound is a benzoxaborole of Formula I, below, where X is a

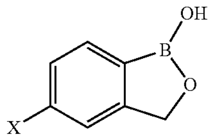

I substituent having a Hammett sigma value for a meta substituent that is greater (more positive) than about −0.1, and more preferably a H, $C_1$-$C_6$ hydrocarbyl or halo group. The second anti-fungal compound is other than a benzoxaborole and is known to control the one or more target species of fungus when utilized as the sole anti-fungal compound at a concentration greater than the synergistic effective amount. That second anti-fungal agent has a FRAC Target Site Code selected from one or more of a FRAC group consisting of B, C, D, E, G, H, and M. More preferably, the second anti-fungal agent has a FRAC Target Site Code selected from one or more of a FRAC group consisting of of B1, B3, C3, C4, C6, D1, E1, E2, E3, G1, H5, M4, and M3.

A concentrate anti-fungal composition in which the anti-fungal agents are present dissolved or dispersed in a diluent medium that can be the same or different from that recited above is also contemplated. The antifungal agents are preferably present in that concentrate anti-fungal composition in the same proportion that they are present in the anti-fungal composition so that the anti-fungal composition can be prepared by dilution of the concentrate with an appropriate diluent such as water.

A method of reducing growth of a target fungus is also contemplated. In accordance with that method, a target fungus is contacted with a synergistic amount of the above first and second anti-fungal agents (compounds), and that contact is maintained for a period of time sufficient to inhibit growth of the target fungus. Preferably, that contact is carried out by administering an above composition to the target fungus where the administration is topical, soil, foliar or systemic. In some embodiments, the administration of the synergistic amounts of the two anti-fungal agents is repeated.

DEFINITIONS

As used herein, the term "hydrocarbyl" is a short hand term for a non-aromatic group that includes straight and branched chain aliphatic as well as alicyclic groups or radicals that contain only carbon and hydrogen. Inasmuch as alicyclic groups are cyclic aliphatic groups, such substituents are deemed to be subsumed within the aliphatic groups. Thus, alkyl, alkenyl and alkynyl groups are contemplated.

Exemplary hydrocarbyl groups contain a chain of 1 to about 6 carbon atoms, and more preferably 1 to 4 carbon atoms. Examples of hydrocarbyl radicals include methyl, ethyl, n-propyl, isopropyl, n-butyl, isobutyl, sec-butyl, tert-butyl, pentyl, iso-amyl, hexyl, and the like. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl and the like. Examples of alkynyl radicals include ethynyl, 2-propynyl, 3-propynyl, decynyl, 1-butynyl, 2-butynyl, 3-butynyl, and the like.

An alkyl group is a preferred hydrocarbyl group. As a consequence, a generalized, but more preferred substituent can be recited by replacing the descriptor "hydrocarbyl" with "alkyl" in any of the substituent groups enumerated herein. Where a specific aliphatic hydrocarbyl substituent group is intended, that group is recited; i.e., $C_1$-$C_4$ alkyl, methyl or dodecenyl.

A contemplated cyclohydrocarbyl substituent ring contains 3 to 6 carbon atoms. The term "cycloalkylalkyl" means an alkyl radical as defined above that is substituted by a cycloalkyl radical. Examples of such cycloalkyl radicals include cyclopropyl, cyclobutyl, cyclopentyl, cyclohexyl and the like.

Usual chemical suffix nomenclature is followed when using the word "hydrocarbyl" except that the usual practice of removing the terminal "yl" and adding an appropriate suffix is not always followed because of the possible similarity of a resulting name to that of one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, and cyclohexenyloxy groups. On the other hand, a hydrocarbyl group containing a —C(O)— functionality is referred to as a hydrocarboyl (acyl) and that containing a —C(O)O— is a hydrocarboyloxy group inasmuch as there is no ambiguity. Exemplary hydrocarboyl and hydrocarboyloxy groups include acyl and acyloxy groups, respectively, such as formyl, acetyl, propionyl, butyryl, valeryl, 4-methylvaleryl, and acetoxy, acryloyl and acryloyloxy.

The term "halogen" or "halo" means fluoride, chloride, bromide or iodide. The term "halohydrocarbyl" means a hydrocarbyl radical as defined above wherein one or more hydrogens is replaced with a halogen. A halohydrocarbyl radical (group or substituent) is typically a substituted alkyl substituent. Examples of such haloalkyl radicals include chloromethyl, 1-bromoethyl, fluoromethyl, difluoromethyl, trifluoromethyl, 1,1,1-trifluoroethyl and the like.

The term "perfluorohydrocarbyl" means an alkyl group wherein each hydrogen has been replaced by a fluorine atom. Examples of such perfluorohydrocarbyl groups, in addition to trifluoromethyl above, are perfluorobutyl, perfluoroisopropyl, and perfluorohexyl.

The phrase "True Fungi" is used herein for all of the organisms discussed herein except for the Oomycota (*Phytophthora infestens* and *Plasmopara viticola*). The uncapitalized term "fungi" or "fungus" is used to include all of the organisms discussed herein, including the Oomycota.

The present invention has several benefits and advantages.

One benefit is that the user can achieve a similar amount of fungal growth inhibition using less anti-fungal compounds than previously used.

An advantage of the invention is that there is less danger to aquatic life or less toxic environmental impact with which a contemplated composition may come into contact because of the lessened concentration of the second anti-fungal agent present in a composition.

Another benefit is that a contemplated benzoxaborole is generally non-toxic to humans or other mammals or to aquatic life with which it may come into contact.

Another advantage is that a contemplated benzoxaborole is typically less expensive than the second anti-fungal compound with which it is used so that the cost outlay to produce a given amount of fungal growth inhibition should be reduced.

Still further benefits and advantages of the invention will be apparent to those skilled in the art from the discussion that follows.

DETAILED DESCRIPTION OF THE INVENTION

The present invention contemplates an anti-fungal composition for the control of one or more target fungi (or a similar heterotrophic, hypha-producing organism) that is(are) controllable by an anti-fungal compound of a preselected MOA as described by a FRAC Target Site Code. The composition comprises a diluent medium in which is dissolved or dispersed a synergistic effective amount of each of a first and a second anti-fungal compound. The first anti-fungal compound is a benzoxaborole of Formula I, below. The second anti-fungal compound is other than a benzoxaborole and is known to control the one or more target species of fungus when utilized as the sole anti-fungal compound at a concentration greater than the synergistic effective amount. That second anti-fungal agent (compound) has a FRAC Target Site Code selected from one or more of a FRAC group consisting of B, C, D, E, G, H, and M. More preferably, the second anti-fungal agent (compound) has a FRAC Target Site Code selected from one or more of a FRAC group consisting of of B1, B3, C3, C4, C6, D1, E1, E2, E3, G1, H5, M4 and M5,

I

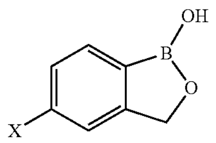

where X is a substituent having a Hammett sigma value for a meta substituent that is greater (more positive) than about −0.1, and more preferably H, $C_1$-$C_6$ hydrocarbyl or halo group. Hammett sigma functions are well known to workers skilled in organic chemistry and lists of those values for meta and para substituents are published in many texts. See, for example, Hine, *Physical Organic Chemistry,* 2$^{nd}$ ed, McGraw-Hill book Co., Inc., New York, page 87 (1962). Illustrative Hammett sigma values for meta substituents are provided in the Table below.

HAMMETT SIGMAS VALUES FOR META SUBSTITUENTS*

| Substituent | Sigma $(\sigma)_{meta}$ value |
|---|---|
| —NH2 | −0.16 |
| —$C(CH_3)_3$ | −0.1 |
| —$CH_3$ | −0.07 |
| —$C_2H_5$ | −0.07 |
| —H | 0.00 |
| —$OCH_3$ | +0.12 |
| —$NHCOCH_3$ | +0.21 |
| —$CO_2CH_3$ | +0.32 |
| —F | +0.34 |
| —Cl | +0.37 |
| —$C(O)CH_3$ | +0.38 |
| —Br | +0.39 |
| —$CF_3$ | +0.43 |
| —CN | +0.56 |

*Values from Hine, above.

Turning first to the anti-fungal compounds, each of the first and the second active ingredient compounds is a known anti-fungal agent in its own right. A contemplated benzoxaborole of Formula I, where X is a substituent having a Hammett sigma value for a meta substituent that is greater (more positive) than about −0.1, preferably that value is zero or greater. More preferably, X is a H, $C_1$-$C_6$ hydrocarbyl, Cl or F group. These compounds are disclosed and claimed in U.S. Pat. No. 5,880,188 as an antimicrobial agent. The compound in which the benzoxaborole of Formula I where X is F is taught to be useful as an anti-fungal agent in U.S. Pat. No. 7,582,621 and in a pharmaceutical formulation with a pharmaceutically acceptable excipient for topical administration to an animal suffering from a microbial infection.

As will be seen from the data in Table 1 hereinafter, the fungal growth inhibition obtained using a benzoxaborole of Formula I where X was fluorine (F) or chlorine (Cl) was better than that obtained using hydrogen (H) or methyl ($CH_3$), an example of a $C_1$-$C_6$ hydrocarbyl group. Compounds where X was hydrogen and methyl provided very similar results. All of those inhibition results were better than those obtained using a benzoxaborole of Formula I where X was amino (—$NH_2$). As a result, further assays were carried out with a benzoxaborole of Formula I where X was fluorine (F), chlorine (Cl) or hydrogen (H). Structural formulas of those four compounds where where X was fluorine, chlorine, hydrogen and methyl are illustrated below along with their identifying abbreviations.

BO

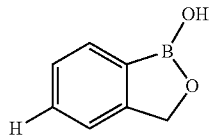

B90

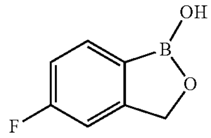

B18

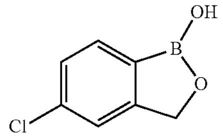

B1

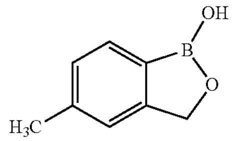

The second anti-fungal compound that is other than a benzoxaborole and is known to control the one or more target species of fungus when utilized as the sole anti-fungal compound at a concentration greater than the synergistic effective amount is also a known material. The specific second anti-fungal compound of a contemplated composition is typically selected for its known activity against one or more species or strains of fungus as evidenced by the FRAC Target Site Code for that compound.

A second compound contemplated for use herein is classified in a FRAC Target Site Code that is selected from one or more of a FRAC group consisting of B, C, D, E, G, H, and M. More preferably, a FRAC Target Site Code is selected from one or more of a FRAC group consisting of B1, B3, C3, C4, C6, D1, E1, E2, E3, G1, H5, M4 and M5. The FRAC Target Site Code single number designations are 1, 22, 11, 21, 30, 9, 13, 12, 2, 3, 40, M4, and M5, respectively. A table of FRAC target site and code, the numerical code for the target site and code, and the Mode of Action is provided below.

A second compound contemplated for use herein (in a synergistic composition with a benzoxaborole) is one or more of a compound selected from the list of: carbendazim, thiabendazole, thiophanate, thiophanate-methyl, diethofencarb, zoxamide, ethaboxam, pencycuron, flupicolide, flutolanil, fluopyram, fluxapyroxad, penthiopyrad, benodanil, mepronil, isofetamid, fenfuram, carboxin, oxycarboxin, thifluzamide, benzovindiflupyr, bixafen, furametpyr, isopyrazam, penflufen, sedaxane, boscalid, benomyl, fuberidazole, diflumetorim, tolfenpyrad, azoxystrobin, coumoxystrobin, enoxastrobin, flufenoxystrobin, picoxystrobin, pyraoxystrobin, mandestrobin, pyraclostrobin, pyrametostrobin, triclopyricarb, kresoxim-methyl, trifloxystrobin, dimeoxystrobin, fenamistrobin, methominostrobin, orysastrobin, famoxadone, fluoxastrobin, fenamidone, pyribencarb, cyazofamid, amisulbrom, binapacryl, meptyldinocap, dinocap, fluazinam, fentin chloride, fentin acetate, fentin hydroxide, silthiofam, ametoctradin, cyprodinil, mepanipyrim, pyrimethanil, kasugamycin, quinoxyfen, proquinazid, fenpiclonil, fludioxonil, chlozolinate, dimethachlone, iprodione, procymidone, vinclozolin, triforine, pyrifenox, pyrisoxazole, fenarimol, nuarimol, imazalil, oxpoconazole, pefurazoate, prochloraz, triflumizole, azaconazole, bitertanol, bromuconazole, cyproconazole, diniconazole, epoxiconazole, etanconazole, fenbuconazole, fluquinconazole, flusilazole, flutriafol, hexaconazole, imibenconazole, ipconazole, metconazole, myclobutanil, penconazole, propiconazole, simeconazole, tebuconazole, tetraconazole, triadimefon, triadimenol, triticonazole, prothioconazole, aldimorph, dodemorph, fenpropimorph, tridemorph, fenpropidin, piperalin, spiroxamine, fenhexamid, fenpyrazamine, pyributicarb, naftifine, terbinafine, validamycin, polyoxin, dimethomorph, flumorph, pyrimorph, benthiavalicarb, iprovalicarb, valifenalate, mandipropamid, ferbam, macozeb, maneb, metiram, propineb, thiram, zineb, ziram, captan, captafol, folpet, dichlofluanid, tolylfluanid, or chlorothalonil. More preferably, a second anti-fungal compound in composition with a benzoxabrole is selected from the list of: carbendazim, thiabendazole, thiophanate, thiophanate-methyl, zoxamide, ethaboxam, benomyl, fuberidazole, azoxystrobin, coumoxystrobin, enoxastrobin, flufenoxystrobin, picoxystrobin, pyraoxystrobin, mandestrobin, pyraclostrobin, pyrametostrobin, triclopyricarb, kresoxim-methyl, trifloxystrobin, dimeoxystrobin, fenamistrobin, methominostrobin, orysastrobin, famoxadone, fluoxastrobin, fenamidone, pyribencarb, cyazofamid, amisulbrom, fentin chloride, fentin acetate, fentin hydroxide, cyprodinil, mepanipyrim, pyrimethanil, quinoxyfen, proquinazid, fenpiclonil, fludioxonil, chlozolinate, dimethachlone, iprodione, procymidone, vinclozolin, triforine, pyrifenox, pyrisoxazole, fenarimol, nuarimol, imazalil, oxpoconazole, pefurazoate, prochloraz, triflumizole, azaconazole, bitertanol, bromuconazole, cyproconazole, diniconazole, epoxiconazole, etanconazole, fenbuconazole, fluquinconazole, flusilazole, flutriafol, hexaconazole, imibenconazole, ipconazole, metconazole, myclobutanil, penconazole, propiconazole, simeconazole, tebuconazole, tetraconazole, triadimefon, triadimenol, triticonazole, prothioconazole, dimethomorph, flumorph, pyrimorph, benthiavalicarb, iprovalicarb, valifenalate, mandipropamid, captan, captafol, folpet, and chlorothalonil.

Of the above compounds, one or more of which can be used as a second anti-fungal compound in a contemplated composition admixed with a benzoxaborole of Formula I, the following are preferred: carbendazim, thiabendazole, thiophanate, thiophanate-methyl, zoxamide, ethaboxam, benomyl, fuberidazole, azoxystrobin, coumoxystrobin, enoxastrobin, flufenoxystrobin, picoxystrobin, pyraoxystrobin, mandestrobin, pyraclostrobin, pyrametostrobin, triclopyricarb, kresoxim-methyl, trifloxystrobin, dimeoxystrobin, fenamistrobin, methominostrobin, orysastrobin, famoxadone, fluoxastrobin, fenamidone, pyribencarb, cyazofamid, amisulbrom, fentin chloride, fentin acetate, fentin hydroxide, cyprodinil, mepanipyrim, pyrimethanil, quinoxyfen, proquinazid, fenpiclonil, fludioxonil, chlozolinate, dimethachlone, iprodione, procymidone, vinclozolin, triforine, pyrifenox, pyrisoxazole, fenarimol, nuarimol, imazalil, oxpoconazole, pefurazoate, prochloraz, triflumizole, azaconazole, bitertanol, bromuconazole, cyproconazole, diniconazole, epoxiconazole, etanconazole, fenbuconazole, fluquinconazole, flusilazole, flutriafol, hexaconazole, imibenconazole, ipconazole, metconazole, myclobutanil, penconazole, propiconazole, simeconazole, tebuconazole, tetraconazole, triadimefon, triadimenol, triticonazole, prothioconazole, dimethomorph, flumorph, pyrimorph, benthiavalicarb, iprovalicarb, valifenalate, mandipropamid, captan, captafol, folpet, and chlorothalonil.

FRAC Code List© 2015

| Mode of Action | Target Site and Code | Numerical FRAC Code |
|---|---|---|
| A: nucleic acid synthesis | | |
| | A1: RNA polymerase 1 | 4 |
| | A2: adenosindeaminase | 8 |
| | A3: DNA/RNA synthesis | 32 |
| | A4: DNA topoisomerase type II | 31 |
| B: mitosis and cell division | | |
| | B1: β-tubulin assembly in mitosis | 1 |
| | B2: β-tubulin assembly in mitosis | 10 |
| | B3: β-tubulin assembly in mitosis | 22 |
| | B4: cell division | 20 |
| | B5: delocalization of spectrin-like proteins | 43 |
| C: respiration | | |
| | C1: complex I NADH Oxido-reductase | 39 |
| | C2: complex II: succinate-dehydrogenase | 7 |
| | C3: complex III: cytochrome bc1 at Qo site | 11 |
| | C4: complex III: cytochrome bc1 at Qi site | 21 |
| | C5: uncoupler of oxidative phosphorylation | 29 |
| | C6: uncoupler of oxidative phosphorylation, ATP synthase | 30 |
| | C7: ATP production | 38 |
| | C8: complex III: cytochrome bc1 at Qo site, stigmatellin binding sub-site | 45 |
| D: amino acids and protein synthesis | | |
| | D1: methionine biosynthesis | 9 |
| | D2: protein synthesis | 23 |
| | D3: protein synthesis | 24 |
| | D4: protein synthesis | 25 |
| | D5: protein synthesis | 41 |

-continued

| Mode of Action | Target Site and Code | Numerical FRAC Code |
|---|---|---|
| E: signal transduction | | |
| | E1: signal transduction | 13 |
| | E2: MAP/Histidine-kinase in osmotic signal transduction | 12 |
| | E2: MAP/Histidine-kinase in osmotic signal transduction | 2 |
| F: lipid synthesis and membrane integrity | | |
| | F1: (formerly dicarboximides) | — |
| | F2: phospholipid biosynthesis, methyltransferase | 6 |
| | F3: lipid peroxidation | 14 |
| | F4: cell membrane permeability, fatty acids | 28 |
| | F5: (formerly CAA-fungicides) | — |
| | F6: microbial disrupters of pathogen cell membranes | 44 |
| | F7: cell membrane disruption | 46 |
| G: sterol biosynthesis in membranes | | |
| | G1: C14-demethylase in sterol biosynthesis | 3 |
| | G2: $\Delta^{14}$-reductase and $\Delta^8 \rightarrow \Delta^7$ isomerase in sterol biosynthesis | 5 |
| | G3: 3-ketoreductase, C4-demethylation | 17 |
| | G4: squalene-epoxidase in sterol biosynthesis | 18 |
| H: cell wall biosynthesis | | |
| | H3: trehalase and inositol biosynthesis | 26 |
| | H4: chitin_synthase | 19 |
| | H5: cellulose synthase | 40 |
| I: melanin synthesis in cell wall | | |
| | I1: reductase in melanin biosynthesis | 16.1 |
| | I2: dehydrase in melanin biosynthesis | 16.2 |
| | I3: polyketide synthase in melanin biosynthesis | 16.3 |
| P: host plant defense induction | | |
| | P1: salicylic acid pathway | P1 |
| | P2 | P2 |
| | P3 | P3 |
| | P4 | P4 |
| | P5 | P5 |
| U: unknown mode of action | | |
| | unknown | 27 |
| | unknown | 33 |
| | unknown | 34 |
| | unknown | 35 |
| | unknown | 36 |
| | unknown | 37 |
| | unknown | 42 |
| | unknown | U6 |
| | actin disruption | U8 |
| | cell membrane disruption | U12 |
| | unknown | U13 |
| | unknown | U14 |
| | oxysterol binding protein inhibition | U15 |
| | complex III | U16 |
| | unknown | U17 |

-continued

| Mode of Action | Target Site and Code | Numerical FRAC Code |
|---|---|---|
| M: multi-site contact activity | | |
| | — | M1 |
| | — | M2 |
| | — | M3 |
| | — | M4 |
| | — | M5 |
| | — | M6 |
| | — | M7 |
| | — | M8 |
| | — | M9 |
| | — | M10 |
| | — | M11 |

It is therefore to be understood that a contemplated second anti-fungal agent can be one of many compounds having anti-fungal activity. Exemplary second anti-fungal agents and their FICI values alone, as the sole anti-fungal agent (compound), and when in admixture in an anti-fungal composition are provided in Table 1 and Table 2 hereinafter.

The FICI values observed are related to the minimal inhibitory concentrations (MICs) of the individual anti-fungal agents when used as the sole active anti-fungal agent against a preselected, target fungus, in that each of the fractions $[(1/DRI)_1]$ and $(1/DRI)_2]$ represents that fraction of each initial MIC that when summed provides a minimum inhibitory concentration for the combination. MIC is defined herein as the lowest (smallest) concentration of anti-fungal agent(s) that inhibits target fungal growth by 95% or more under a predetermined set of growth conditions. The MICs of the individual anti-fungal agents can also be referred to as $MIC_{Boron}$ (for benzoxaborole anti-fungal agents) and $MIC_A$ (for non-benzoxaborole anti-fungal agents), and the combination MIC is referred to as $MIC_{BA}$. These values and their determinations are discussed in greater detail hereinafter.

Some fungi are dimorphic and can live and grow in one or the other or both of two states. In one state, referred to as the yeast phase, the fungus grows with little to no sign of hyphal/filament development, whereas the second state is the filamentous phase in which the organism grows in the form of hyphae or filaments. Thus far, synergistic activity (advantage of benzoxaborole-containing mixture) against yeast phases has not been observed, so it is preferred to treat dimorphic fungi that exist predominatly in the filamentous phase.

A synergistic relationship between the two compounds indicates that each compound is utilized for fungal control at a concentration that is less than the MIC that is normally obtained for either compound when used individually. A synergistic result for the purposes of this invention takes a more moderate approach than that of Chou discussed before, where synergy is defined as a FICI value that is less than or equal to (≤) 1.0, and rather presumes that synergy is present when FICI ≤0.7. More preferably, the FICI-based synergy determination is made at a value of ≤0.5. As can be seen from the data of Table 2 that list synergistic combinations, hereinafter, FICI values of 0.1 have been observed, and such values can be about 0.01, or less.

It is to be remembered that $$FICI = \frac{1}{(DRI)_1} + \frac{1}{(DRI)_2}.$$

An easy way to determine a synergistic FICI value is to begin with an anti-fungal composition that contains an MIC of each anti-fungal agent separately determined under a particular set of conditions. Using serial dilutions of the initial anti-fungal composition having each anti-fungal agent at its MIC, the inhibition of fungal growth is assayed under those same conditions until growth inhibition ceases. This method is discussed and illustrated hereinafter.

Using the more preferred FICI-based synergy determination value of ≤0.5, each anti-fungal agent would be present at most at ¼ of its separate MIC concentration as FICI=(¼+¼)=½=0.5. Looked at differently, a MIC of each anti-fungal agent alone is at least 4-times greater than that of the synergistic concentration.

Similarly, a FICI value of 0.1 obtained by the serial dilution method can be obtained from an anti-fungal composition diluted so that each anti-fungal agent is present at $1/20^{th}$ of its individual MIC. This is seen by FICI=(1/20+1/20)=(0.05+0.05)=0.1. Here, the MIC of each compound alone is 20-times greater than in the MIC of the synergistic anti-fungal composition.

It is to be understood that use of serial dilutions of an initial anti-fungal composition each of whose anti-fungal agents is initially present at its MIC as a single anti-fungal agent is not the only way to determine a FICI MIC value. One could also combine different sub-MIC amounts of the anti-fungal agents and obtain a FICI value that is 0.5 or less. Thus, for example, one agent could be present at $1/10^{th}$ of its MIC alone and the other at $2/5^{th}$ of its MIC alone. Here, FICI=(1/10+2/5)=(0.1+0.4)=0.5.

Regardless of the manner of calculation of the FICI value, it is preferred that the ratio of MIC of one anti-fungal agent used alone to the concentration of that agent in an anti-fungal composition is greater than about 1.6, so that the reciprocal of that ratio is less than about 0.6. More preferably, the ratio of MIC of one anti-fungal agent used alone to the concentration of that agent in an anti-fungal composition is greater than about 2, so that the reciprocal of that ratio is less than about 0.5. Thus, the ratio of the MIC of the second anti-fungal agent to the concentration of the second anti-fungal agent in a contemplated anti-fungal composition is greater than about 10, so that the reciprocal of that ratio is less than about 0.01 and the sum of those two reciprocal values is about 0.7 or less, or 0.5 or less, respectively.

The taxonomy of the fungal pests to be controlled include one or more of a member of the phyla of Ascomycota, Oomycota and Basidiomycota, as well as subphylum Mucoromycotina previously classified in phylum Zygomycota). It is to be noted that members of the phylum Oomycota are not formally in the Kingdom Fungi (True Fungi), but rather are formally classified in the Kingdom Straminipila (also spelled Stramenopila), many of whose members have similarities to fungi. Both Oomycota and True Fungi are heterotrophs that break down food externally and then absorb nutrients from their surroundings.
Additionally, many of the multicellular Oomycetes form hyphae, which are very similar to True Fungal hyphae although the structures are not identical. Two Oomycota caused the Irish potato famine (*Phytophthora infestans*) and the destruction of French wine grapes caused by downy mildew (*Plasmopara viticola*) during the $19^{th}$ Century, and continue to be important pests of many crops. Together, the groups can be referred to as hyphae-containing organisms, or fungi for this document.

Of the above-noted phyla, several members of the subphylum Pezizomycotina are among those that can be controlled using a contemplated composition. Of the members of the subphylum Pezizomycotina, fungi of one or more of the Classes selected from the group consisting of Dothideomycetes, Eurotiomycetes, Leotiomycetes and Sordariomycetes are particularly preferred for control by a contemplated composition.

Of those recited Classes, members of a Genus that is *Aspergillus, Botrytis*, or *Fusarium* are more particularly preferred for growth control by a contemplated composition.

A list of the phylum, subphylum, where appropriate, class, genus and species of the organisms studied herein is provided below in Table A. The first twenty-two organsims of Table A are in the Kingdom Fungi, whereas the las two are in the Kingdom Stramenopila.

TABLE A

| Phylum | Subphylum | Class | Order | Genus Species (isolate) |
|---|---|---|---|---|
| Ascomycota | Pezizomycotina | Dothideomycetes | Capnodiales | *Mycosphaerella zeae-maydis* |
| Ascomycota | Pezizomycotina | Dothideomycetes | Pleosporales | *Alternaria solani* |
| Ascomycota | Pezizomycotina | Dothideomycetes | Dothideales | *Aureobasidium pullulans* |
| Ascomycota | Pezizomycotina | Eurotiomycetes | Eurotiales | *Aspergillus flavus* |
| Ascomycota | Pezizomycotina | Eurotiomycetes | Eurotiales | *Aspergillus fumigatus* |
| Ascomycota | Pezizomycotina | Eurotiomycetes | Eurotiales | *Aspergillus niger* |
| Ascomycota | Pezizomycotina | Eurotiomycetes | Eurotiales | *Penicillium chrysogenum* |
| Ascomycota | Pezizomycotina | Leotiomycetes | Helotiales | *Sclerotinia homoeocarpa* |
| Ascomycota | Pezizomycotina | Leotiomycetes | Helotiales | *Botrytis cinerea* (10-1728) |
| Ascomycota | Pezizomycotina | Leotiomycetes | Helotiales | *Botrytis cinerea* (B17) |
| Ascomycota | Pezizomycotina | Sordariomycetes | Hypocreales | *Fusarium solani* |
| Ascomycota | Pezizomycotina | Sordariomycetes | Hypocreales | *Fusarium verticillioides* |
| Ascomycota | Pezizomycotina | Sordariomycetes | Hypocreales | *Fusarium graminearum* |
| Ascomycota | Pezizomycotina | Sordariomycetes | Hypocreales | *Fusarium solani* f. sp. *pisi* |
| Ascomycota | Pezizomycotina | Sordariomycetes | Hypocreales | *Fusarium oxysporum* f. sp. *lycopersici* |
| Ascomycota | Pezizomycotina | Sordariomycetes | Hypocreales | *Fusarium oxysporum* (ST33) |
| Ascomycota | Pezizomycotina | Sordariomycetes | Hypocreales | *Stachybotrys chartarum* |
| Ascomycota | Pezizomycotina | Sordariomycetes | Magnaporthales | *Magnaporthe grisea* |
| Ascomycota | Pezizomycotina | Sordariomycetes | Glonterellales | *Colletotrichum orbiculare* |
| Ascomycota | Saccharomycotina | Saccharomycetes | Saccharomycetales | *Candida albicans* |
| Basidiomycota | Agaricomycotina | Agaricomycetes | Canthrarellales | *Rhizoctonia solani* |
| incertae sedis | Mucoromycotina | Mucoromycetes | Mucorales | *Mucor* sp. |
| incertae sedis | Mucoromycotina | Mucoromycetes | Mucorales | *Rhizopus* sp. |
| Oomycota | N/A | Oomycetes | Pythiales | *Pythium aphanodermatum* |
| Oomycota | N/A | Oomycetes | Peronosporales | *Phytophthora pini* |

An anti-fungal composition is comprised of a diluent medium in which the two anti-fungal agents are dissolved or dispersed. A contemplated anti-fungal composition is peferably formulated for topical, foliar or systemic administration, in which case, the composition is formulated to have a viscosity greater than that of water on up to that of a solid as when a powder, granulate or the like is used. A composition can also have a viscosity substantially greater than that of water when soil or other growing medium is to be treated.

The anti-fungal agents and diluent medium are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomizing, dusting, scattering, coating or pouring, are chosen in accordance with the intended objectives and the prevailing circumstances. A contemplated composition can also contain further adjuvants such as stabilizers, antifoams, viscosity regulators, binders or tackifiers as well as fertilizers, micronutrient donors or other formulations for obtaining special effects.

Suitable diluent media and adjuvants (auxiliaries) can be solid or liquid and are substances useful in formulation technology, e.g. natural or regenerated mineral substances, solvents, dispersants, wetting agents, tackifiers, thickeners, binders or fertilizers. Such diluent media are for example described in WO 97/33890, which is hereby incorporated by reference. Water-based (more than 50 weight percent water) diluent media are presently preferred and are used illustratively herein.

The two anti-fungal agents, or more preferably, a composition containing them, in appropriate synergistic amounts dissolved or dispersed in a diluent medium can be applied to the area of soil or other growth medium from which the plant to be treated obtains its nutrients, or directly on to the plant, seed or harvested plantpart to be treated, simultaneously or in succession with further compounds. These further compounds can be e.g. fertilizers or micronutrient donors or other preparations that influence the growth of plants. The micronutrient can be other water soluble boron products that primarily provide the nutrients to facilitate plant health. They can also be selective herbicides as well as insecticides, bactericides, nematicides, molluscicides or mixtures of several of these preparations, if desired together with further carriers, surfactants or application promoting adjuvants customarily employed in the art of formulation.

More particularly, a contemplated anti-fungal composition invention can be employed in any conventional form, for example in the form of a powder, an emulsion, a flowable concentrate, a solution, a water dispersible powder, a capsule suspension, a gel, an emulsion concentrate, a suspension concentrate, a suspo-emulsion (an emulsion containing both solid and liquid anti-fungal agents in an aqueous medium), a capsule suspension, a water dispersible granule, an emulsifiable granule, a water in oil emulsion, an oil in water emulsion, a micro-emulsion, an oil dispersion, an oil miscible liquid, a soluble concentrate, an ultra-low volume suspension, an ultra-low volume liquid, a technical concentrate, a dispersible concentrate, a wettable powder or any technically feasible formulation.

Such anti-fungal compositions can be produced in a conventional manner, e.g. by mixing the active ingredients with appropriate formulation inerts that comprise the diluent medium such as solid or liquid carriers and optional other formulating ingredients such as surface-active compounds (surfactants), biocides, anti-freeze agents, stickers, thickeners and compounds that provide adjuvancy effects, and the like. Also, conventional slow release formulations can be employed where long-lasting efficacy is intended. Particularly, formulations to be applied in spraying forms, such as water dispersible concentrates, wettable powders and granules, can contain surfactants such as wetting and dispersing agents and other compounds that provide adjuvancy effects, e.g., the condensation product of formaldehyde with naphthalene sulphonate, an alkylarylsulphonate, a lignin sulphonate, a fatty alkyl sulphate, and ethoxylated alkylphenol, trisiloxane ethoxylate, and an ethoxylated fatty alcohol.

The term "carrier" is used herein to denote a natural or synthetic, organic or inorganic material that constitutes a portion of the diluent medium in which the two anti-fungal agents are dispersed or dissolved. This carrier is hence generally inert, and it must be agriculturally acceptable, in particular to the plant being treated. The phrase "agriculturally acceptable" is utilized herein to be analogous to "pharmaceutically acceptable" as used in pharmaceutical products to describe diluent media. A carrier can be solid (clays, natural or synthetic silicates, silica, resins, waxes, solid fertilizers, and the like) or liquid (water, alcohols, ketones, petroleum fractions, aromatic or paraffinic hydrocarbons, chlorinated hydrocarbons, liquefied gases, and the like).

Solid, particulate carriers that can be used, for example for dusts and dispersible powders, are calcite, talc, kaolin, diatomaceous earth, montmorillonite or attapulgite, highly-disperse silica or absorptive polymers. Illustrative particulate, adsorptive carriers for granules include pumice, crushed brick, sepiolite or bentonite, montmorillonite-type clay, and exemplary nonsorbent carrier materials are calcite or dolomite. A particulate solid formulation can also be prepared by encapsulation of a suitable mixture of fungicides or bya granulation process tha utilizes one or more of the above diluents or an organic diluent such as microcrystalline cellulose, rice hulls, wheat middlings, saw dust and the like. Illustrative granules can be prepared as discussed in U.S. Pat. No. 4,936,901, U.S. Pat. No. 3,708,573 and U.S. Pat. No. 4,672,065.

Suitable liquid carriers include: aromatic hydrocarbons, in particular the fractions $C_8$-$C_{12}$, such as xylene mixtures or substituted naphthalenes, phthalic esters such as dibutyl or dioctyl phthalate, aliphatic hydrocarbons such as cyclohexane or paraffins, alcohols and glycols as well as their ethers and esters, such as ethylene glycol monomethyl ether, ketones such as cyclohexanone, strongly polar solvents such as N-methyl-2-pyrrolidone, dimethyl sulfoxide or dimethylformamide, and, if appropriate, epoxidized vegetable oils such as soybean oil and water. If appropriate, the liquid carrier can be a naturally occurring essential oil, such as oils from citronella and lemon grass.

Suitable surface-active compounds are non-ionic, cationic and/or anionic surfactants having good emulsifying, dispersing and wetting properties, depending mostly on the nature of the second anti-fungal agent to be formulated in the a contemplated benzoxaborole is water soluble. The term "surfactants" is also to be understood as meaning mixtures of two or more surface-active compounds.

The surfactants customarily employed in formulation technology are described, inter alia, in the following publications: *McCutcheon's Detergents and Emulsifiers Annual*, MC Publishing Corp., Glen Rock, N.J., 1988; M. and J. Ash, *Encyclopedia of Surfactants,* Vol. I-III, Chemical Publishing Co., New York, 1980-1981.

Among the suitable illustrative surfactants there can be mentioned, e.g., polyacrylic acid salts, lignosulphonic acid salts, phenolsulphonic or (mono- or di-alkyl) naphthalenesulphonic acid salts, laurylsulfate salts, polycondensates of ethylene oxide with lignosulphonic acid salts, polycondensates of ethylene oxide with fatty alcohols or with fatty acids or with fatty amines, substituted phenols (in particular alkylphenols or arylphenols such as mono- and di-(polyoxyalkylene alkylphenol) phosphates, polyoxyalkylene alkylphenol carboxylates or polyoxyalkylene alkylphenol sulfates), salts of sulphosuccinic acid esters, taurine derivatives (in particular alkyltaurides), polycondensates of ethylene oxide with phosphated tristyrylphenols and polycondensates of ethylene oxide with phosphoric esters of alcohols or phenols. The presence of at least one surfactant is often required because the second anti-fungal agent and/or the inert vehicles are not readily soluble in water and the anti-fungal composition preferably used for the administration is water.

Furthermore, particularly useful adjuvants which enhance application are natural or synthetic phospholipids from the series of the cephalins and lecithins, for example phosphatidylethanolamine, phosphatidylserine, phosphatidylglycerine or lysolecithin.

A contemplated anti-fungal composition can also include at least one polymer that is a water-soluble or water-dispersible film-forming polymer that improves the adherence of at least the anti-fungal agents to the treated plant propagation material. An exemplary polymer generally has an average molecular weight of at least 10,000 to about 100,000.

Typically, a coloring agent, such as a dye or pigment, is included in an anti-fungal composition so that an observer can immediately determine that the plant has been treated. An anti-fungal composition that includes a coloring agent is a preferred embodiment of the invention, as such a composition can improve user and consumer safety. The coloring agent is also useful to indicate to the user the degree of uniformity of application of a composition. Generally, the coloring agent tends to have a melting point above 30° C., and therefore, is suspended in a contemplated anti-fungal composition. The colouring agent can also be a soluble compound.

As examples of coloring agents can be mentioned pigment red 48-2 (CAS-7023-61-2), pigment blue 15 (CAS-147-14-8), pigment green 7 (CAS-1328-53-6), pigment violet 23 (CAS-6358-30-1), pigment red 53-1 (CAS-5160-02-1), pigment red 57-1 (CAS 5281-04-9), pigment red 112 (CAS 6535-46-2) or similar colouring agents. A colouring agent is typically present at about 0.1 to about 10% by mass of an anti-fungal composition.

In typical use, a commercial product is preferably formulated as a concentrate also known as a pre-mix composition (or concentrate, formulated compound), and the end user normally employs a diluted formulation for administration to the plants of interest. Such a diluted composition is often referred to as a tank-mix composition. A tank-mix composition is generally prepared by diluting a pre-mix anti-fungal composition (concentrate) with a solvent such as water that can optionally also contain further auxiliaries. Generally, an aqueous tank-mix is preferred.

In general, a concentrate anti-fungal formulation includes about 0.01 to about 90% by weight anti-fungal agents, about 0 to about 20% agriculturally acceptable surfactant and 10 to 99.99% solid or liquid carriers and adjuvant(s).

A concentrate anti-fungal formulation generally contains about 2 to about 80%, preferably about 5 to about 70% by weight of combined first and second anti-fungal agent. A tank-mix or slurry forms of an anti-fungal composition (diluted formulations) is diluted to contain synergistic amounts of each of the two anti-fungal agents, the synergistic amount of each anti-fungal agent being less than the MIC of each agent alone as determined for the contemplated application conditions.

After surveying over 800 examples (different drug combinations and different fungal organisms; Tables 2 and 3), it was found that the benzoxaboroles (BO, B90, B18, and similar derivatives) exhibit a very high level of synergism with many anti-fungal compounds that target very different modes of action (different protein or different FRAC "Target Site and Code"). The high level of synergistic drug combination occurrence (Tables 4 and 5, hereinafter) between benzoxaborole anti-fungal compounds and other non-benzoxaborole compounds, was much greater than what one might predict for a specific class of compounds when considering drug-drug interactions and the before-discussed findings of Yin et al., *PLOS* 9:e93960 (2014); Cokol et al., *Mol. Systems Biol.* 7:544 (2011); and Borisy et al., *Proc. Natl Acad. Sci.* 100:7977-7982 (2003) as to the rarity of finding synergistic drug combinations.

It is presently unclear how disrupting general protein synthesis affects various individual biological processes. Several mechanisms of action appear to be possible, but there is presently no evidence available that supports a general mechanism of action for any of these synergisms between benzoxaborales and other anti-fungals.

Table 4 shows that the benzoxaboroles (specifically compounds BO, B18, and B90) can be considered "master enhancers" that have a very good likelihood (more than ⅓ chance) to synergize with most compounds in the FRAC Target Site Code listed in Table 4. Table 4 shows the percentage of synergistic combinations in relation to all the anti-fungal+anti-fungal combination studies conducted herein.

In fact, benzoxaboroles were able to form synergistic combinations with compounds in the following FRAC Target Site and Code group at greater than an about 30% rate (one third of the time): B, C, D, E, G, H, and M. However, the present data indicate that benzoxaobroles do not seem to commonly form synergistic combinations with compounds from FRAC Target Site and Code group of A, F, I, and P.

Further breakdown of the "pairing anti-fungal compounds" (compounds that pair synergistically with benzoxaboroles) into specific target sites (mode of action) revealed further levels of specificity (Table 5, hereinafter). Thus, in addition to the FRAC "Target Site and Code" not examined (e.g. A3, A4, B4, B5, C1, C7, C8, D2, D4, D5, F6, F7, G2, G4, H3, H4, I1, I3, or sub groups in P, U, and M), there are many FRAC "Target site and Code" groups (e.g., B3, D3, E1, F3, F4, H5, 12, and P2) where fewer than a dozen samples were tested. This was mainly due to the narrow spectrum of efficacy in these groups (i.e. D3, E1, F3, F4, H5, I2, and P2 were not effective against as many fungal species). Nonetheless, compounds in "FRAC Target site and Code" of B3, E1, and H5 all exhibited more than a 50% chance of forming synergistic combinations with benzoxaborole anti-fungals in reducing fungal growth.

Overall, examination of Table 5 reveals that benzoxaboroles can routinely form synergistic combinations with compounds in the following FRAC Codes at about a 30% rate: B1, B3, C3, C4, C6, D1, E1, E2, E3, G1, H5, M4, and M5. Indeed, compounds in FRAC Codes of C3, D1, and E2 provided more than A 50% likelihood of forming synergistic combinations with a contemplated benzoxaborole. Thus, a composition containing a benzoxaborole anti-fungal compound and one or more anti-fungal compounds from an above "FRAC Code" group is unexpectedly likely to provide an effective anti-fungal composition, pre-mix and/or tank mixes.

The examined benzoxaborles, however, do not as readily form synergistic combinations with compounds from the following FRAC Codes: A1, A2, B2, C2, C5, D3, F2, F3, F4, G3, I2, M3, and P2. Some synergistic combinations have been observed in these FRAC Code groups.

Results

The individual MIC values of various antifungals against two dozen different fungal organisms are tabulated in Table 1, hereinafter. All antifungal susceptibility assays were conducted in triplicate and N independent times. Thus, the inhibition studies were conducted a total of 3·N times. The results were extremely consistent within each independent run, and the variations between independent runs can be attributed to discrepancies in the experimental conditions (vitality of the fungal inoculum, medium, temperature, light intensity, etc.). Thus, each synergy assay (combination of two antifungals) was conducted in conjunction with independent MIC determination. FICI values were calculated by comparing the inhibition activity of the combination (benzoxaborole+another antifungal) against the efficacy of the individual antifungal within the same experiment (using the same experimental conditions).

By itself, a studied benzoxaborole (BO, B18, B90, B1) exhibited broad spectrum and potent antifungal activity against the organisms examined (Table 1) with MIC values regularly at ≤4 ppm. Most non-benzoxaborole antifungals tested here are only effective against a selective few organisms, and this is true even for many antifungals that possess multiple modes of action (e.g., captan, mancozeb, maneb, zineb, chlorothalonil, and metam sodium exhibited MIC values >25 μg/mL against many species tested here). Surprisingly, the benzoxaboroles are very active (MIC <4 μg/mL) for many organisms (both True Fungi and Oomycetes) that exhibit high drug tolerance/resistance (MIC >200 μg/mL) against most antifungals (such as the ones tested here).

TABLE 1

Range of MIC values (unit in μg/mL) of the individual antifungals and the number of independent (N) triplicate studies*

| Antifungal Compound | Independent MIC (μg/mL) | N |
|---|---|---|
| *Mycosphaerella zeae-maydis* | | |
| BO | (2-8) | 7 |
| B18 | (4-8) | 5 |
| B90 | (1-8) | 4 |
| B1 | 16 | 1 |
| B2 | >32 | 1 |
| Fludioxonil | 2 | 2 |
| Vinclozolin | (6.25-16) | 3 |
| Pyraclostrobin | (2-4) | 3 |
| Propiconazole | (3-6.25) | 2 |
| Captan | (1-1.56) | 2 |
| Mancozeb | (3.125-8) | 3 |
| Fenhexamid | (100-200) | 3 |
| Thiophanate-Methyl | (25-50) | 3 |
| Pyrimethanil | (6.25-12.5) | 2 |
| Thiabendazole | (12.5-25) | 2 |
| Edifenphos | (200-400) | 2 |
| Fentin Chloride | 50 | 2 |
| Maneb | 25 | 2 |
| Zineb | (1.56-2) | 2 |
| Chlorothalonil | (0.78-1) | 2 |
| Cyproconazole | (3.125-6) | 2 |
| Fluazinam | (1-1.56) | 2 |

TABLE 1-continued

Range of MIC values (unit in μg/mL) of the individual antifungals and the number of independent (N) triplicate studies*

| Antifungal Compound | Independent MIC (μg/mL) | N |
|---|---|---|
| Metam Sodium | (6-6.25) | 2 |
| Tebuconazole | (50-100) | 2 |
| Cyprodinil | 1.56 | 2 |
| Carbendazim | (1.56-2) | 2 |
| Probenazole | 200 | 2 |
| Fenamidone | (50-200) | 3 |
| Azoxystrobin | 20 | 2 |
| Ethirimol | 400 | 2 |
| Cyazofamid | 100 | 2 |
| *Alternaria solani* | | |
| BO | (2-4) | 3 |
| B18 | 0.5 | 5 |
| B90 | (0.25-0.5) | 5 |
| B1 | 1 | 1 |
| B2 | >32 | 1 |
| Propiconazole | (100-160) | 2 |
| Captan | (1.5-3.125) | 2 |
| Iprodione | (3.125-6.25) | 2 |
| Mancozeb | (10-12.5) | 2 |
| Fenhexamid | (100-200) | 3 |
| Pyrimethanil | (100-200) | 3 |
| Edifenphos | 200 | 2 |
| Fentin Chloride | (10-12.5) | 2 |
| Maneb | (25-50) | 2 |
| Propamocarb | (100-200) | 2 |
| Zineb | (6.25-12.5) | 2 |
| Chlorothalonil | (1-1.56) | 2 |
| Fluazinam | (0.5-0.78) | 2 |
| Metam Sodium | (12.5-15) | 2 |
| Tebuconazole | (25-50) | 2 |
| Cyprodinil | 100 | 2 |
| Fenoxanil | 200 | 3 |
| Kasugamycin | (100-200) | 2 |
| Probenazole | 200 | 2 |
| Fenamidone | (100-200) | 2 |
| Azoxystrobin | 100 | 2 |
| Pyraclostrobin | (50-100) | 2 |
| *Aureobasidium pullulans* | | |
| BO | (1-2) | 2 |
| B18 | 0.125 | 2 |
| B90 | (0.25-0.5) | 2 |
| B1 | 1 | 1 |
| B2 | >32 | 1 |
| Fludioxonil | (3-3.125) | 2 |
| Pyraclostrobin | (0.188-0.78) | 2 |
| Propiconazole | (1.56-6) | 2 |
| Captan | (0.375-0.78) | 2 |
| Iprodione | (12.5-50) | 2 |
| Mancozeb | (6.25-12.5) | 2 |
| Fenhexamid | 100 | 2 |
| Etridiazole | (200-400) | 2 |
| Thiophanate-Methyl | (0.1-0.39) | 2 |
| Pyrimethanil | (25-50) | 2 |
| Thiabendazole | (0.2-0.39) | 2 |
| *Aspergillus flavus* | | |
| BO | (2-5) | 8 |
| B18 | (0.5-1) | 3 |
| B90 | (0.5-1) | 6 |
| B1 | 2 | 1 |
| B2 | >32 | 1 |
| Metalaxyl | 400 | 2 |
| Propiconazole | (6.25-12.5) | 3 |
| Captan | (12.5-25) | 3 |
| Mancozeb | (6.25-25) | 2 |
| Fenhexamid | (3.125-6.25) | 3 |
| Pyrimethanil | 25 | 2 |
| Thiabendazole | (12.5-40) | 2 |
| Fentin Chloride | (0.78-1) | 2 |
| Maneb | (12.5-25) | 2 |
| Zineb | (1-1.56) | 2 |
| Chlorothalonil | (0.1-0.2) | 2 |

TABLE 1-continued

Range of MIC values (unit in μg/mL) of the individual antifungals and the number of independent (N) triplicate studies*

| Antifungal Compound | Independent MIC (μg/mL) | N |
|---|---|---|
| Cyproconazole | (50-100) | 2 |
| Fluopyram | 200 | 2 |
| Mepanipyrim | 0.75 | 2 |
| Metam Sodium | 25 | 2 |
| Tebuconazole | (3-3.125) | 2 |
| Cyprodinil | (0.75-1.56) | 3 |
| Carbendazim | (0.78-3.125) | 2 |
| Penthiopyrad | 100 | 2 |
| *Aspergillus fumigatus* | | |
| BO | (0.5-1) | 3 |
| B18 | (0.125-0.25) | 8 |
| B90 | (0.063-0.125) | 5 |
| B1 | 0.25 | 1 |
| B2 | >32 | 1 |
| Fludioxonil | (0.25-1) | 4 |
| Metalaxyl | 400 | 2 |
| Vinclozolin | (100-200) | 2 |
| Pyraclostrobin | (20-25) | 2 |
| Propiconazole | (2.5-6.25) | 3 |
| Captan | (6.25-12.5) | 3 |
| Iprodione | (12.5-50) | 4 |
| Mancozeb | 100 | 2 |
| Fenhexamid | 400 | 2 |
| Thiophanate-Methyl | (50-100) | 3 |
| Azoxystrobin | (50-100) | 2 |
| Pyrimethanil | (0.78-1) | 2 |
| Thiabendazole | (12.5-50) | 3 |
| Edifenphos | 200 | 2 |
| Fentin Chloride | 0.78 | 3 |
| Maneb | 3.125 | 2 |
| Zineb | (0.78-1.56) | 2 |
| Chlorothalonil | (0.1-0.2) | 3 |
| Cyproconazole | (12.5-25) | 2 |
| Fluopyram | (3.125-6.25) | 2 |
| Mepanipyrim | (0.05-0.1) | 2 |
| Metam Sodium | 25 | 2 |
| Tebuconazole | (0.78-1.56) | 2 |
| Carbendazim | (1.56-3.125) | 2 |
| Picoxystrobin | (25-50) | 2 |
| *Aspergillus niger* | | |
| BO | (2-2.5) | 3 |
| B18 | (0.5-2) | 6 |
| B90 | (0.25-1) | 5 |
| B1 | 2 | 1 |
| B2 | >32 | 1 |
| Metalaxyl | 400 | 2 |
| Vinclozolin | (50-100) | 2 |
| Pyraclostrobin | (25-50) | 2 |
| Propiconazole | 12.5 | 2 |
| Captan | (12.5-16) | 2 |
| Iprodione | (50-100) | 2 |
| Mancozeb | (25-50) | 2 |
| Thiophanate-Methyl | 25 | 2 |
| Pyrimethanil | (100-200) | 2 |
| Thiabendazole | (12.5-50) | 2 |
| Fentin chloride | (0.78-1) | 2 |
| Maneb | (50-100) | 2 |
| Chlorothalonil | (0.39-1) | 2 |
| Cyproconazolecy | 25 | 2 |
| Fluazinam | 3.125 | 2 |
| Fluopyram | (0.78-1.56) | 2 |
| Mepanipyram | 25 | 2 |
| Metam Sodium | 50 | 2 |
| Tebuconazole | 3.125 | 2 |
| Cyprodinil | 3.12 | 2 |
| Carbendazim | (1-1.56) | 2 |
| Iprobenfos | (200-300) | 2 |
| Boscalid | (0.39-0.5) | 2 |
| Fluxapyroxad | (0.39-0.4) | 2 |
| Penthiopyrad | (0.78-1.56) | 2 |

TABLE 1-continued

Range of MIC values (unit in μg/mL) of the individual antifungals and the number of independent (N) triplicate studies*

| Antifungal Compound | Independent MIC (μg/mL) | N |
|---|---|---|
| *Sclerotinia homoeocarpa* | | |
| BO | (2-8) | 11 |
| B18 | (1-4) | 7 |
| B90 | (0.25-1) | 6 |
| B1 | 1 | 1 |
| B2 | >32 | 1 |
| Fludioxonil | (0.125-0.25) | 3 |
| Metalaxyl | (128-200) | 2 |
| Vinclozolin | (4-5) | 2 |
| Pyraclostrobin | 0.5 | 2 |
| Propiconazole | (0.5-1) | 2 |
| Captan | (2-4) | 4 |
| Iprodione | (4-10) | 2 |
| Mancozeb | (8-20) | 2 |
| Fenhexamid | 64 | 2 |
| Thiophanate-Methyl | (0.5-1) | 3 |
| Pyrimethanil | (50-100) | 4 |
| Thiabendazole | (20-25) | 2 |
| Edifenphos | (3.125-6.25) | 2 |
| Fentin Chloride | 12.5 | 2 |
| Maneb | 1.56 | 2 |
| Propamocarb | 200 | 2 |
| Zineb | (6.25-12.5) | 3 |
| Chlorothalonil | (0.39-0.78) | 3 |
| Cyproconazole | (1.56-3.125) | 2 |
| Fluazinam | (3.125-6.25) | 2 |
| Fluopyram | (0.78-3.125) | 2 |
| Mepanipyrim | (0.098-0.19) | 3 |
| Metam Sodium | 6.25 | 3 |
| Tebuconazole | (0.39-0.78) | 3 |
| Cyprodinil | 0.39 | 2 |
| Fenoxanil | 200 | 2 |
| Kasugamycin | 100 | 2 |
| Carbendazim | (0.05-0.1) | 3 |
| Bupirimate | (50-100) | 2 |
| Probenazole | (50-100) | 2 |
| Fenamidone | (100-200) | 2 |
| Diethofencarb | (100-200) | 2 |
| Iprobenfos | (12.5-25) | 2 |
| Picoxystrobin | 1.56 | 2 |
| Ethirimol | 200 | 2 |
| Boscalid | 0.8 | 2 |
| Cyazofamid | 100 | 2 |
| *Botrytis cinerea* 10-1728 | | |
| BO | (1-2.5) | 6 |
| B18 | (0.5-2) | 8 |
| B90 | (0.25-0.5) | 4 |
| B1 | 2 | 1 |
| B2 | >32 | 1 |
| Fludioxonil | (0.5-0.78) | 2 |
| Vinclozolin | (100-400) | 3 |
| Pyraclostrobin | 200 | 2 |
| Propiconazole | (1.25-3.125) | 2 |
| Captan | (0.94-1.56) | 2 |
| Iprodione | (15-25) | 2 |
| Mancozeb | 3.125 | 2 |
| Fenhexamid | 200 | 2 |
| Thiophanate-Methyl | (200-400) | 3 |
| Azoxystrobin | (110-400) | 3 |
| Flutolanil | 400 | 2 |
| Pyrimethanil | (50-100) | 2 |
| Thiabendazole | (200-400) | 3 |
| Edifenphos | (100-200) | 2 |
| Fentin Chloride | (50-100) | 2 |
| Maneb | (12.5-40) | 2 |
| Propamocarb | (100-400) | 2 |
| Zineb | (3-3.125) | 2 |
| Chlorothalonil | (0.2-0.5) | 2 |
| Cyproconazole | (0.78-2) | 2 |
| Dimethomorph | (100-200) | 2 |
| Fluazinam | (1-1.56) | 2 |
| Fluopyram | (1.56-4) | 2 |

TABLE 1-continued

Range of MIC values (unit in μg/mL) of the individual antifungals and the number of independent (N) triplicate studies*

| Antifungal Compound | Independent MIC (μg/mL) | N |
|---|---|---|
| Mepanipyrim | (50-100) | 2 |
| Metam Sodium | (50-200) | 2 |
| Quinoxyfen | (50-100) | 2 |
| Tebuconazole | (1-1.56) | 2 |
| Cyprodinil | (50-100) | 2 |
| Fenoxanil | (100-200) | 2 |
| Kasugamycin | 200 | 2 |
| Bupirimate | 100 | 2 |
| Probenazole | 100 | 2 |
| Fenamidone | 100 | 3 |
| Diethofencarb | (1.5-1.56) | 2 |
| Iprobenfos | (100-200) | 2 |
| Picoxystrobin | (100-200) | 2 |
| Ethirimol | (200-400) | 2 |
| Boscalid | (3.125-6.25) | 2 |
| Zoxamide | (0.39-1.6) | 2 |
| Fluxapyroxad | 6.25 | 2 |
| Penthiopyrad | (15-25) | 2 |
| Quintozene | 50 | 2 |
| Cyazofamid | (200-400) | 2 |
| *Botrytis cinerea* B17 | | |
| BO | (1-4) | 3 |
| B18 | 0.5 | 2 |
| B90 | (0.5-2) | 3 |
| B1 | 2 | 1 |
| B2 | >32 | 1 |
| Fludioxonil | 0.5 | 2 |
| Metalaxyl | (50-64) | 2 |
| Pyraclostrobin | (3.75-8) | 2 |
| Propiconazole | (1-2) | 2 |
| Captan | (1.88-4) | 2 |
| Iprodione | (16-20) | 2 |
| Mancozeb | (32-64) | 2 |
| Fenhexamid | 4 | 2 |
| Azoxystrobin | (12.5-25) | 2 |
| Pyrimethanil | (50-100) | 2 |
| Thiabendazole | 50 | 2 |
| *Candida albicans* | | |
| BO | 1 | 4 |
| B18 | (0.5-1) | 2 |
| B90 | 0.5 | 5 |
| Propiconazole | (100-200) | 2 |
| Mancozeb | 50 | 2 |
| Pyrimethanil | 200 | 2 |
| Fentin Chloride | (0.78-1.56) | 2 |
| Maneb | 1.56 | 2 |
| Zineb | 3.125 | 2 |
| Chlorothalonil | 0.78 | 2 |
| Cyproconazole | (100-400) | 3 |
| Metam Sodium | 25 | 2 |
| Tebuconazole | (100-200) | 2 |
| Cyprodinil | 50 | 2 |
| Iprobenfos | (200-400) | 2 |
| *Fusarium graminearum* | | |
| BO | (2-4) | 4 |
| B18 | 1 | 3 |
| B90 | (0.5-2) | 5 |
| Fludioxonil | 50 | 2 |
| Pyraciostrobin | 200 | 2 |
| Propiconazole | (12.5-25) | 2 |
| Captan | (0.78-0.8) | 2 |
| Mancozeb | 12.5 | 2 |
| Fenhexamid | (25-50) | 2 |
| Thiophanate-Methyl | (100-400) | 2 |
| Azoxystrobin | 400 | 2 |
| Pyrimethanil | 200 | 2 |
| Thiabendazole | (1.5-3.125) | 2 |
| Fentin Chloride | (50-200) | 2 |
| Maneb | 12.5 | 2 |
| Zineb | 1.56 | 2 |
| Chlorothalonil | (0.78-1.56) | 2 |

TABLE 1-continued

Range of MIC values (unit in μg/mL) of the individual antifungals and the number of independent (N) triplicate studies*

| Antifungal Compound | Independent MIC (μg/mL) | N |
|---|---|---|
| Metam Sodium | (12.5-25) | 2 |
| Cyprodinil | 200 | 2 |
| Carbendazim | 1.56 | 2 |
| Iprobenfos | (200-400) | 2 |
| Picoxystrobin | (200-400) | 2 |
| Cyazofamid | 100 | 2 |
| *Fusarium verticillioides* | | |
| BO | (1-4) | 4 |
| B18 | (0.25-0.5) | 4 |
| B90 | (0.25-0.4) | 5 |
| B1 | 0.5 | 1 |
| B2 | >32 | 1 |
| Propiconazole | (0.5-2) | 3 |
| Captan | (1-2) | 3 |
| Mancozeb | (4-8) | 2 |
| Pyrimethanil | 200 | 2 |
| Thiabendazole | (3-6.25) | 2 |
| Edifenphos | (200-400) | 2 |
| Fentin Chloride | (6.25-12.5) | 2 |
| Maneb | 6.25 | 2 |
| Zineb | (3.125-6.25) | 2 |
| Chlorothalonil | (0.75-0.78) | 2 |
| Cyproconazole | (3-3.125) | 2 |
| Fluazinam | 12.5 | 2 |
| Metam Sodium | 25 | 2 |
| Tebuconazole | (1.56-3) | 2 |
| Cyprodinil | (100-200) | 2 |
| Carbendazim | (3.125-4) | 2 |
| Cyazofamid | 200 | 2 |
| *Fusarium solani* f. sp. *pisi* (MP VI) | | |
| BO | (2-6) | 3 |
| B18 | 0.5 | 4 |
| B90 | (0.5-1) | 4 |
| B1 | 2 | 1 |
| B2 | >32 | 1 |
| Pyraclostrobin | (100-200) | 3 |
| Propiconazole | 200 | 3 |
| Captan | (3-3.125) | 2 |
| Mancozeb | 100 | 2 |
| Pyrimethanil | (200-400) | 3 |
| Fentin Chloride | (0.78-3.12) | 3 |
| Maneb | 25 | 2 |
| Zineb | (6.25-12.5) | 2 |
| Chlorothalonil | (12.5-25) | 2 |
| Metam Sodium | (25-50) | 2 |
| *Fusarium oxysporum* ST33 | | |
| BO | (1-2) | 2 |
| B18 | 0.5 | 2 |
| B90 | (0.25-0.5) | 2 |
| B1 | 1 | 1 |
| B2 | >32 | 1 |
| Captan | (1-2) | 2 |
| Mancozeb | (32-80) | 2 |
| Pyrimethanil | 200 | 2 |
| Thiabendazole | (25-80) | 2 |
| *Fusarium oxysporum* f. sp. *lycopersici* | | |
| BO | (1-2) | 2 |
| B18 | 0.25 | 2 |
| B90 | (0.25-0.5) | 2 |
| B1 | 1 | 1 |
| B2 | >32 | 1 |
| Captan | (1.56-4) | 2 |
| Mancozeb | (6-12.5) | 2 |
| Pyrimethanil | 200 | 2 |
| Thiabendazole | (200-400) | 2 |
| *Stachybotrys chartarum* | | |
| BO | (0.5-2) | 3 |
| B18 | (0.25-1) | 3 |
| B90 | (0.25-0.5) | 3 |

TABLE 1-continued

Range of MIC values (unit in μg/mL) of the individual antifungals and the number of independent (N) triplicate studies*

| Antifungal Compound | Independent MIC (μg/mL) | N |
|---|---|---|
| B1 | 0.5 | 1 |
| B2 | >32 | 1 |
| Fludioxonil | 2 | 2 |
| Pyraclostrobin | (1.56-4) | 2 |
| Propiconazole | (6.25-12.5) | 2 |
| Captan | (0.39-0.5) | 2 |
| Iprodione | (25-30) | 2 |
| Mancozeb | (3.125-6.25) | 2 |
| Fenhexamid | 12.5 | 2 |
| Azoxystrobin | (25-50) | 2 |
| Pyrimethanil | (50-90) | 2 |
| Thiabendazole | (25-30) | 2 |
| *Rhizopus* sp. | | |
| BO | (2-8) | 7 |
| B18 | (0.5-2) | 7 |
| B90 | (1-2) | 2 |
| B1 | 16 | 1 |
| B2 | >32 | 1 |
| Fludioxonil | (50-80) | 2 |
| Propiconazole | (12.5-24) | 3 |
| Captan | (12.5-40) | 3 |
| Iprodione | (3.125-12.5) | 3 |
| Mancozeb | (25-80) | 3 |
| Pyrimethanil | (200-400) | 3 |
| Metalaxyl | 400 | 2 |
| Vinclozolin | 100 | 2 |
| Pyraclostrobin | 50 | 2 |
| Propiconazole | 12.5 | 2 |
| Fentin Chloride | (0.39-0.78) | 2 |
| Maneb | (50-100) | 2 |
| Zineb | 12.5 | 2 |
| Chlorothalonil | 0.78 | 2 |
| Cyproconazole | (12.5-50) | 2 |
| Fluazinam | (0.2-0.78) | 2 |
| Fluopyram | 200 | 2 |
| Mepanipyrim | 50 | 2 |
| Metam Sodium | 100 | 2 |
| Quinoxyfen | (100-200) | 2 |
| Tebuconazole | 0.78 | 2 |
| *Pythium aphanodermatum* | | |
| BO | (4-8) | 3 |
| B18 | (0.25-2) | 3 |
| B90 | (2-4) | 4 |
| Captan | 28 | 3 |
| Mancozeb | (28-50) | 3 |
| Fenhexamid | (0.78-0.80) | 3 |
| Thiophanate-Methyl | 400 | 3 |
| Azoxystrobin | 6.25 | 2 |
| Pyrimethanil | (100-200) | 2 |
| Thiabendazole | (200-400) | 2 |
| *Mucor* sp. | | |
| BO | (0.5-1) | 6 |
| B18 | (0.5-1) | 5 |
| B90 | 0.25 | 2 |
| B1 | 1 | 1 |
| B2 | >32 | 1 |
| Mancozeb | (50-100) | 2 |
| Metam Sodium | 50 | 2 |
| Vinclozolin | (100-200) | 2 |
| Pyraclostrobin | 100 | 2 |
| Propiconazole | 50 | 2 |
| Captan | (3.125-12.5) | 2 |
| Iprodione | (1.56-6.25) | 2 |
| Fenhexamid | 100 | 2 |
| Etridiazole | (200-400) | 2 |
| Thiophanate-methyl | (200-400) | 2 |
| Azoxystrobin | 200 | 2 |
| Pyrimethathanil | 200 | 2 |
| Edifenphos | (50-100) | 2 |
| Fentin Chloride | (1-1.56) | 2 |
| Maneb | (25-50) | 2 |

TABLE 1-continued

Range of MIC values (unit in μg/mL) of the individual antifungals and the number of independent (N) triplicate studies*

| Antifungal Compound | Independent MIC (μg/mL) | N |
|---|---|---|
| Propamocarb | (200-400) | 2 |
| Chlorothalonil | (0.78-1) | 2 |
| Cyproconazole | (100-200) | 2 |
| Dimethomorph | (200-400) | 2 |
| Fluazinam | (0.78-1.0) | 2 |
| Fluopyram | 200 | 2 |
| Tebuconazole | (12.5-15) | 2 |
| Cyprodinil | 50 | 2 |
| Fenoxanil | (50-100) | 2 |
| Bupirimate | 100 | 2 |
| Probenazole | 200 | 2 |
| Fenamidone | (50-200) | 2 |
| Diethofencarb | (100-200) | 2 |
| Iprobenfos | (100-200) | 2 |
| Picoxystrobin | (50-200) | 2 |
| *Magnaporthe grisea* | | |
| BO | (1.56-2) | 5 |
| B18 | (0.39-1.56) | 5 |
| B90 | (1.25-2) | 2 |
| Fludioxonil | (0.16-0.31) | 2 |
| Pyraclostrobin | (0.02-0.025) | 2 |
| Propiconazole | 1.56 | 2 |
| Captan | (0.19-0.2) | 2 |
| Iprodione | 12.5 | 2 |
| Mancozeb | 6.25 | 2 |
| Fenhexamid | 3.125 | 2 |
| Thiophanate-methyl | (25-50) | 2 |
| Pyrimethanil | (100-200) | 2 |
| Thiabendazole | (1.56-3.13) | 2 |
| Edifenphos | 6.25 | 2 |
| Fentin Chlordie | 1.25 | 2 |
| Maneb | 1.56 | 2 |
| Zineb | (0.78-1.56) | 2 |
| Carbendazim | (0.39-0.78) | 2 |
| Bupirimate | 50 | 2 |
| Probenazole | 100 | 2 |
| Iprobenfos | 25 | 2 |
| Picoxystrobin | (3.13-6.25) | 2 |
| Fluxopyroxad | 3.13 | 2 |
| Penthiopyrad | 1.56 | 2 |
| *Phytophthora pini* | | |
| BO | 0.25 | 2 |
| B18 | 0.125 | 2 |
| Fludioxonil | 200 | 1 |
| Pyraclostrobin | 1.56 | 1 |
| Propiconazole | 6.25 | 1 |
| Captan | 0.39 | 1 |
| Mancozeb | 0.39 | 1 |
| Fenhexamid | 50 | 1 |
| Etridiazole | 200 | 1 |
| Thiophanate-Methyl | 25 | 1 |
| Azoxystrobin | 100 | 1 |
| Pyrimethanil | 100 | 1 |
| Thiabendazole | 100 | 1 |
| Edifenphos | 100 | 1 |
| Fentin Chloride | 0.098 | 1 |
| Maneb | 3.125 | 1 |
| Zineb | 25 | 1 |
| Fluazinam | 3.125 | 1 |
| Metam Sodium | 50 | 1 |
| Kasugamycin | 200 | 1 |
| Bupirimate | 50 | 1 |
| Probenazole | 200 | 1 |
| Ethirimol | 200 | 1 |
| *Rhizoctonia solani* | | |
| BO | (6.25-12.5) | 5 |
| B18 | (1.56-8) | 3 |
| B90 | (1.56-8) | 5 |
| Zineb | 3.125 | 2 |
| Chlorothalonil | 1.56 | 2 |
| Tebuconazole | (3.125-6.25) | 2 |

TABLE 1-continued

Range of MIC values (unit in μg/mL) of the individual antifungals and the number of independent (N) triplicate studies*

| Antifungal Compound | Independent MIC (μg/mL) | N |
|---|---|---|
| Cyproconazole | (6.25-12.5) | 2 |
| Fluazinam | (6.25-25) | 2 |
| Fentin Chloride | (12.5-25) | 2 |
| Maneb | (50-100) | 2 |
| Metam Sodium | (25-50) | 2 |
| Iprobenfos | (200-400) | 2 |
| Edifenphos | (200-400) | 2 |
| Cyazofamid | (50-100) | 2 |
| *Penicillium chrysogenum* | | |
| BO | 3.125 | 3 |
| B18 | (0.19-0.38) | 5 |
| B90 | (0.19-0.39) | 5 |
| Fludioxonil | (0.012-0.048) | 2 |
| Pyraclostrobin | (0.1-0.4) | 2 |
| Propiconazole | (6.25-12.5) | 2 |
| Captan | (0.75-0.78) | 2 |
| Mancozeb | (6.25-12.5) | 2 |
| Thiophanate-methyl | 12.5 | 2 |
| Azoxystrobin | (0.39-1.5) | 2 |
| Thiabendazole | (0.375-0.39) | 2 |
| Fentin Chloride | (0.1-0.2) | 2 |
| Maneb | 25 | 2 |
| Zineb | (1.56-6.25) | 2 |
| Chlorothalonil | 0.1 | 2 |
| Cyproconazole | 100 | 2 |
| Fluopyram | (0.1-0.4) | 2 |
| Mepanipyrim | (0.025-0.048) | 2 |
| Metam Sodium | 50 | 2 |
| Cyprodinil | (0.025-0.048) | 2 |
| *Colletotrichum orbiculare* | | |
| BO | 1.56 | 2 |
| B18 | 0.78 | 6 |
| B90 | (0.78-1.56) | 6 |
| Fludioxonil | (0.195-0.39) | 2 |
| Pyraclostrobin | 3.125 | 3 |
| Propiconazole | 3.125 | 2 |
| Captan | (0.39-0.78) | 2 |
| Mancozeb | (6.25-12.5) | 2 |
| Fenhexamid | (100-200) | 3 |
| Fentin Chloride | 1.56 | 2 |
| Maneb | (3.13-6.25) | 2 |
| Zineb | (3.13-6.25) | 2 |
| Chlorothalonil | 0.39 | 2 |
| Cyproconazole | (6.25-12.5) | 2 |
| Metam sodium | (12.5-25) | 2 |
| Tebuconazole | (1.56-3.13) | 2 |
| Cyprodinil | (100-200) | 3 |
| Iprobenfos | (12.5-25) | 2 |
| Penthiopyrad | (50-100) | 2 |
| Quintozene | (25-50) | 2 |
| Cyazofamid | (50-100) | 2 |

*Parenthesized numbers reflect differences between independent triplicate studies, whereas single, unparenthesized numbers indicate the same value was obtained in each study.

The synergistic FICI values are tabulated in Table 2. The FICI values were determined based on growth inhibition after 72 hours. For *Botrytis cinerea* 10-1728, the FICI results determined after 72 hours are similar to those determined after 7 days (similar synergism/antagonism/indifference results). Several significant synergistic combinations have been identified.

These synergistic combinations are beneficial in at least three ways: 1) lowering the dosage of each active ingredient (hence reducing the cost and lowering the off-target toxicity of the active ingredient), 2) increasing the efficacy to inhibit/retard fungal/pathogen growth, and 3) slowing the development of drug resistance in the pathogens [Chou, *Pharmacol. Rev.* 58:621-681 (2006)]. Combination therapy (using multiple active ingredients with different modes of action) is a highly effective way of slowing down drug resistance development.

The present invention shows that benzoxaboroles form synergistic combinations with many antifungals, particularly with antifungal compounds of Fungicide Resistance Action Committee (FRAC) fungicide classes: B1, B3, C3, C4, C6, D1, E1, E2, E3, G1, H5, M4 and M5 [Fungicide Resistance Action Committee (FRAC); FRAC Code List 2015: Fungicides sorted by mode of action. (2015). See, frac.info/publications/] that have been identified as having high risk of resistance development in plant pathogens.

Under the growth conditions used here (PDB or PDA), the dimorphic fungi *Candida albicans* and *Aureobasidium pullulans* species grew primarily in the yeast phase with little to no sign of hyphal/filament development. Interestingly, under such conditions (primarily the yeast phase and lack of hyphal/filamentous/mold phase) the combination treatment (benzoxaborole and another anti-fungal) only yielded one significant synergistic combination and the majority of the combinations tested yielded FICI >0.7 (Table 2). Under those same growth conditions however, all the other organisms tested were filamentous in nature and formed extensive hyphal/mycelial mass.

Synergistic combinations (FICI ≤0.7, and more preferably FICI ≤0.5) were found when benzoxaboroles were combined with non-benzoxaborole antifungals with very specific modes of action. It is noted that benzoxaboroles do not form a synergistic antifungal mixture with all the antifungal examined, and favorable combinations exist in specific classes of antifungals.

Rock et al., *Science,* 316:1759-1761 (2007) reported that benzoxaboroles act to inhibit leucyl-tRNA synthetase, an enzyme involved in amino acid and protein synthesis. Specificially, benzoxabroles disrupt proper leucyl-tRNA synthetase's function by binding to the editing site of the enzyme, and interferes with the enzyme's ability to deal with errors. The benzoxaboroles have not yet been added to the official FRAC list, but would likely be a member of FRAC group D. When so listed, it is thought that a benzoxaborole would be in a new sub-division of group D, rather than in one of groups D1-D5. There is currently no other inhibitor of leucyl-tRNA synthetase on the FRAC listing. However, if such a compound were to be made, it is preferred that it not be paired with a benzoxaborole. That is, it is preferred that the two anti-fungal agents have different MOAs or target sites.

Against most tested organisms (except for *Candida albicans* and *Aureobasidium pullulans*), the benzoxaboroles commonly form effective synergistic combinations (Table 2) with many antifungals that target the fungal respiration (FRAC mode of action: C), inhibit fungal amino acid and protein synthesis (FRAC mode of action: D), and target a signal transduction pathway (FRAC mode of action: E); [Fungicide Resistance Action Committee (FRAC); FRAC Code List 2015: Fungicides sorted by mode of action. (2015). See, frac.info/publications/].

In many cases against Dothideales, Mucorales, Sordariomycetes, and Pezizomycotina, the mixtures of benzoxaborole with an antifungal that inhibits sterol biosynthesis in membranes (FRAC mode of action: G) were found to be very synergistic. The benzoxaboroles also commonly form a synergistic combination with antifungals (especially thiabendazole and thiophanate-methyl) that target fungal mitosis and cell division (especially FRAC code: B1 and B3) and two compounds with multi-site contact activity (FRAC code: M4 (captan) and M5 (chlorothalonil)).

With a few exceptions, benzoxaboroles do not regularly form synergistic combinations with antifungals with modes of action based on inhibiting nucleic acid synthesis (FRAC mode of action: A) and lipid synthesis and membrane integrity (FRAC mode of action: F). The data of Table 3, hereinafter, show the non-synergistic combinations.

TABLE 2

Synergistic Combination Study Results and Calculated FICI Values

| FRAC Code | Antifungal agent | Boron compound | Fungal pest | FICI value | Pest taxonomy * |
|---|---|---|---|---|---|
| A2 | Bupirimate | B18 | *Botrytis cinerea* 10-1728 | 0.5 | 1 |
| A2 | Ethirimol | BO | *Mycosphaerella zeae-maydis* | 0.3 | 2 |
| A2 | Ethirimol | B90 | *Mycosphaerella zeae-maydis* | 0.63 | 2 |
| B1 | Thiabendazole | B18 | *Aspergillus niger* | 0.5 | 1 |
| B1 | Thiabendazole | BO | *Aspergillus fumigatus* | 0.38 | 1 |
| B1 | Thiabendazole | BO | *Fusarium oxysporum* f. sp. *lycopersici* | 0.38 | 1 |
| B1 | Thiabendazole | B90 | *Fusarium oxysporum* f. sp. *lycopersici* | 0.27 | 1 |
| B1 | Thiabendazole | BO | *Fusarium oxysporium* ST33 | 0.38 | 1 |
| B1 | Thiabendazole | B90 | *Fusarium oxysporium* ST33 | 0.41 | 1 |
| B1 | Thiabendazole | BO | *Sclerotinia homoeocarpa* | 0.26 | 1 |
| B1 | Thiabendazole | B90 | *Sclerotinia homoeocarpa* | 0.11 | 1 |
| B1 | Thiabendazole | BO | *Botrytis cinerea* 10-1728 | 0.65 | 1 |
| B1 | Thiabendazole | B18 | *Botrytis cinerea* 10-1728 | 0.37 | 1 |
| B1 | Thiabendazole | BO | *Mycosphaerella zeae-maydis* | 0.66 | 2 |
| B1 | Thiabendazole | B18 | *Mycosphaerella zeae-maydis* | 0.41 | 2 |
| B1 | Thiophanate-methyl | B90 | *Pythium aphanidermatum* | 0.69 | 3 |
| B1 | Thiophanate-methyl | B18 | *Aspergillus niger* | 0.65 | 4 |
| B1 | Thiophanate-methyl | BO | *Sclerotinia homoeocarpa* | 0.33 | 1 |
| B1 | Thiophanate-methyl | B90 | *Sclerotinia homoeocarpa* | 0.36 | 1 |
| B1 | Thiophanate-methyl | BO | *Botrytis cinerea* 10-1728 | 0.45 | 1 |
| B1 | Thiophanate-methyl | B18 | *Botrytis Cinerea* 10-1728 | 0.6 | 1 |
| B1 | Thiophanate-methyl | BO | *Mucor* sp. | 0.5 | 7 |
| B1 | Thiophanate-methyl | B18 | *Mucor* sp. | 0.5 | 7 |
| B1 | Thiophanate-methyl | B18 | *Magnaporthe grisea* | 0.5 | 6 |
| B1 | Thiophanate-methyl | BO | *Magnaporthe grisea* | 0.63 | 6 |
| B3 | Zoxamide | B90 | *Botrytis cinerea* 10-1728 | 0.53 | 1 |
| C2 | Flutolanil | BO | *Botrytis cinerea* 10-1728 | 0.38 | 1 |
| C2 | Flutolanil | B18 | *Botrytis cinerea* 10-1728 | 0.5 | 1 |
| C2 | Fluopyram | B90 | *Sclerotinia homoeocarpa* | 0.49 | 1 |
| C2 | Fluopyram | BO | *Rhizopus* sp. | 0.25 | 7 |
| C2 | Boscalid | B18 | *Sclerotinia homoeocarpa* | 0.63 | 1 |
| C2 | Boscalid | B90 | *Botrytis cinerea* 10-1728 | 0.56 | 1 |
| C2 | Penthiopyrad | BO | *Aspergillus flavus* | 0.31 | 4 |
| C2 | Penthiopyrad | B18 | *Aspergillus flavus* | 0.38 | 4 |
| C2 | Penthiopyrad | B90 | *Aspergillus flavus* | 0.63 | 4 |
| C2 | Penthiopyrad | B18 | *Colletotrichum orbiculare* | 0.63 | 6 |
| C2 | Penthiopyrad | B90 | *Colletotrichum orbiculare* | 0.56 | 6 |
| C2 | Penthiopyrad | BO | *Magnaporthe grisea* | 0.56 | 6 |
| C3 | Azoxystrobin | BO | *Pythium aphanidermatum* | 0.38 | 3 |
| C3 | Azoxystrobin | B90 | *Pythium aphanidermatum* | 0.38 | 3 |
| C3 | Azoxystrobin | B18 | *Pythium aphanidermatum* | 0.5 | 3 |
| C3 | Azoxystrobin | B18 | *Aspergillus fumigatus* | 0.5 | 4 |
| C3 | Azoxystrobin | B90 | *Aspergillus fumigatus* | 0.38 | 4 |
| C3 | Azoxystrobin | BO | *Stachybotrys chartarum* | 0.34 | 6 |
| C3 | Azoxystrobin | B18 | *Stachybotrys chartarum* | 0.14 | 6 |
| C3 | Azoxystrobin | B18 | *Botrytis cinerea* 10-1728 | 0.48 | 1 |
| C3 | Azoxystrobin | B90 | *Botrytis cinerea* 10-1728 | 0.5 | 1 |
| C3 | Azoxystrobin | BO | *Botrytis cinerea* B17 (7 Days) | 0.25 | 1 |
| C3 | Azoxystrobin | B90 | *Botrytis cinerea* B17 (7 Days) | 0.25 | 1 |
| C3 | Azoxystrobin | BO | *Botrytis cinerea* B17 | 0.13 | 1 |
| C3 | Azoxystrobin | B90 | *Botrytis cinerea* B17 | 0.25 | 1 |
| C3 | Azoxystrobin | BO | *Mycosphaerella zeae-maydis* | 0.55 | 2 |
| C3 | Azoxystrobin | B90 | *Mycosphaerella zeae-maydis* | 0.26 | 2 |
| C3 | Azoxystrobin | B18 | *Mycosphaerella zeae-maydis* | 0.26 | 2 |
| C3 | Pyraclostrobin | BO | *Aspergillus niger* | 0.28 | 4 |
| C3 | Pyraclostrobin | B18 | *Aspergillus niger* | 0.16 | 4 |
| C3 | Pyraclostrobin | BO | *Stachybotrys chartarum* | 0.63 | 6 |
| C3 | Pyraclostrobin | B18 | *Stachybotrys chartarum* | 0.15 | 6 |
| C3 | Pyraclostrobin | BO | *Sclerotinia homoeocarpa* | 0.35 | 1 |
| C3 | Pyraclostrobin | B90 | *Sclerotinia homoeocarpa* | 0.36 | 1 |

TABLE 2-continued

Synergistic Combination Study Results and Calculated FICI Values

| FRAC Code | Antifungal agent | Boron compound | Fungal pest | FICI value | Pest taxonomy * |
|---|---|---|---|---|---|
| C3 | Pyraclostrobin | BO | *Botrytis cinerea* 10-1728 | 0.7 | 1 |
| C3 | Pyraclostrobin | BO | *Botrytis cinerea* B17 (7 Days) | 0.18 | 1 |
| C3 | Pyraclostrobin | B90 | *Botrytis cinerea* B17 (7 Days) | 0.18 | 1 |
| C3 | Pyraclostrobin | BO | *Botrytis cinerea* B17 | 0.2 | 1 |
| C3 | Pyraclostrobin | B90 | *Botrytis cinerea* B17 | 0.1 | 1 |
| C3 | Pyraclostrobin | BO | *Mycosphaerella zeae-maydis* | 0.3 | 2 |
| C3 | Pyraclostrobin | B18 | *Mycosphaerella zeae-maydis* | 0.26 | 2 |
| C3 | Pyraclostrobin | B90 | *Mycosphaerella zeae-maydis* | 0.28 | 2 |
| C3 | Pyraclostrobin | BO | *Alternaria solani* | 0.31 | 2 |
| C3 | Pyraclostrobin | B18 | *Alternaria solani* | 0.63 | 2 |
| C3 | Pyraclostrobin | B18 | *Colletotrichum orbiculare* | 0.31 | 6 |
| C3 | Pyraclostrobin | B90 | *Colletotrichum orbiculare* | 0.56 | 6 |
| C3 | Pyraclostrobin | B90 | *Penicillium chrysogenum* | 0.56 | 4 |
| C3 | Pyraclostrobin | B18 | *Penicillium chrysogenum* | 0.58 | 4 |
| C3 | Pyraclostrobin | B18 | *Magnaporthe grisea* | 0.52 | 6 |
| C3 | Pyraclostrobin | BO | *Magnaporthe grisea* | 0.26 | 6 |
| C3 | Fenamidone | BO | *Sclerotinia homoeocarpa* | 0.16 | 1 |
| C3 | Fenamidone | B90 | *Sclerotinia homoeocarpa* | 0.63 | 1 |
| C3 | Fenamidone | B18 | *Botrytis cinerea* 10-1728 | 0.5 | 1 |
| C3 | Fenamidone | B18 | *Mycosphaerella zeae-maydis* | 0.56 | 2 |
| C3 | Fenamidone | B18 | *Alternaria solani* | 0.31 | 2 |
| C3 | Fenamidone | B90 | *Alternaria solani* | 0.31 | 2 |
| C3 | Picoxystrobin | B18 | *Aspergillus fumigatus* | 0.38 | 1 |
| C3 | Picoxystrobin | B90 | *Aspergillus fumigatus* | 0.5 | 1 |
| C3 | Picoxystrobin | B18 | *Magnaporthe grisea* | 0.56 | 6 |
| C4 | Cyazofamid | B90 | *Botrytis cinerea* 10-1728 | 0.63 | 1 |
| C4 | Cyazofamid | BO | *Rhizoctonia solani* | 0.25 | 8 |
| C4 | Cyazofamid | B18 | *Rhizoctonia solani* | 0.19 | 8 |
| C4 | Cyazofamid | B90 | *Rhizoctonia solani* | 0.25 | 8 |
| C4 | Cyazofamid | B18 | *Colletotrichum orbiculare* | 0.7 | 6 |
| C4 | Cyazofamid | B90 | *Colletotrichum orbiculare* | 0.63 | 6 |
| C5 | Fluazinam | BO | *Sclerotinia homoeocarpa* | 0.06 | 1 |
| C5 | Fluazinam | B90 | *Sclerotinia homoeocarpa* | 0.5 | 1 |
| C5 | Fluazinam | B18 | *Alternaria solani* | 0.63 | 2 |
| C5 | Fluazinam | B90 | *Alternaria solani* | 0.63 | 2 |
| C6 | Fentin Chloride | B18 | *Aspergillus fumigatus* | 0.63 | 4 |
| C6 | Fentin Chloride | B90 | *Aspergillus fumigatus* | 0.56 | 4 |
| C6 | Fentin Chloride | BO | *Fusarium solani* f. sp *pisi* (MPVI) | 0.62 | 6 |
| C6 | Fentin Chloride | B90 | *Fusarium solani* f. sp *pisi* (MPVI) | 0.31 | 6 |
| C6 | Fentin Chloride | B18 | *Fusarium solani* f. sp *pisi* (MPVI) | 0.14 | 6 |
| C6 | Fentin Chloride | BO | *Sclerotinia homoeocarpa* | 0.38 | 1 |
| C6 | Fentin Chloride | B90 | *Sclerotinia homoeocarpa* | 0.38 | 1 |
| C6 | Fentin Chloride | B18 | *Fusarium verticillioides* | 0.56 | 6 |
| C6 | Fentin Chloride | B90 | *Fusarium verticillioides* | 0.63 | 6 |
| C6 | Fentin Chloride | B90 | *Colletotrichum orbiculare* | 0.56 | 6 |
| C6 | Fentin chloride | BO | *Rhizopus* sp. | 0.56 | 7 |
| D1 | Pyrimethanil | BO | *Rhizopus* sp. | 0.5 | 7 |
| D1 | Pyrimethanil | B90 | *Rhizopus* sp. | 0.7 | 7 |
| D1 | Pyrimethanil | B18 | *Rhizopus* sp. | 0.38 | 7 |
| D1 | Pyrimethanil | BO | *Aspergillus niger* | 0.33 | 4 |
| D1 | Pyrimethanil | B18 | *Aspergillus niger* | 0.31 | 4 |
| D1 | Pyrimethanil | B18 | *Aspergillus fumigatus* | 0.5 | 4 |
| D1 | Pyrimethanil | BO | *Aspergillus flavus* | 0.35 | 4 |
| D1 | Pyrimethanil | B18 | *Aspergillus flavus* | 0.15 | 4 |
| D1 | Pyrimethanil | B18 | *Stachybotrys chartarum* | 0.33 | 6 |
| D1 | Pyrimethanil | BO | *Sclerotinia homoeocarpa* | 0.18 | 1 |
| D1 | Pyrimethanil | B90 | *Sclerotinia homoeocarpa* | 0.14 | 1 |
| D1 | Pyrimethanil | B18 | *Sclerotinia homoeocarpa* | 0.48 | 1 |
| D1 | Pyrimethanil | B18 | *Sclerotinia homoeocarpa* | 0.05 | 1 |
| D1 | Pyrimethanil | BO | *Botrytis cinerea* 10-1728 | 0.45 | 1 |
| D1 | Pyrimethanil | B18 | *Botrytis cinerea* 10-1728 | 0.29 | 1 |
| D1 | Pyrimethanil | BO | *Botrytis cinerea* B-17(7 Days) | 0.27 | 1 |
| D1 | Pyrimethanil | B90 | *Botrytis cinerea* B-17 (7 Days) | 0.13 | 1 |
| D1 | Pyrimethanil | BO | *Botrytis cinema* B-17 | 0.14 | 1 |
| D1 | Pyrimethanil | B90 | *Botrytis cinerea* B-17 | 0.02 | 1 |
| D1 | Pyrimethanil | BO | *Mycosphaerella zeae-maydis* | 0.34 | 2 |
| D1 | Pyrimethanil | B18 | *Mycosphaerella zeae-maydis* | 0.34 | 2 |
| D1 | Pyrimethanil | B90 | *Alternaria solani* | 0.38 | 2 |
| D1 | Mepanipyrim | B18 | *Aspergillus fumigatus* | 0.38 | 4 |
| D1 | Mepanipyrim | B90 | *Aspergillus flavus* | 0.31 | 4 |
| D1 | Mepanipyrim | B18 | *Aspergillus niger* | 0.05 | 4 |
| D1 | Mepanipyrim | B90 | *Aspergillus niger* | 0.09 | 4 |
| D1 | Mepanipyrim | BO | *Botrytis cinerea* 10-1728 | 0.5 | 1 |
| D1 | Mepanipyrim | B18 | *Botrytis cinerea* 10-1728 | 0.5 | 1 |
| D1 | Mepanipyrim | B18 | *Rhizopus* sp. | 0.56 | 7 |

TABLE 2-continued

Synergistic Combination Study Results and Calculated FICI Values

| FRAC Code | Antifungal agent | Boron compound | Fungal pest | FICI value | Pest taxonomy * |
|---|---|---|---|---|---|
| D1 | Mepanipyrim | B90 | *Penicillium chrysogenum* | 0.46 | 4 |
| D1 | Mepanipyrim | B18 | *Penicillium chrysogenum* | 0.66 | 4 |
| D1 | Cyprodinil | BO | *Aspergillus flavus* | 0.63 | 4 |
| D1 | Cyprodinil | B90 | *Aspergillus flavus* | 0.19 | 4 |
| D1 | Cyprodinil | B18 | *Aspergillus niger* | 0.27 | 4 |
| D1 | Cyprodinil | B90 | *Aspergillus niger* | 0.27 | 4 |
| D1 | Cyprodinil | BO | *Sclerotinia homoeocarpa* | 0.13 | 1 |
| D1 | Cyprodinil | B90 | *Sclerotinia homoeocarpa* | 0.13 | 1 |
| D1 | Cyprodinil | BO | *Botrytis cinerea* 10-1728 | 0.5 | 1 |
| D1 | Cyprodinil | B18 | *Botrytis cinerea* 10-1728 | 0.5 | 1 |
| D1 | Cyprodinil | BO | *Mycosphaerella zeae-maydis* | 0.25 | 2 |
| D1 | Cyprodinil | B18 | *Mycosphaerella zeae-maydis* | 0.5 | 2 |
| D1 | Cyprodinil | B18 | *Alternaria solani* | 0.38 | 2 |
| D1 | Cyprodinil | B90 | *Alternaria solani* | 0.19 | 2 |
| D1 | Cyprodinil | B18 | *Colletotrichum orbiculare* | 0.38 | 6 |
| D1 | Cyprodinil | B90 | *Colletotrichum orbiculare* | 0.16 | 6 |
| D3 | Kasugamycin | B18 | *Alternaria solani* | 0.5 | 2 |
| E1 | Quinoxyfen | BO | *Botrytis cinerea* 10-1728 | 0.63 | 1 |
| E1 | Quinoxyfen | B18 | *Botrytis cinerea* 10-1728 | 0.63 | 1 |
| E1 | Quinoxyfen | BO | *Rhizopus* sp. | 0.5 | 7 |
| E2 | Fludioxonil | BO | *Rhizopus* sp. | 0.5 | 7 |
| E2 | Fludioxonil | B90 | *Rhizopus* sp. | 0.7 | 7 |
| E2 | Fludioxonil | B18 | *Aspergillus fumigatus* | 0.63 | 4 |
| E2 | Fludioxonil | B90 | *Aspergillus fumigatus* | 0.38 | 4 |
| E2 | Fludioxonil | B18 | *Stachybotrys chartarum* | 0.48 | 6 |
| E2 | Fludioxonil | BO | *Sclerotinia homoeocarpa* | 0.4 | 1 |
| E2 | Fludioxonil | B90 | *Sclerotinia homoeocarpa* | 0.24 | 1 |
| E2 | Fludioxonil | B18 | *Sclerotinia homoeocarpa* | 0.5 | 1 |
| E2 | Fludioxonil | B90 | *Botrytis cinerea* B-17 (7 Days) | 0.63 | 1 |
| E2 | Fludioxonil | B18 | *Mycosphaerella zeae-maydis* | 0.26 | 2 |
| E2 | Fludioxonil | B90 | *Penicillium chrysogenum* | 0.24 | 4 |
| E2 | Fludioxonil | B18 | *Penicillium chrysogenum* | 0.45 | 4 |
| E2 | Fludioxonil | B18 | *Magnaporthe grisea* | 0.48 | 6 |
| E2 | Fludioxonil | BO | *Magnaporthe grisea* | 0.48 | 6 |
| E3 | Iprodione | BO | *Aspergillus niger* | 0.5 | 4 |
| E3 | Iprodione | B18 | *Aspergillus niger* | 0.5 | 4 |
| E3 | Iprodione | B18 | *Aspergillus fumigatus* | 0.25 | 4 |
| E3 | Iprodione | B18 | *Stachybotrys chartarum* | 0.46 | 6 |
| E3 | Iprodione | BO | *Sclerotinia homoeocarpa* | 0.3 | 1 |
| E3 | Iprodione | B90 | *Sclerotinia homoeocarpa* | 0.48 | 1 |
| E3 | Iprodione | BO | *Botrytis cinerea* B-17 (7 Days) | 0.56 | 1 |
| E3 | Iprodione | BO | *Aureobasidium pullulans* | 0.7 | 2 |
| E3 | Iprodione | B90 | *Alternaria solani* | 0.63 | 2 |
| E3 | Vinclozolin | BO | *Aspergillus niger* | 0.5 | 4 |
| E3 | Vinclozolin | B18 | *Aspergillus niger* | 0.5 | 4 |
| E3 | Vinclozolin | BO | *Aspergillus fumigatus* | 0.15 | 4 |
| E3 | Vinclozolin | BO | *Botrytis cinerea* 10-1728 | 0.65 | 1 |
| E3 | Vinclozolin | B18 | *Botrytis cinerea* 10-1728 | 0.38 | 1 |
| E3 | Vinclozolin | B18 | *Mycosphaerella zeae-maydis* | 0.27 | 2 |
| E3 | Vinclozolin | BO | *Rhizopus* sp. | 0.19 | 7 |
| E3 | Vinclozolin | B18 | *Rhizopus* sp. | 0.5 | 7 |
| E3 | Vinclozolin | BO | *Mucor* sp. | 0.5 | 7 |
| F2 | Edifenphos | B90 | *Sclerotinia homoeocarpa* | 0.56 | 1 |
| F2 | Edifenphos | B18 | *Fusarium verticillioides* | 0.5 | 6 |
| F2 | Edifenphos | B90 | *Fusarium verticillioides* | 0.38 | 6 |
| F2 | Edifenphos | B90 | *Rhizoctonia solani* | 0.38 | 8 |
| F2 | Iprobenfos | B18 | *Aspergillus niger* | 0.67 | 4 |
| F2 | Iprobenfos | B90 | *Aspergillus niger* | 0.67 | 4 |
| F2 | Iprobenfos | B90 | *Rhizoctonia solani* | 0.38 | 8 |
| F2 | Iprobenfos | B18 | *Magnaporthe grisea* | 0.63 | 6 |
| F4 | propamocarb | B18 | *Altarnaria Solani* | 0.31 | 2 |
| F4 | propamocarb | B90 | *Altarnaria Solani* | 0.31 | 2 |
| G1 | Cyproconazole | BO | *Sclerotinia homoeocarpa* | 0.14 | 1 |
| G1 | Cyproconazole | B90 | *Sclerotinia homoeocarpa* | 0.38 | 1 |
| G1 | Cyproconazole | BO | *Botrytis cinerea* 10-1728 | 0.7 | 1 |
| G1 | Cyproconazole | B18 | *Botrytis cinerea* 10-1728 | 0.7 | 1 |
| G1 | Cyproconazole | B90 | *Candida albicans* | 0.56 | 5 |
| G1 | Cyproconazole | BO | *Rhizopus* sp. | 0.63 | 7 |
| G1 | Cyproconazole | B18 | *Rhizopus* sp. | 0.28 | 7 |
| G1 | Cyproconazole | BO | *Mucor* sp. | 0.5 | 7 |
| G1 | Cyproconazole | B18 | *Mucor* sp. | 0.5 | 7 |
| G1 | Cyproconazole | BO | *Rhizoctonia solani* | 0.7 | 8 |
| G1 | Cyproconazole | B90 | *Rhizoctonia solani* | 0.19 | 8 |
| G1 | Cyproconazole | B90 | *Colletotrichum orbiculare* | 0.63 | 6 |
| G1 | Propiconazole | BO | *Rhizopus* sp. | 0.67 | 7 |

TABLE 2-continued

Synergistic Combination Study Results and Calculated FICI Values

| FRAC Code | Antifungal agent | Boron compound | Fungal pest | FICI value | Pest taxonomy * |
|---|---|---|---|---|---|
| G1 | Propiconazole | B90 | *Rhizopus* sp. | 0.37 | 7 |
| G1 | Propiconazole | B18 | *Rhizopus* sp. | 0.63 | 7 |
| G1 | Propiconazole | BO | *Mucor* sp. | 0.5 | 7 |
| G1 | Propiconazole | B18 | *Mucor* sp. | 0.5 | 7 |
| G1 | Propiconazole | BO | *Sclerotinia homoeocarpa* | 0.25 | 1 |
| G1 | Propiconazole | B90 | *Sclerotinia homoeocarpa* | 0.3 | 1 |
| G1 | Propiconazole | BO | *Aureobasidium pullulans* | 0.67 | 2 |
| G1 | Propiconazole | B90 | *Alternaria solani* | 0.54 | 2 |
| G1 | Propiconazole | B90 | *Candida albicans* | 0.63 | 5 |
| G1 | Propiconazole | B18 | *Penicillium chrysogenum* | 0.63 | 4 |
| G1 | Tebuconazole | BO | *Sclerotinia homoeocarpa* | 0.63 | 1 |
| G1 | Tebuconazole | B90 | *Sclerotinia homoeocarpa* | 0.16 | 1 |
| G1 | Tebuconazole | BO | *Mycosphaerella zeae-maydis* | 0.5 | 2 |
| G1 | Tebuconazole | B18 | *Mycosphaerella zeae-maydis* | 0.38 | 2 |
| G1 | Tebuconazole | B18 | *Alternaria solani* | 0.31 | 2 |
| G1 | Tebuconazole | B90 | *Alternaria solani* | 0.63 | 2 |
| G1 | Tebuconazole | B18 | *Candida albicans* | 0.63 | 5 |
| G1 | Tebuconazole | BO | *Rhizopus* sp. | 0.5 | 7 |
| G1 | Tebuconazole | B18 | *Rhizopus* sp. | 0.53 | 7 |
| G1 | Tebuconazole | BO | *Mucor* sp. | 0.67 | 7 |
| G1 | Tebuconazole | B18 | *Mucor* sp. | 0.67 | 7 |
| G3 | Fenhexamid | BO | *Sclerotinia homoeocarpa* | 0.22 | 1 |
| G3 | Fenhexamid | B90 | *Sclerotinia homoeocarpa* | 0.28 | 1 |
| G3 | Fenhexamid | B90 | *Colletotrichum orbiculare* | 0.63 | 6 |
| G3 | Fenhexamid | B18 | *Mycosphaerella zeae-maydis* | 0.3 | 2 |
| G3 | Fenhexamid | BO | *Mycosphaerella zeae-maydis* | 0.38 | 2 |
| G3 | Fenhexamid | B90 | *Mycosphaerella zeae-maydis* | 0.38 | 2 |
| G3 | Fenhexamid | B90 | *Alternaria solani* | 0.63 | 2 |
| H5 | Dimethomorph | BO | *Mucor* sp. | 0.5 | 7 |
| H5 | Dimethomorph | B18 | *Mucor* sp. | 0.5 | 7 |
| I2 | Fenoxanil | B90 | *Sclerotinia homoeocarpa* | 0.38 | 1 |
| I2 | Fenoxanil | B90 | *Alternaria solani* | 0.38 | 2 |
| M3 | Maneb | B18 | *Aspergillus fumigatus* | 0.63 | 4 |
| M3 | Maneb | BO | *Botrytis cinerea* 10-1728 | 0.65 | 1 |
| M3 | Maneb | B18 | *Botrytis cinerea* 10-1728 | 0.33 | 1 |
| M3 | Maneb | B90 | *Alternaria solani* | 0.63 | 2 |
| M3 | Maneb | BO | *Rhizoctonia solani* | 0.37 | 8 |
| M3 | Maneb | B90 | *Rhizoctonia solani* | 0.38 | 8 |
| M3 | Maneb | B18 | *Rhizopus* | 0.63 | 7 |
| M5 | Chlorothalonil | BO | *Botrytis cinerea* 10-1728 | 0.7 | 1 |
| M5 | Chlorothalonil | B18 | *Botrytis cinerea* 10-1728 | 0.35 | 1 |
| M5 | Chlorothalonil | BO | *Rhizopus* sp. | 0.50 | 7 |
| M5 | Chlorothalonil | B18 | *Rhizopus* sp. | 0.38 | 7 |
| M5 | Chlorothalonil | BO | *Sclerotinia homoeocarpa* | 0.56 | 1 |
| M5 | Chlorothalonil | B18 | *Sclerotinia homoeocarpa* | 0.56 | 1 |
| M5 | Chlorothalonil | B18 | *Alternaria solani* | 0.69 | 2 |
| M5 | Chlorothalonil | B90 | *Alternaria solani* | 0.69 | 2 |
| M5 | Chlorothalonil | B90 | *Fusarium graminearum* | 0.5 | 6 |
| M5 | Chlorothalonil | B18 | *Fusarium graminearum* | 0.5 | 6 |
| M5 | Chlorothalonil | B18 | *Colletotrichum orbiculare* | 0.5 | 6 |
| M3 | Metam Sodium | B18 | *Aspergillus fumigatus* | 0.63 | 4 |
| M3 | Metam Sodium | B90 | *Fusarium solani* f. sp. *pisi* (MPVI) | 0.63 | 6 |
| M3 | Metam Sodium | BO | *Sclerotinia homoeocarpa* | 0.38 | 1 |
| M3 | Metam Sodium | B18 | *Sclerotinia homoeocarpa* | 0.63 | 1 |
| M3 | Metam Sodium | BO | *Botrytis cinerea* 10-1728 | 0.56 | 1 |
| M3 | Metam Sodium | B18 | *Botrytis cinerea* 10-1728 | 0.56 | 1 |
| M3 | Metam Sodium | B18 | *Candida albicans* | 0.5 | 5 |
| M3 | Metam Sodium | BO | *Rhizoctonia solani* | 0.37 | 8 |
| M3 | Metam Sodium | B90 | *Rhizoctonia solani* | 0.38 | 8 |
| M3 | Metam Sodium | B18 | *Rhizopus* sp. | 0.56 | 7 |
| M3 | Metam Sodium | B18 | *Colletotrichum orbiculare* | 0.38 | 6 |
| M3 | Metam Sodium | B90 | *Colletotrichum orbiculare* | 0.5 | 6 |
| M3 | Zineb | BO | *Fusarium solani* f. sp. *pisi* (MPVI) | 0.56 | 6 |
| M3 | Zineb | B90 | *Fusarium solani* f. sp. *pisi* (MPVI) | 0.56 | 6 |
| M3 | Zineb | BO | *Sclerotinia homoeocarpa* | 0.14 | 1 |
| M3 | Zineb | B90 | *Sclerotinia homoeocarpa* | 0.56 | 1 |
| M3 | Zineb | B18 | *Botrytis cinerea* 10-1728 | 0.58 | 1 |
| M3 | Zineb | B18 | *Alternaria solani* | 0.63 | 2 |
| M3 | Zineb | B90 | *Alternaria solani* | 0.63 | 2 |
| M3 | Zineb | BO | *Rhizopus* sp. | 0.28 | 7 |
| M3 | Zineb | B90 | *Colletotrichum orbiculare* | 0.63 | 6 |
| M4 | Captan | B90 | *Pythium aphanidermatum* | 0.54 | 3 |
| M4 | Captan | B18 | *Pythium aphanidermatum* | 0.51 | 3 |
| M4 | Captan | BO | *Rhizopus* sp. | 0.38 | 7 |
| M4 | Captan | B90 | *Rhizopus* sp. | 0.6 | 7 |

TABLE 2-continued

| Synergistic Combination Study Results and Calculated FICI Values | | | | | |
|---|---|---|---|---|---|
| FRAC Code | Antifungal agent | Boron compound | Fungal pest | FICI value | Pest taxonomy * |
| M4 | Captan | BO | *Mucor* sp. | 0.38 | 7 |
| M4 | Captan | B18 | *Aspergillus fumigatus* | 0.38 | 4 |
| M4 | Captan | B90 | *Aspergillus fumigatus* | 0.63 | 4 |
| M4 | Captan | BO | *Fusarium verticillioides* | 0.6 | 6 |
| M4 | Captan | B90 | *Fusarium graminearum* | 0.63 | 6 |
| M4 | Captan | B90 | *Colletotrichum orbiculare* | 0.62 | 6 |
| M4 | Captan | BO | *Sclerotinia homoeocarpa* | 0.53 | 1 |
| M4 | Captan | B90 | *Sclerotinia homoeocarpa* | 0.3 | 1 |
| M4 | Captan | BO | *Botrytis cinerea* B-17 | 0.7 | 1 |
| M4 | Captan | B90 | *Botrytis cinerea* B-17 | 0.7 | 1 |
| M4 | Captan | BO | *Botrytis cinerea* B-17(7 Days) | 0.1 | 1 |
| M4 | Captan | B90 | *Botrytis cinerea* B-17(7 Days) | 0.1 | 1 |
| M4 | Captan | B18 | *Mycosphaerella zeae-maydis* | 0.38 | 2 |
| M3 | Mancozeb | B90 | *Pythium aphanidermatum* | 0.54 | 3 |
| M3 | Mancozeb | B90 | *Rhizopus* sp. | 0.4 | 7 |
| M3 | Mancozeb | BO | *Aspergillus niger* | 0.55 | 4 |
| M3 | Mancozeb | BO | *Sclerotinia homoeocarpa* | 0.23 | 1 |
| M3 | Mancozeb | B90 | *Sclerotinia homoeocarpa* | 0.3 | 1 |
| M3 | Mancozeb | B90 | *Aureobasidium pullulans* | 0.68 | 2 |
| P2 | Probenazole | B18 | *Botrytis cinerea* 10-1728 | 0.5 | 1 |

* 1 = Ascomycota Pezizomycotina Leotiomycetes; 2 = Ascomycota Pezizomycotina Dothideomycetes; 3 = Oomycota Oomycetes; 4 = Ascomycota Pezizomycotina Eurotiomycetes; 5 = Ascomycota Saccharomycotina Saccharomycetes; 6 = Ascomycota Pezizomycotina Sordariomycetes; 7 = Zygomycota Mucormycotina Mucorales; 8 = Basidiomycota Agaricomycotina Agaricomycetes.

TABLE 3

| Non-Synergistic Combination Study Results for Fungal and Oomycete Pests and Calculated FICI Values | | | | | |
|---|---|---|---|---|---|
| Target Site Code | Antifungal agent | Boron compound | Pest | FICI value | Pest taxonomy* |
| A1 | Metalaxyl | BO | *Aspergillus niger* | 1.3 | 4 |
| A1 | Metalaxyl | B18 | *Aspergillus niger* | 0.88 | 4 |
| A1 | Metalaxyl | BO | *Aspergillus fumigatus* | 0.9 | 4 |
| A1 | Metalaxyl | BO | *Sclerotinia homoeocarpa* | 1.64 | 1 |
| A1 | Metalaxyl | B90 | *Sclerotinia homoeocarpa* | 2.32 | 1 |
| A1 | Metalaxyl | BO | *Botrytis cinerea* B-17 (7 Days) | 1.06 | 1 |
| A1 | Metalaxyl | B90 | *Botrytis cinerea* B-17 (7 Days) | 1.06 | 1 |
| A1 | Metalaxyl | BO | *Botrytis cinerea* B-17 | 1.25 | 1 |
| A1 | Metalaxyl | B90 | *Botrytis cinerea* B-17 | 1.25 | 1 |
| A1 | Metalaxyl | BO | *Botrytis cinerea* 10-1728 | 1.25 | 1 |
| A1 | Metalaxyl | B90 | *Botrytis cinerea* 10-1728 | 1.5 | 1 |
| A1 | Metalaxyl | BO | *Rhizopus* sp. | 1.25 | 7 |
| A1 | Metalaxyl | B18 | *Rhizopus* sp. | 1.25 | 7 |
| A2 | Bupirimate | BO | *Sclerotinia homoeocarpa* | 1 | 1 |
| A2 | Bupirimate | B90 | *Sclerotinia homoeocarpa* | 0.75 | 1 |
| A2 | Bupirimate | BO | *Botrytis cinerea* 10-1728 | 1.5 | 1 |
| A2 | Bupirimate | BO | *Mucor* sp. | 0.75 | 7 |
| A2 | Bupirimate | B18 | *Mucor* sp. | 0.75 | 7 |
| A2 | Bupirimate | B18 | *Magnaporthe grisea* | 1.25 | 6 |
| A2 | Bupirimate | BO | *Magnaporthe grisea* | 2 | 6 |
| A2 | Ethirimol | BO | *Sclerotinia homoeocarpa* | 1.29 | 1 |
| A2 | Ethirimol | B90 | *Sclerotinia homoeocarpa* | 0.75 | 1 |
| A2 | Ethirimol | BO | *Botrytis cinerea* 10-1728 | 0.75 | 1 |
| A2 | Ethirimol | B18 | *Botrytis cinerea* 10-1728 | 0.75 | 1 |
| B1 | Thiabendazole | BO | *Pythium aphanidermatum* | 1.25 | 3 |
| B1 | Thiabendazole | B90 | *Pythium aphanidermatum* | 1.13 | 3 |
| B1 | Thiabendazole | BO | *Aspergillus niger* | 0.92 | 4 |
| B1 | Thiabendazole | B18 | *Aspergillus fumigatus* | 1.03 | 4 |
| B1 | Thiabendazole | B90 | *Aspergillus fumigatus* | 1.02 | 4 |
| B1 | Thiabendazole | BO | *Aspergillus flavus* | 0.85 | 4 |
| B1 | Thiabendazole | B18 | *Aspergillus flavus* | 1.08 | 4 |
| B1 | Thiabendazole | BO | *Fusarium verticillioides* | 1.25 | 6 |
| B1 | Thiabendazole | B90 | *Fusarium verticillioides* | 1.13 | 6 |
| B1 | Thiabendazole | BO | *Stachybotrys chartarum* | 1.33 | 6 |
| B1 | Thiabendazole | B18 | *Stachybotrys chartarum* | 0.92 | 6 |
| B1 | Thiabendazole | BO | *Botrytis cinerea* B-17 (7 Days) | 1.13 | 1 |
| B1 | Thiabendazole | B90 | *Botrytis cinerea* B-17 (7 Days) | 1.13 | 1 |
| B1 | Thiabendazole | BO | *Botrytis cinerea* B-17 | 1.5 | 1 |
| B1 | Thiabendazole | B90 | *Botrytis cinerea* B-17 | 1.5 | 1 |
| B1 | Thiabendazole | BO | *Aureobasidium pullulans* | 1.5 | 2 |

TABLE 3-continued

Non-Synergistic Combination Study Results for Fungal and Oomycete Pests and Calculated FICI Values

| Target Site Code | Antifungal agent | Boron compound | Pest | FICI value | Pest taxonomy* |
|---|---|---|---|---|---|
| B1 | Thiabendazole | B90 | *Aureobasidium pullulans* | 1.35 | 2 |
| B1 | Thiabendazole | B90 | *Penicillium chrysogenum* | 1.28 | 4 |
| B1 | Thiabendazole | B18 | *Penicillium chrysogenum* | 1.28 | 4 |
| B1 | Thiabendazole | B18 | *Magnaporthe grisea* | 1.13 | 6 |
| B1 | Thiabendazole | BO | *Magnaporthe grisea* | 1.5 | 6 |
| B1 | Carbendazim | BO | *Aspergillus flavus* | 1.13 | 4 |
| B1 | Carbendazim | BO | *Sclerotinia homoeocarpa* | 1.31 | 1 |
| B1 | Carbendazim | B90 | *Sclerotinia homoeocarpa* | 1 | 1 |
| B1 | Carbendazim | B18 | *Sclerotinia homoeocarpa* | 1.06 | 1 |
| B1 | Carbendazim | BO | *Mycosphaerella zeae-maydis* | 0.9 | 2 |
| B1 | Carbendazim | B18 | *Fusarium verticillioides* | 1.78 | 6 |
| B1 | Carbendazim | B90 | *Fusarium verticillioides* | 1.39 | 6 |
| B1 | Carbendazim | B18 | *Aspergillus niger* | 1.06 | 4 |
| B1 | Carbendazim | B90 | *Aspergillus niger* | 1.06 | 4 |
| B1 | Carbendazim | B18 | *Magnaporthe grisea* | 1.13 | 6 |
| B1 | Carbendazim | BO | *Magnaporthe grisea* | 1.5 | 6 |
| B1 | Thiophanate-methyl | BO | *Pythium aphanidermatum* | 0.75 | 3 |
| B1 | Thiophanate-methyl | B18 | *Pythium aphanidermatum* | 0.75 | 3 |
| B1 | Thiophanate-methyl | BO | *Aspergillus niger* | 0.86 | 4 |
| B1 | Thiophanate-methyl | BO | *Aspergillus fumigatus* | 0.8 | 4 |
| B1 | Thiophanate-methyl | B18 | *Aspergillus fumigatus* | 1.03 | 4 |
| B1 | Thiophanate-methyl | B90 | *Aspergillus fumigatus* | 1.03 | 4 |
| B1 | Thiophanate-methyl | B90 | *Penicillium chrysogenum* | 1.27 | 4 |
| B1 | Thiophanate-methyl | B18 | *Penicillium chrysogenum* | 1.27 | 4 |
| B1 | Thiophanate-methyl | BO | *Aureobasidium pullulans* | 1.38 | 2 |
| B1 | Thiophanate-methyl | B90 | *Aureobasidium pullulans* | 1.3 | 2 |
| B1 | Thiophanate-methyl | B18 | *Mycosphaerella zeae-maydis* | 1.25 | 2 |
| B2 | Diethofencarb | BO | *Sclerotinia homoeocarpa* | 1 | 1 |
| B2 | Diethofencarb | B90 | *Sclerotinia homoeocarpa* | 0.75 | 1 |
| B2 | Diethofencarb | BO | *Botrytis cinerea* 10-1728 | 2.33 | 1 |
| B2 | Diethofencarb | B18 | *Botrytis cinerea* 10-1728 | 0.92 | 1 |
| B2 | Diethofencarb | B90 | *Botrytis cinerea* 10-1728 | 2.5 | 1 |
| B2 | Diethofencarb | BO | *Mucor* sp. | 1.25 | 7 |
| B2 | Diethofencarb | B18 | *Mucor* sp. | 1.25 | 7 |
| B2 | Zoxamide | B18 | *Botrytis cinerea* 10-1728 | 1.06 | 1 |
| C2 | Fluopyram | B18 | *Aspergillus fumigatus* | 1.5 | 4 |
| C2 | Fluopyram | B90 | *Aspergillus fumigatus* | 1.25 | 4 |
| C2 | Fluopyram | BO | *Aspergillus flavus* | 1 | 4 |
| C2 | Fluopyram | B90 | *Aspergillus flavus* | 0.75 | 4 |
| C2 | Fluopyram | BO | *Sclerotinia homoeocarpa* | 1.21 | 1 |
| C2 | Fluopyram | BO | *Botrytis cinerea* 10-1728 | 0.75 | 1 |
| C2 | Fluopyram | B18 | *Botrytis cinerea* 10-1728 | 0.75 | 1 |
| C2 | Fluopyram | B18 | *Rhizopus* sp. | 0.75 | 7 |
| C2 | Fluopyram | BO | *Mucor* sp. | 0.75 | 7 |
| C2 | Fluopyram | B18 | *Mucor* sp. | 0.75 | 7 |
| C2 | Fluopyram | B90 | *Penicillium chrysogenum* | 1.12 | 4 |
| C2 | Fluopyram | B18 | *Penicillium chrysogenum* | 1.16 | 4 |
| C2 | Fluopyram | B18 | *Aspergillus niger* | 1 | 4 |
| C2 | Fluopyram | B90 | *Aspergillus niger* | 1 | 4 |
| C2 | Boscalid | BO | *Sclerotinia homoeocarpa* | 1 | 1 |
| C2 | Boscalid | B90 | *Aspergillus niger* | 1.2 | 4 |
| C2 | Boscalid | B18 | *Aspergillus nigher* | 1.2 | 4 |
| C2 | Boscalid | B18 | *Botrytis cinerea* 10-1728 | 1.13 | 1 |
| C2 | Fluxapyroxad | B18 | *Aspergillus nigher* | 1.13 | 4 |
| C2 | Fluxapyroxad | B90 | *Aspergillus nigher* | 1.13 | 4 |
| C2 | Fluxapyroxad | B18 | *Botrytis cinerea* 10-1728 | 0.75 | 1 |
| C2 | Fluxapyroxad | B90 | *Botrytis cinerea* 10-1728 | 0.75 | 1 |
| C2 | Fluxapyroxad | B18 | *Magnaporthe grisea* | 1.25 | 6 |
| C2 | Fluxapyroxad | BO | *Magnaporthe grisea* | 2 | 6 |
| C2 | Penthiopyrad | B18 | *Aspergillus nigher* | 1.25 | 4 |
| C2 | Penthiopyrad | B90 | *Aspergillus nigher* | 1.25 | 4 |
| C2 | Penthiopyrad | B18 | *Botrytis cinerea* 10-1728 | 0.92 | 1 |
| C2 | Penthiopyrad | B90 | *Botrytis cinerea* 10-1728 | 0.92 | 1 |

TABLE 3-continued

Non-Synergistic Combination Study Results for Fungal and Oomycete Pests and Calculated FICI Values

| Target Site Code | Antifungal agent | Boron compound | Pest | FICI value | Pest taxonomy* |
|---|---|---|---|---|---|
| C2 | Penthiopyrad | B18 | *Magnaporthe grisea* | 1.5 | 6 |
| C3 | Azoxystrobin | BO | *Botrytis cinerea* 10-1728 | 0.95 | 1 |
| C3 | Azoxystrobin | BO | *Alternaris solani* | 0.75 | 2 |
| C3 | Azoxystrobin | B18 | *Alternaria solani* | 0.75 | 2 |
| C3 | Azoxystrobin | BO | *Mucor* sp. | 0.75 | 7 |
| C3 | Azoxystrobin | B18 | *Mucor* sp. | 0.75 | 7 |
| C3 | Azoxystrobin | B90 | *Penicillium chrysogenum* | 1.12 | 4 |
| C3 | Azoxystrobin | B18 | *Penicillium chrysogenum* | 1.12 | 4 |
| C3 | Pyraclostrobin | BO | *Aspergillus fumigatus* | 1 | 4 |
| C3 | Pyraclostrobin | BO | *Fusarium solani* f. sp. *pisi* (MPVI) | 0.83 | 6 |
| C3 | Pyraclostrobin | B90 | *Fusarium solani* f. sp. *pisi* (MPVI) | 1 | 6 |
| C3 | Pyraclostrobin | B18 | *Botrytis cinerea* 10-1728 | 1.13 | 1 |
| C3 | Pyraclostrobin | BO | *Aureobasidium pullulans* | 1.03 | 2 |
| C3 | Pyraclostrobin | B90 | *Aureobasidium pullulans* | 2.03 | 2 |
| C3 | Pyraclostrobin | BO | *Mucor* sp. | 0.75 | 7 |
| C3 | Pyraclostrobin | B18 | *Mucor* sp. | 0.75 | 7 |
| C3 | Pyraclostrobin | BO | *Rhizopus* sp. | 1 | 7 |
| C3 | Pyraclostrobin | B18 | *Rhizopus* sp. | 1 | 7 |
| C3 | Fenamidone | BO | *Botrytis cinerea* 10-1728 | 0.75 | 1 |
| C3 | Fenamidone | BO | *Mucor* sp. | 2.25 | 7 |
| C3 | Fenamidone | B18 | *Mucor* sp. | 2.25 | 7 |
| C3 | Picoxystrobin | BO | *Botrytis cinerea* 10-1728 | 1 | 1 |
| C3 | Picoxystrobin | B18 | *Botrytis cinerea* 10-1728 | 0.75 | 1 |
| C3 | Picoxystrobin | BO | *Mucor* sp. | 1.13 | 7 |
| C3 | Picoxystrobin | B18 | *Mucor* sp. | 1.13 | 7 |
| C3 | Picoxystrobin | BO | *Magnaporthe grisea* | 0.75 | 6 |
| C4 | Cyazofamid | BO | *Fusarium verticillioides* | 3 | 6 |
| C4 | Cyazofamid | B90 | *Fusarium verticillioides* | 1 | 6 |
| C4 | Cyazofamid | B18 | *Fusarium verticillioides* | 1 | 6 |
| C4 | Cyazofamid | BO | *Sclerotinia homoeocarpa* | 0.75 | 1 |
| C4 | Cyazofamid | B18 | *Sclerotinia homoeocarpa* | 0.75 | 1 |
| C4 | Cyazofamid | B18 | *Botrytis cinerea* 10-1728 | 1.25 | 1 |
| C4 | Cyazofamid | B18 | *Mycosphaerella zeae-maydis* | 1 | 2 |
| C4 | Cyazofamid | BO | *Mycosphaerella zeae-maydis* | 1 | 2 |
| C4 | Cyazofamid | B90 | *Mycosphaerella zeae-maydis* | 1.5 | 2 |
| C4 | Cyazofamid | B18 | *Fusarium graminearum* | 1 | 6 |
| C4 | Cyazofamid | BO | *Fusarium graminearum* | 1 | 6 |
| C4 | Cyazofamid | B90 | *Fusarium graminearum* | 1.5 | 6 |
| C5 | Fluazinam | BO | *Botrytis cinerea* 10-1728 | 1.5 | 1 |
| C5 | Fluazinam | B18 | *Botrytis cinerea* 10-1728 | 1.5 | 1 |
| C5 | Fluazinam | B90 | *Botrytis cinerea* 10-1728 | 2 | 1 |
| C5 | Fluazinam | BO | *Mycosphaerella zeae-maydis* | 1.05 | 2 |
| C5 | Fluazinam | B18 | *Mycosphaerella zeae-maydis* | 0.88 | 2 |
| C5 | Fluazinam | B18 | *Fusarium verticillioides* | 1.25 | 6 |
| C5 | Fluazinam | B90 | *Fusarium verticillioides* | 0.75 | 6 |
| C5 | Fluazinam | BO | *Rhizopus* sp. | 1.25 | 7 |
| C5 | Fluazinam | B18 | *Rhizopus* sp. | 0.75 | 7 |
| C5 | Fluazinam | BO | *Mucor* sp. | 1.28 | 7 |
| C5 | Fluazinam | B18 | *Mucor* sp. | 1.28 | 7 |
| C5 | Fluazinam | B18 | *Aspergillus niger* | 2.5 | 4 |
| C5 | Fluazinam | B90 | *Aspergillus niger* | 1.5 | 4 |
| C5 | Fluazinam | BO | *Rhizoctonia solani* | 4.25 | 8 |
| C5 | Fluazinam | B90 | *Rhizoctonia solani* | 1.06 | 8 |
| C6 | Fentin Chloride | BO | *Aspergillus Flavus* | 2 | 4 |
| C6 | Fentin Chloride | B90 | *Aspergillus Flavus* | 2 | 4 |
| C6 | Fentin Chloride | B18 | *Aspergillus niger* | 1.05 | 4 |
| C6 | Fentin Chloride | B90 | *Aspergillus niger* | 1.03 | 4 |
| C6 | Fentin Chloride | BO | *Botrytis cinerea* 10-1728 | 1 | 1 |
| C6 | Fentin Chloride | B18 | *Botrytis cinerea* 10-1728 | 0.75 | 1 |
| C6 | Fentin Chloride | BO | *Mycosphaerella zeae-maydis* | 1.46 | 2 |
| C6 | Fentin Chloride | B18 | *Mycosphaerella zeae-maydis* | 1.5 | 2 |
| C6 | Fentin Chloride | B18 | *Alternaria solani* | 0.8 | 2 |
| C6 | Fentin Chloride | B90 | *Alternaria solani* | 0.8 | 2 |
| C6 | Fentin Chloride | B18 | *Candida albicans* | 4.5 | 5 |
| C6 | Fentin Chloride | B90 | *Candida albicans* | 2.18 | 5 |
| C6 | Fentin Chloride | B18 | *Rhizopus* sp. | 1.03 | 7 |
| C6 | Fentin Chloride | BO | *Mucor* sp. | 0.9 | 7 |
| C6 | Fentin Chloride | B18 | *Mucor* sp. | 0.9 | 7 |
| C6 | Fentin Chloride | B90 | *Penicillium chrysogenum* | 1.16 | 4 |
| C6 | Fentin Chloride | B18 | *Penicillium chrysogenum* | 1.16 | 4 |
| C6 | Fentin Chloride | BO | *Rhizoctonia solani* | 0.73 | 8 |
| C6 | Fentin Chloride | B90 | *Rhizoctonia solani* | 0.75 | 8 |
| C6 | Fentin Chloride | B18 | *Colletotrichum orbiculare* | 1.25 | 6 |
| C6 | Fentin Chloride | B18 | *Magnaporthe grisea* | 1.03 | 6 |

TABLE 3-continued

Non-Synergistic Combination Study Results for Fungal and Oomycete Pests and Calculated FICI Values

| Target Site Code | Antifungal agent | Boron compound | Pest | FICI value | Pest taxonomy* |
|---|---|---|---|---|---|
| C6 | Fentin Chloride | BO | *Magnaporthe grisea* | 1.13 | 6 |
| D1 | Pyrimethanil | B18 | *Pythium aphanidermatum* | 0.75 | 3 |
| D1 | Pyrimethanil | B90 | *Pythium aphanidermatum* | 1 | 3 |
| D1 | Pyrimethanil | BO | *Aspergillus fumigatus* | 1.02 | 4 |
| D1 | Pyrimethanil | BO | *Fusarium verticillioides* | 1.5 | 6 |
| D1 | Pyrimethanil | B90 | *Fusarium verticillioides* | 1.25 | 6 |
| D1 | Pyrimethanil | BO | *Stachybotrys chartarum* | 1.06 | 6 |
| D1 | Pyrimethanil | BO | *Fusarium oxysporum* f. sp. *lycopersici* | 1.5 | 6 |
| D1 | Pyrimethanil | B90 | *Fusarium oxysporum* f. sp. *lycopersici* | 1.44 | 6 |
| D1 | Pyrimethanil | BO | *Fusarium solani* f. sp *pisi* (MPVI) | 1.25 | 6 |
| D1 | Pyrimethanil | B90 | *Fusarium solani* f. sp *pisi* (MPVI) | 1 | 6 |
| D1 | Pyrimethanil | B18 | *Fusarium solani* f. sp *pisi* (MPVI) | 1.5 | 6 |
| D1 | Pyrimethanil | BO | *Fusarium oxysporium* ST33 | 1.5 | 6 |
| D1 | Pyrimethanil | B90 | *Fusarium oxysporium* ST33 | 1.75 | 6 |
| D1 | Pyrimethanil | BO | *Aureobasidium pullulans* | 1.25 | 2 |
| D1 | Pyrimethanil | B90 | *Aureobasidium pullulans* | 1.1 | 2 |
| D1 | Pyrimethanil | B18 | *Candida albicans* | 1 | 5 |
| D1 | Pyrimethanil | B90 | *Candida albicans* | 0.75 | 5 |
| D1 | Pyrimethanil | BO | *Alternaria solani* | 0.75 | 2 |
| D1 | Pyrimethanil | B18 | *Alternaria solani* | 0.75 | 2 |
| D1 | Pyrimethanil | BO | *Mucor* sp. | 1.5 | 7 |
| D1 | Pyrimethanil | B18 | *Mucor* sp. | 1.5 | 7 |
| D1 | Pyrimethanil | B18 | *Magnaporthe grisea* | 1 | 6 |
| D1 | Pyrimethanil | BO | *Magnaporthe grisea* | 1.25 | 6 |
| D1 | Mepanipyrim | B90 | *Aspergillus fumigatus* | 1.25 | 4 |
| D1 | Mepanipyrim | BO | *Aspergillus flavus* | 1.13 | 4 |
| D1 | Mepanipyrim | BO | *Sclerotinia homoeocarpa* | 1.13 | 1 |
| D1 | Mepanipyrim | B90 | *Sclerotinia homoeocarpa* | 1.5 | 1 |
| D1 | Mepanipyrim | B18 | *Sclerotinia homoeocarpa* | 1.03 | 1 |
| D1 | Mepanipyrim | B18 | *Rhizopus* sp. | 0.75 | 7 |
| D1 | Cyprodinil | B18 | *Candida albicans* | 1 | 5 |
| D1 | Cyprodinil | B90 | *Candida albicans* | 1.5 | 5 |
| D1 | Cyprodinil | BO | *Mucor* sp. | 1.5 | 7 |
| D1 | Cyprodinil | B18 | *Mucor* sp. | 1.5 | 7 |
| D1 | Cyprodinil | B18 | *Fusarium verticillioides* | 2.25 | 6 |
| D1 | Cyprodinil | B90 | *Fusarium verticillioides* | 2.5 | 6 |
| D1 | Cyprodinil | B90 | *Penicillium chrysogenum* | 0.92 | 4 |
| D1 | Cyprodinil | B18 | *Penicillium chrysogenum* | 1.31 | 4 |
| D3 | Kasugamycin | BO | *Sclerotinia homoeocarpa* | 1.5 | 1 |
| D3 | Kasugamycin | B90 | *Sclerotinia homoeocarpa* | 1 | 1 |
| D3 | Kasugamycin | BO | *Botrytis cinerea* 10-1728 | 0.75 | 1 |
| D3 | Kasugamycin | B18 | *Botrytis cinerea* 10-1728 | 0.75 | 1 |
| D3 | Kasugamycin | B90 | *Alternaria solani* | 1 | 2 |
| E1 | Quinoxyfen | B18 | *Rhizopus* sp. | 1.06 | 7 |
| E2 | Fludioxonil | BO | *Stachybotrys chartarum* | 1.25 | 6 |
| E2 | Fludioxonil | BO | *Botrytis cinerea* 10-1728 | 2.4 | 1 |
| E2 | Fludioxonil | B18 | *Botrytis cinerea* 10-1728 | 1.63 | 1 |
| E2 | Fludioxonil | B90 | *Botrytis cinerea* B17 | 1 | 1 |
| E2 | Fludioxonil | BO | *Aureobasidium pullulans* | 1.5 | 2 |
| E2 | Fludioxonil | B90 | *Aureobasidium pullulans* | 2.4 | 2 |
| E2 | Fludioxonil | BO | *Mycosphaerella zeae-maydis* | 1.05 | 2 |
| E2 | Fludioxonil | B18 | *Colletotrichum orbiculare* | 1.5 | 6 |
| E2 | Fludioxonil | B90 | *Colletotrichum orbiculare* | 1.25 | 6 |
| E3 | Iprodione | BO | *Rhizopus* sp. | 2.13 | 7 |
| E3 | Iprodione | B90 | *Rhizopus* sp. | 2.05 | 7 |
| E3 | Iprodione | B18 | *Rhizopus* sp. | 4.5 | 7 |
| E3 | Iprodione | BO | *Mucor* sp. | 0.74 | 7 |
| E3 | Iprodione | B18 | *Mucor* sp. | 0.74 | 7 |
| E3 | Iprodione | BO | *Aspergillus fumigatus* | 0.8 | 4 |
| E3 | Iprodione | B90 | *Aspergillus fumigatus* | 1.25 | 4 |
| E3 | Iprodione | BO | *Stachybotrys chartarum* | 1.33 | 6 |
| E3 | Iprodione | BO | *Botrytis cinerea* 10-1728 | 1.03 | 1 |
| E3 | Iprodione | B18 | *Botrytis cinerea* 10-1728 | 0.81 | 1 |
| E3 | Iprodione | B90 | *Botrytis cinerea* B-17 (7 Days) | 0.88 | 1 |
| E3 | Iprodione | BO | *Botrytis cinerea* B-17 | 1.25 | 1 |
| E3 | Iprodione | B90 | *Botrytis cinerea* B-17 | 2 | 1 |
| E3 | Iprodione | B18 | *Alternaria solani* | 1.25 | 2 |
| E3 | Iprodione | B18 | *Magnaporthe grisea* | 1.28 | 6 |
| E3 | Iprodione | B18 | *Magnaporthe grisea* | 1.28 | 6 |
| E3 | Vinclozolin | B18 | *Aspergillus fumigatus* | 2.25 | 4 |
| E3 | Vinclozolin | B90 | *Aspergillus fumigatus* | 2.5 | 4 |
| E3 | Vinclozolin | B18 | *Mucor* sp. | 1 | 7 |
| E3 | Vinclozolin | BO | *Sclerotinia homoeocarpa* | 0.8 | 1 |
| E3 | Vinclozolin | B90 | *Sclerotinia homoeocarpa* | 0.72 | 1 |

TABLE 3-continued

Non-Synergistic Combination Study Results for Fungal and Oomycete Pests and Calculated FICI Values

| Target Site Code | Antifungal agent | Boron compound | Pest | FICI value | Pest taxonomy* |
|---|---|---|---|---|---|
| E3 | Vinclozolin | BO | *Mycosphaerella zeae-maydis* | 1.08 | 2 |
| F2 | Edifenphos | B18 | *Aspergillus fumigatus* | 1.03 | 4 |
| F2 | Edifenphos | B90 | *Aspergillus fumigatus* | 1.13 | 4 |
| F2 | Edifenphos | BO | *Sclerotinia homoeocarpa* | 2.25 | 1 |
| F2 | Edifenphos | BO | *Botrytis cinerea* 10-1728 | 0.75 | 1 |
| F2 | Edifenphos | B18 | *Botrytis cinerea* 10-1728 | 0.75 | 1 |
| F2 | Edifenphos | B90 | *Botrytis cinerea* 10-1728 | 1.5 | 1 |
| F2 | Edifenphos | BO | *Mycosphaerella zeae-maydis* | 1 | 2 |
| F2 | Edifenphos | B18 | *Mycosphaerella zeae-maydis* | 1 | 2 |
| F2 | Edifenphos | B18 | *Alternaria solani* | 1.5 | 2 |
| F2 | Edifenphos | B90 | *Alternaria solani* | 0.75 | 2 |
| F2 | Edifenphos | BO | *Mucor* sp. | 1 | 7 |
| F2 | Edifenphos | B18 | *Mucor* sp. | 1 | 7 |
| F2 | Edifenphos | BO | *Rhizoctonia solani* | 1 | 8 |
| F2 | Edifenphos | B18 | *Magnaporthe grisea* | 1.03 | 6 |
| F2 | Edifenphos | BO | *Magnaporthe grisea* | 1.13 | 6 |
| F2 | Iprobenfos | BO | *Sclerotinia homoeocarpa* | 1 | 1 |
| F2 | Iprobenfos | B90 | *Sclerotinia homoeocarpa* | 1.5 | 1 |
| F2 | Iprobenfos | BO | *Botrytis cinerea* 10-1728 | 1 | 1 |
| F2 | Iprobenfos | B18 | *Botrytis cinerea* 10-1728 | 0.75 | 1 |
| F2 | Iprobenfos | BO | *Rhizoctonia solani* | 1 | 8 |
| F2 | Iprobenfos | B18 | *Candida albicans* | 0.75 | 5 |
| F2 | Iprobenfos | B90 | *Candida albicans* | 1.25 | 5 |
| F2 | Iprobenfos | BO | *Mucor* sp. | 1.25 | 7 |
| F2 | Iprobenfos | B18 | *Mucor* sp. | 1.25 | 7 |
| F2 | Iprobenfos | B18 | *Colletotrichum orbiculare* | 1.13 | 6 |
| F2 | Iprobenfos | B90 | *Colletotrichum orbiculare* | 1.03 | 6 |
| F2 | Iprobenfos | BO | *Magnaporthe grisea* | 1 | 6 |
| F3 | Etridiazole | BO | *Aureobasidium pullulans* | 0.75 | 2 |
| F3 | Etridiazole | BO | *Mucor* sp. | 1 | 7 |
| F3 | Etridiazole | B18 | *Mucor* sp. | 1 | 7 |
| F3 | Etridiazole | BO | *Botrytis cinerea* 10-1728 | 1.5 | 1 |
| F3 | Etridiazole | B90 | *Botrytis cinerea* 10-1728 | 2 | 1 |
| F3 | Quintozene | B90 | *Botrytis cinerea* 10-1728 | 1.5 | 1 |
| F3 | Quintozene | B18 | *Botrytis cinerea* 10-1728 | 3 | 1 |
| F3 | Quintozene | B18 | *Colletotrichum orbiculare* | 1.13 | 6 |
| F3 | Quintozene | B90 | *Colletotrichum orbiculare* | 2.5 | 6 |
| F4 | propamocarb | BO | *Sclerotinia homoeocarpa* | 0.75 | 1 |
| F4 | propamocarb | B90 | *Sclerotinia homoeocarpa* | 0.75 | 1 |
| F4 | propamocarb | BO | *Botrytis cinerea* 10-1728 | 1.5 | 1 |
| F4 | propamocarb | B18 | *Botrytis cinerea* 10-1728 | 0.75 | 1 |
| F4 | propamocarb | BO | *Mucor* sp. | 2 | 7 |
| F4 | propamocarb | B18 | *Mucor* sp. | 1 | 7 |
| G1 | Cyproconazole | BO | *Aspergillus flavus* | 2.5 | 4 |
| G1 | Cyproconazole | B90 | *Aspergillus flavus* | 1.5 | 4 |
| G1 | Cyproconazole | B18 | *Aspergillus niger* | 1.5 | 4 |
| G1 | Cyproconazole | B90 | *Aspergillus niger* | 1.25 | 4 |
| G1 | Cyproconazole | B18 | *Fusarium verticillioides* | 2.58 | 6 |
| G1 | Cyproconazole | B90 | *Fusarium verticillioides* | 2.06 | 6 |
| G1 | Cyproconazole | BO | *Mycosphaerella zeae-maydis* | 1.17 | 2 |
| G1 | Cyproconazole | B18 | *Mycosphaerella zeae-maydis* | 0.75 | 2 |
| G1 | Cyproconazole | B18 | *Candida albicans* | 0.75 | 5 |
| G1 | Cyproconazole | B90 | *Penicillium chrysogenum* | 1.27 | 4 |
| G1 | Cyproconazole | B18 | *Penicillium chrysogenum* | 1.47 | 4 |
| G1 | Cyproconazole | B18 | *Colletotrichum orbiculare* | 1.5 | 6 |
| G1 | Propiconazole | BO | *Aspergillus niger* | 0.88 | 4 |
| G1 | Propiconazole | B18 | *Aspergillus niger* | 1.45 | 4 |
| G1 | Propiconazole | BO | *Aspergillus fumigatus* | 1.2 | 4 |
| G1 | Propiconazole | B90 | *Aspergillus fumigatus* | 1.06 | 4 |
| G1 | Propiconazole | BO | *Fusarium verticillioides* | 1.63 | 6 |
| G1 | Propiconazole | BO | *Stachybotrys chartarum* | 2.5 | 6 |
| G1 | Propiconazole | B18 | *Stachybotrys chartarum* | 2.04 | 6 |
| G1 | Propiconazole | B90 | *Colletotrichum orbiculare* | 1.25 | 6 |
| G1 | Propiconazole | B18 | *Colletotrichum orbiculare* | 1.5 | 6 |
| G1 | Propiconazole | BO | *Botrytis cinerea* 10-1728 | 2.8 | 1 |
| G1 | Propiconazole | B18 | *Botrytis cinerea* 10-1728 | 1.26 | 1 |
| G1 | Propiconazole | BO | *Botrytis cinerea* B-17 (7 Days) | 1.06 | 1 |
| G1 | Propiconazole | B90 | *Botrytis cinerea* B-17 (7 Days) | 1.31 | 1 |
| G1 | Propiconazole | BO | *Botrytis cinerea* B-17 | 2.25 | 1 |
| G1 | Propiconazole | B90 | *Botrytis cinerea* B-17 | 2.75 | 1 |
| G1 | Propiconazole | BO | *Mycosphaerella zeae-maydis* | 1.17 | 2 |
| G1 | Propiconazole | B18 | *Mycosphaerella zeae-maydis* | 1.17 | 2 |
| G1 | Propiconazole | B18 | *Alternaria solani* | 1.08 | 2 |
| G1 | Propiconazole | B18 | *Candida albicans* | 1 | 5 |

TABLE 3-continued

Non-Synergistic Combination Study Results for Fungal and Oomycete Pests and Calculated FICI Values

| Target Site Code | Antifungal agent | Boron compound | Pest | FICI value | Pest taxonomy* |
|---|---|---|---|---|---|
| G1 | Propiconazole | B90 | *Penicillium chrysogenum* | 1.17 | 4 |
| G1 | Propiconazole | B90 | *Pythium aphanidermatum* | 1.13 | 3 |
| G1 | Propiconazole | B18 | *Pythium aphanidermatum* | 1.26 | 3 |
| G1 | Propiconazole | B18 | *Magnaporthe grisea* | 1.28 | 6 |
| G1 | Propiconazole | BO | *Magnaporthe grisea* | 1.28 | 6 |
| G1 | Tebuconazole | B18 | *Aspergillus fumigatus* | 1.06 | 4 |
| G1 | Tebuconazole | B90 | *Aspergillus fumigatus* | 1.03 | 4 |
| G1 | Tebuconazole | BO | *Aspergillus flavus* | 2 | 4 |
| G1 | Tebuconazole | B90 | *Aspergillus flavus* | 1.5 | 4 |
| G1 | Tebuconazole | B18 | *Aspergillus niger* | 0.75 | 4 |
| G1 | Tebuconazole | B90 | *Aspergillus niger* | 0.75 | 4 |
| G1 | Tebuconazole | B18 | *Fusarium verticillioides* | 1.54 | 6 |
| G1 | Tebuconazole | B90 | *Fusarium verticillioides* | 2.04 | 6 |
| G1 | Tebuconazole | BO | *Botrytis cinerea* 10-1728 | 2 | 1 |
| G1 | Tebuconazole | B18 | *Botrytis cinerea* 10-1728 | 1 | 1 |
| G1 | Tebuconazole | B90 | *Candida albicans* | 1.13 | 5 |
| G1 | Tebuconazole | B18 | *Colletotrichum orbiculare* | 1.5 | 6 |
| G1 | Tebuconazole | B90 | *Colletotrichum orbiculare* | 1 | 6 |
| G1 | Tebuconazole | BO | *Rhizoctonia solani* | 2.25 | 8 |
| G1 | Tebuconazole | B90 | *Rhizoctonia solani* | 1.13 | 8 |
| G3 | Fenhexamid | B18 | *Pythium aphanidermatum* | 1.5 | 3 |
| G3 | Fenhexamid | B90 | *Pythium aphanidermatum* | 0.75 | 3 |
| G3 | Fenhexamid | BO | *Pythium aphanidermatum* | 0.75 | 3 |
| G3 | Fenhexamid | BO | *Aspergillus fumigatus* | 0.9 | 4 |
| G3 | Fenhexamid | B90 | *Aspergillus flavus* | 0.9 | 4 |
| G3 | Fenhexamid | BO | *Stachybotrys chartarum* | 1.5 | 6 |
| G3 | Fenhexamid | B18 | *Colletotrichum orbiculare* | 1.5 | 6 |
| G3 | Fenhexamid | BO | *Botrytis cinerea* 10-1728 | 1 | 1 |
| G3 | Fenhexamid | B18 | *Botrytis cinerea* 10-1728 | 1 | 1 |
| G3 | Fenhexamid | B90 | *Botrytis cinerea* B17 | 0.75 | 1 |
| G3 | Fenhexamid | BO | *Aureobasidium pullulans* | 1.5 | 2 |
| G3 | Fenhexamid | BO | *Mycosphaerella zeae-maydis* | 1.2 | 2 |
| G3 | Fenhexamid | B18 | *Alternaria solani* | 1.25 | 2 |
| G3 | Fenhexamid | BO | *Alternaria solani* | 1 | 2 |
| G3 | Fenhexamid | BO | *Mucor* sp. | 1.5 | 7 |
| G3 | Fenhexamid | B18 | *Mucor* sp. | 1.5 | 7 |
| G3 | Fenhexamid | B18 | *Colletotrichum orbiculare* | 1.5 | 6 |
| G3 | Fenhexamid | B90 | *Colletotrichum orbiculare* | 1.25 | 6 |
| G3 | Fenhexamid | B18 | *Magnaporthe grisea* | 1.03 | 6 |
| G3 | Fenhexamid | BO | *Magnaporthe grisea* | 1.25 | 6 |
| H5 | Dimethomorph | BO | *Botrytis cinerea* 10-1728 | 0.75 | 1 |
| H5 | Dimethomorph | B18 | *Botrytis cinerea* 10-1728 | 0.75 | 1 |
| I2 | Fenoxanil | BO | *Sclerotinia homoeocarpa* | 0.75 | 1 |
| I2 | Fenoxanil | BO | *Botrytis cinerea* 10-1728 | 0.75 | 1 |
| I2 | Fenoxanil | B18 | *Botrytis cinerea* 10-1728 | 0.75 | 1 |
| I2 | Fenoxanil | B18 | *Alternaria solani* | 0.75 | 2 |
| I2 | Fenoxanil | BO | *Alternaria solani* | 2 | 2 |
| I2 | Fenoxanil | BO | *Mucor* sp. | 1.25 | 7 |
| I2 | Fenoxanil | B18 | *Mucor* sp. | 1.25 | 7 |
| M3 | Maneb | B90 | *Aspergillus fumigatus* | 1.13 | 4 |
| M3 | Maneb | BO | *Aspergillus flavus* | 0.75 | 4 |
| M3 | Maneb | B90 | *Aspergillus flavus* | 1 | 4 |
| M3 | Maneb | B18 | *Aspergillus niger* | 1.13 | 4 |
| M3 | Maneb | B90 | *Aspergillus niger* | 2.13 | 4 |
| M3 | Maneb | BO | *Fusarium solani* f. sp. *pisi* (MPVI) | 1.5 | 6 |
| M3 | Maneb | B90 | *Fusarium solani* f. sp. *pisi* (MPVI) | 0.75 | 6 |
| M3 | Maneb | BO | *Fusarium graminearum* | 3 | 6 |
| M3 | Maneb | B90 | *Fusarium graminearum* | 1 | 6 |
| M3 | Maneb | BO | *Sclerotinia homoeocarpa* | 1.06 | 1 |
| M3 | Maneb | B90 | *Sclerotinia homoeocarpa* | 1.03 | 1 |
| M3 | Maneb | BO | *Mycosphaerella zeae-maydis* | 1.46 | 2 |
| M3 | Maneb | B18 | *Mycosphaerella zeae-maydis* | 1.54 | 2 |
| M3 | Maneb | B18 | *Alternaria solani* | 1.25 | 2 |
| M3 | Maneb | B18 | *Candida albicans* | 1.03 | 5 |
| M3 | Maneb | B90 | *Candida albicans* | 1.06 | 5 |
| M3 | Maneb | B18 | *Fusarium verticillioides* | 1.02 | 6 |
| M3 | Maneb | B90 | *Fusarium verticillioides* | 1.03 | 6 |
| M3 | Maneb | BO | *Rhizopus* sp. | 1.0 | 7 |
| M3 | Maneb | BO | *Mucor* sp. | 1.25 | 7 |
| M3 | Maneb | B18 | *Mucor* sp. | 1.25 | 7 |
| M3 | Maneb | B90 | *Penicillium chrysogenum* | 1.27 | 4 |
| M3 | Maneb | B18 | *Penicillium chrysogenum* | 1.27 | 4 |
| M3 | Maneb | B18 | *Colletotrichum orbiculare* | 1.5 | 6 |
| M3 | Maneb | B90 | *Colletotrichum orbiculare* | 2 | 6 |

TABLE 3-continued

Non-Synergistic Combination Study Results for Fungal and Oomycete Pests and Calculated FICI Values

| Target Site Code | Antifungal agent | Boron compound | Pest | FICI value | Pest taxonomy* |
|---|---|---|---|---|---|
| M3 | Maneb | B18 | *Magnaporthe grisea* | 2.5 | 6 |
| M3 | Maneb | BO | *Magnaporthe grisea* | 2.13 | 6 |
| M5 | Chlorothalonil | B18 | *Aspergillus fumigatus* | 1.5 | 4 |
| M5 | Chlorothalonil | B90 | *Aspergillus fumigatus* | 1.25 | 4 |
| M5 | Chlorothalonil | BO | *Aspergillus flavus* | 1.5 | 4 |
| M5 | Chlorothalonil | B90 | *Aspergillus flavus* | 2 | 4 |
| M5 | Chlorothalonil | B18 | *Aspergillus niger* | 1.05 | 4 |
| M5 | Chlorothalonil | B90 | *Aspergillus niger* | 2.05 | 4 |
| M5 | Chlorothalonil | BO | *Fusarium solani* f. sp. *pisi* (MPVI) | 1.25 | 6 |
| M5 | Chlorothalonil | B90 | *Fusarium solani* f. sp. *pisi* (MPVI) | 1.25 | 6 |
| M5 | Chlorothalonil | BO | *Fusarium graminearum* | 0.75 | 6 |
| M5 | Chlorothalonil | B18 | *Fusarium verticillioides* | 1.25 | 6 |
| M5 | Chlorothalonil | B90 | *Fusarium verticillioides* | 1.5 | 6 |
| M5 | Chlorothalonil | BO | *Mycosphaerella zeae-maydis* | 1.3 | 2 |
| M5 | Chlorothalonil | B18 | *Mycosphaerella zeae-maydis* | 1.3 | 2 |
| M5 | Chlorothalonil | B18 | *Candida albicans* | 1 | 5 |
| M5 | Chlorothalonil | B90 | *Candida albicans* | 1.5 | 5 |
| M5 | Chlorothalonil | BO | *Rhizoctonia solani* | 1.25 | 8 |
| M5 | Chlorothalonil | B90 | *Rhizoctonia solani* | 1.25 | 8 |
| M5 | Chlorothalonil | BO | *Mucor* sp. | 1.25 | 7 |
| M5 | Chlorothalonil | B18 | *Mucor* sp. | 1.25 | 7 |
| M5 | Chlorothalonil | B90 | *Colletotrichum orbiculare* | 0.75 | 6 |
| M3 | Metam Sodium | B90 | *Aspergillus fumigatus* | 1.13 | 4 |
| M3 | Metam Sodium | BO | *Aspergillus flavus* | 2 | 4 |
| M3 | Metam Sodium | B90 | *Aspergillus flavus* | 1.5 | 4 |
| M3 | Metam Sodium | B18 | *Aspergillus niger* | 0.75 | 4 |
| M3 | Metam Sodium | B90 | *Aspergillus niger* | 1.5 | 4 |
| M3 | Metam Sodium | BO | *Fusarium solani* f. sp. *pisi* (MPVI) | 2.5 | 6 |
| M3 | Metam Sodium | BO | *Fusarium graminearum* | 2.5 | 6 |
| M3 | Metam Sodium | B90 | *Fusarium graminearum* | 0.75 | 6 |
| M3 | Metam Sodium | B18 | *Fusarium verticillioides* | 1.25 | 6 |
| M3 | Metam Sodium | B90 | *Fusarium verticillioides* | 1.5 | 6 |
| M3 | Metam Sodium | BO | *Mucor* sp. | 1.5 | 7 |
| M3 | Metam Sodium | B90 | *Mucor* sp. | 1.5 | 7 |
| M3 | Metam Sodium | B90 | *Sclerotinia homoeocarpa* | 0.75 | 1 |
| M3 | Metam Sodium | BO | *Mycosphaerella zeae-maydis* | 1.17 | 2 |
| M3 | Metam Sodium | B18 | *Mycosphaerella zeae-maydis* | 1.25 | 2 |
| M3 | Metam Sodium | B18 | *Alternaria solani* | 1.5 | 2 |
| M3 | Metam Sodium | B90 | *Alternaria solani* | 0.71 | 2 |
| M3 | Metam Sodium | B90 | *Candida albicans* | 0.75 | 5 |
| M3 | Metam Sodium | BO | *Rhizopus* sp. | 0.75 | 7 |
| M3 | Metam Sodium | B18 | *Penicillium chrysogenum* | 0.73 | 4 |
| M3 | Metam Sodium | B90 | *Penicillium chrysogenum* | 1.87 | 4 |
| M3 | Zineb | B18 | *Aspergillus fumigatus* | 1 | 4 |
| M3 | Zineb | B90 | *Aspergillus fumigatus* | 0.75 | 4 |
| M3 | Zineb | BO | *Aspergillus flavus* | 3 | 4 |
| M3 | Zineb | B90 | *Aspergillus flavus* | 2 | 4 |
| M3 | Zineb | BO | *Fusarium graminearum* | 2.13 | 6 |
| M3 | Zineb | B90 | *Fusarium graminearum* | 2.06 | 6 |
| M3 | Zineb | B18 | *Fusarium verticillioides* | 2.25 | 6 |
| M3 | Zineb | B90 | *Fusarium verticillioides* | 2.5 | 6 |
| M3 | Zineb | BO | *Botrytis cinerea* 10-1728 | 1.17 | 1 |
| M3 | Zineb | B90 | *Botrytis cinerea* 10-1728 | 2.5 | 1 |
| M3 | Zineb | BO | *Mycosphaerella zeae-maydis* | 1.5 | 2 |
| M3 | Zineb | B18 | *Mycosphaerella zeae-maydis* | 1.5 | 2 |
| M3 | Zineb | B18 | *Candida albicans* | 2 | 5 |
| M3 | Zineb | B90 | *Candida albicans* | 2 | 5 |
| M3 | Zineb | B18 | *Colletotrichum orbiculare* | 0.75 | 6 |
| M3 | Zineb | B18 | *Rhizopus* sp. | 0.75 | 7 |
| M3 | Zineb | BO | *Rhizoctonia solani* | 0.75 | 8 |
| M3 | Zineb | B90 | *Rhizoctonia solani* | 0.75 | 8 |
| M3 | Zineb | B18 | *Magnaporthe grisea* | 1.5 | 6 |
| M3 | Zineb | BO | *Magnaporthe grisea* | 3 | 6 |
| M4 | Captan | BO | *Aspergillus niger* | 0.88 | 4 |
| M4 | Captan | B18 | *Aspergillus niger* | 1.45 | 4 |
| M4 | Captan | BO | *Aspergillus fumigatus* | 1 | 4 |
| M4 | Captan | BO | *Aspergillus flavus* | 2 | 4 |
| M4 | Captan | B18 | *Mucor* sp. | 0.75 | 7 |
| M4 | Captan | B90 | *Fusarium verticillioides* | 0.75 | 6 |
| M4 | Captan | BO | *Stachybotrys chartarum* | 0.75 | 6 |
| M4 | Captan | B18 | *Stachybotrys chartarum* | 0.78 | 6 |
| M4 | Captan | BO | *Fusarium oxysporum* f. sp. *lycopersici* | 0.75 | 6 |
| M4 | Captan | BO | *Fusarium solani* f. sp. *pisi* (MPVI) | 1 | 6 |
| M4 | Captan | B90 | *Fusarium solani* f. sp. *pisi* (MPVI) | 1.17 | 6 |

TABLE 3-continued

Non-Synergistic Combination Study Results for Fungal and Oomycete Pests and Calculated FICI Values

| Target Site Code | Antifungal agent | Boron compound | Pest | FICI value | Pest taxonomy* |
|---|---|---|---|---|---|
| M4 | Captan | BO | *Fusarium oxysporium* ST33 | 1.25 | 6 |
| M4 | Captan | B90 | *Fusarium oxysporium* ST33 | 1.5 | 6 |
| M4 | Captan | BO | *Fusarium graminearum* | 1.13 | 6 |
| M4 | Captan | B18 | *Colletotrichum orbiculare* | 0.75 | 6 |
| M4 | Captan | BO | *Botrytis cinerea* 10-1728 | 0.85 | 1 |
| M4 | Captan | B18 | *Botrytis cinerea* 10-1728 | 1.63 | 1 |
| M4 | Captan | BO | *Aureobasidium pullulans* | 1.58 | 2 |
| M4 | Captan | B90 | *Aureobasidium pullulans* | 1.43 | 2 |
| M4 | Captan | BO | *Mycosphaerella zeae-maydis* | 0.75 | 2 |
| M4 | Captan | B18 | *Alternaria solani* | 1 | 2 |
| M4 | Captan | B90 | *Alternaria solani* | 1 | 2 |
| M4 | Captan | BO | *Magnaporthe grisea* | 1.28 | 6 |
| M4 | Captan | B18 | *Magnaporthe grisea* | 1.28 | 6 |
| M4 | Captan | B18 | *Penicillium chrysogenum* | 1.28 | 4 |
| M4 | Captan | B90 | *Penicillium chrysogenum* | 1.28 | 4 |
| M3 | Mancozeb | B18 | *Pythium aphanidermatum* | 1.11 | 3 |
| M3 | Mancozeb | BO | *Rhizopus* sp. | 1.4 | 7 |
| M3 | Mancozeb | B18 | *Rhizopus* sp. | 1.25 | 7 |
| M3 | Mancozeb | B18 | *Aspergillus niger* | 1.28 | 4 |
| M3 | Mancozeb | BO | *Aspergillus fumigatus* | 1.03 | 4 |
| M3 | Mancozeb | B90 | *Aspergillus fumigatus* | 1.25 | 4 |
| M3 | Mancozeb | B18 | *Penicillium chrysogenum* | 1.17 | 4 |
| M3 | Mancozeb | B90 | *Penicillium chrysogenum* | 1.17 | 4 |
| M3 | Mancozeb | B90 | *Fusarium verticillioides* | 1.5 | 6 |
| M3 | Mancozeb | BO | *Stachybotrys chartarum* | 2.1 | 6 |
| M3 | Mancozeb | B18 | *Stachybotrys chartarum* | 2.04 | 6 |
| M3 | Mancozeb | BO | *Fusarium oxysporum* f. sp. *lycopersici* | 1.03 | 6 |
| M3 | Mancozeb | B90 | *Fusarium oxysporum* f. sp. *lycopersici* | 1.22 | 6 |
| M3 | Mancozeb | BO | *Fusarium solani* f. sp. *pisi* (MPVI) | 1.25 | 6 |
| M3 | Mancozeb | B90 | *Fusarium oxysporium* ST33 | 1.63 | 6 |
| M3 | Mancozeb | BO | *Fusarium graminearum* | 3 | 6 |
| M3 | Mancozeb | B90 | *Fusarium graminearum* | 1 | 6 |
| M3 | Mancozeb | B18 | *Colletotrichum orbiculare* | 1.5 | 6 |
| M3 | Mancozeb | B90 | *Colletotrichum orbiculare* | 1.25 | 6 |
| M3 | Mancozeb | BO | *Botrytis cinerea* 10-1728 | 2.03 | 1 |
| M3 | Mancozeb | B18 | *Botrytis cinerea* 10-1728 | 2.01 | 1 |
| M3 | Mancozeb | BO | *Botrytis cinerea* B-17 (7 Days) | 0.91 | 1 |
| M3 | Mancozeb | B90 | *Botrytis cinerea* B-17 (7 Days) | 1.03 | 1 |
| M3 | Mancozeb | BO | *Botrytis cinerea* B-17 | 1.28 | 1 |
| M3 | Mancozeb | B90 | *Botrytis cinerea* B-17 | 0.89 | 1 |
| M3 | Mancozeb | BO | *Aureobasidium pullulans* | 0.98 | 2 |
| M3 | Mancozeb | B18 | *Alternaria solani* | 0.8 | 2 |
| M3 | Mancozeb | B90 | *Alternaria solani* | 0.8 | 2 |
| M3 | Mancozeb | B18 | *Candida albicans* | 2 | 5 |
| M3 | Mancozeb | B90 | *Candida albicans* | 3 | 5 |
| M3 | Mancozeb | BO | *Mucor* sp. | 1 | 7 |
| M3 | Mancozeb | B90 | *Mucor* sp. | 1 | 7 |
| M3 | Mancozeb | B18 | *Magnaporthe grisea* | 1.28 | 6 |
| M3 | Mancozeb | BO | *Magnaporthe grisea* | 1.28 | 6 |
| P2 | Probenazole | BO | *Sclerotinia homoeocarpa* | 2.5 | 1 |
| P2 | Probenazoie | B90 | *Sclerotinia homoeocarpa* | 1.5 | 1 |
| P2 | Probenazole | BO | *Botrytis cinerea* 10-1728 | 1.5 | 1 |
| P2 | Probenazole | BO | *Mycosphaerella zeae-maydis* | 1.5 | 2 |
| P2 | Probenazole | B18 | *Mycosphaerella zeae-maydis* | 1.25 | 2 |
| P2 | Probenazole | B18 | *Alternaria solani* | 0.75 | 2 |
| P2 | Probenazole | B90 | *Alternaria solani* | 0.75 | 2 |
| P2 | Probenazole | BO | *Mucor* sp. | 1.5 | 7 |
| P2 | Probenazole | B18 | *Mucor* sp. | 1.5 | 7 |
| P2 | Probenazole | BO | *Magnaporthe grisea* | 2 | 6 |
| P2 | Probenazole | B18 | *Magnaporthe grisea* | 1.25 | 6 |

*1 = Ascomycota Pezizomycotina Leotiomycetes; 2 = Ascomycota Pezizomycotina Dothideomycetes; 3 = Oomycota Oomycetes; 4 = Ascomycota Pezizomycotina Eurotiomycetes; 5 = Ascomycota Saccharomycotina Saccharomycetes; 6 = Ascomycota Pezizomycotina Sordariomycetes; 7 = Zygomycota Mucormycotina Mucorales; 8 = Basidiomycota Agaricomycotina Agaricomycetes.

TABLE 4*

Percentage of tested anti-fungal combinations that exhibited synergistic activity.

| FRAC Target Site and Code | Entries studied in Tables 2 and 3 for each FRAC Target Site and Code | Entries exhibiting synergy (IC ≤ 0.7) | % Exhibiting synergy |
|---|---|---|---|
| A | 27 | 3 | 11.11 |
| B | 74 | 23 | 31.08 |
| C | 183 | 80 | 43.72 |
| D | 88 | 46 | 52.27 |
| E | 67 | 35 | 52.24 |
| F | 52 | 10 | 19.23 |
| G | 112 | 41 | 36.61 |
| H | 4 | 2 | 50.00 |
| I | 9 | 2 | 22.22 |
| M | 210 | 62 | 29.52 |
| P | 12 | 1 | 8.33 |
| total | 838 | 305 | 36.40 |

*calculated from the number of cases with IC ≤ 0.7 for each FRAC Target Site and Code divided by the total number of entries (all IC values) for the respective FRAC Target Site × 100%.

TABLE 5*

Percentage of tested anti-fungal combinations that exhibited synergistic activity by FRAC Code

| FRAC Code | Entries studied in Tables 2 and 3 for each FRAC Code | Entries exhibiting synergy (IC ≤ 0.7) | % Exhibiting synergy |
|---|---|---|---|
| B1 | 65 | 22 | 33.8 |
| B3 | 1 | 1 | 100.0 |
| C3 | 72 | 47 | 65.3 |
| C4 | 18 | 6 | 33.3 |
| C6 | 33 | 11 | 33.3 |
| D1 | 82 | 45 | 54.9 |
| E1 | 4 | 3 | 75.0 |
| E2 | 23 | 14 | 60.9 |
| E3 | 40 | 18 | 45 |
| G1 | 85 | 34 | 40.0 |
| H5 | 4 | 2 | 50.0 |
| M4 | 43 | 17 | 39.5 |
| M5 | 31 | 11 | 35.5 |

*calculated from the number of entries with IC ≤ 0.7 for each FRAC Target Site and Code divide by the total number of cases (all IC values) for the respective FRAC Target Site × 100%.

Materials and Methods
Fungal Isolates and Cultures

*Mycosphaerella zeae-maydis, Alternaria solani, Aureobasidium pullulans, Aspergillus flavus, Aspergillus fumigatus, Aspergillus niger, Sclerotinia homoeocarpa, Botrytis cinerea* 10-1728, *Botrytis cinerea* B17, *Botrytis cinerea* B16, *Candida albicans, Fusarium graminearum, Fusarium verticillioides, Fusarium solani* f. sp. *pisi* (MB VI), *Fusarium oxysporum* ST33, *Fusarium oxysporum* f. sp. *lycopersici, Colletotrichum orbiculare, Penicillium chrysogenum, Stachybotrys chartarum, Magnaporthe grisea, Mucor* sp., *Rhizoctonia solani, Rhizopus* sp., *Phytophthora pini,* and *Pythium aphanidermatum* were cultured from either cryogenic storage stock, silica gel storage stock, or lyophilized (with skim milk) stock in the Plant Pathology and Environmental Microbiology Department at The Pennsylvania State University, University Park, Pa., 16802.

Antifungal and Stock Solutions

Bupirimate, edifenphos, fentin chloride, maneb, propamocarb, zineb, iprobenfos, carbendazim, chlorothalonil, cyproconazole, cyprodinil, diethofencarb, dimethomorph, ethirimol, fenamidone, fenoxanil, fluazinam, fluopyram, mepanipyrim, picoxystrobin, probenazole, quinoxyfen, tebuconazole, fludioxonil, boscalid, zoxamide, fluxapyroxad, penthiopyrad, quintozene, cyazofamid, metalaxyl, vinclozolin, pyraclostrobin, propiconazole, captan, ipordione, mancozeb, fenhexamid, etridiazole, thiophanate-methyl, azoxystrobin, and pyrimethanil were obtained from Sigma-Aldrich and used without further modification/purification. Thiabendazole and 2-(hydroxymethyl)benzene boronic acid hemiester (BOXY or BO) were purchased from Alfa Aeser. Metam sodium and flutolanil were obtained from Chem Service. Kasugamycin was purchased from EMO Life Science. 5-Fluoro-1,3-dihydro-2,1-benzoxaborol-1-ol (B90) and 5-chloro-1,3-dihydro-2,1-benzoxaborol-1-ol (B18) were obtained from Enamine. 5-Methyl-1,3-dihydro-2,1-benzoxaborol-1-ol (B1) and 5-Amino-1,3-dihydro-2,1-benzoxaborol-1-ol (B2) were generously provided by Anacor Pharmaceuticals Inc.

Stock solutions (concentrations of between 4000 μg/mL to 10,000 μg/mL; stored at −18° C.) of the above antifungals were prepared in DMSO, except for kasugamycin, which was prepared in sterile distilled water. The stock solutions were further diluted into sterile 25% potato dextrose broth (PDB) so that the diluted solutions could be used for the antifungal susceptibility studies. This way, a typical microdilution study would reach a final ratio of about 0.5-2% v/v of DMSO in 25% PDB. Control studies showed that 2% v/v of DMSO in 25% PDB did not inhibit fungal growth for the species examined.

Inoculum Preparation

Unless specified, most of the organisms were maintained on potato dextrose agar (PDA), and sufficient asexual spores can be isolated from the cultures after 1-2 weeks of incubation at room temperature (22-24° C.) with 12ON/12OFF (12 hours on and 12 hours off) fluorescent light+darklight photoperiod using fluorescent (Philips, F40LW) and black-light (F40T12) bulbs.

*Mycosphaerella zeae-maydis* was maintained on V8 agar (20%-200 mL V8 juice, 2 g $CaCO_3$, 15 g Agar, 800 mL distilled water) to encourage sporulation. *Fusarium verticillioides* and *Fusarium oxysporum* ST33 were maintained on synthetischer nährstoffarmer agar (SNA), and spore suspensions were prepared from those cultures. Spore inocula were prepared in sterile distilled water with 0.1% Tween® 20, and a hemocytometer was used to determine the spore density. Typically, the spore inoculum was prepared fresh prior to each study, and the inoculum was appropriately diluted to a final concentration of $0.4\text{-}1\times10^5$ spores/mL or CFU/mL in each study. The spore suspension can be stored in a refrigerator for one week.

In cases where a sufficient spore suspension could not be readily prepared, inocula were prepared as mycelium smoothies according an established procedure [Büttner et al., (2004) *Plant Breeding.* 123: 158-166]. *Magnaporthe grisea* cultures were maintained on oatmeal agar (OMA). After 2 weeks of growth, four agar blocks (1 inch long and 1 inch wide) were extracted and added to a flask containing 100 mL of autoclaved Complete Media (0.6 g yeast extract, 0.6 g casein hydrolysate, and 1 g sucrose in 100 mL distilled water). After 1-2 weeks of incubation at 22-24° C. in the dark, the mycelium smoothie inoculum was prepared.

*Alternaria solani* cultures were maintained on PDA. After 1 week of growth, four agar blocks (1 inch long and 1 inch wide) were extracted and added to a flask containing 100 mL autoclaved potato dextrose broth (PDB). After 1-2 weeks of incubation at 27° C. with constant agitation (120 rpm), the mycelium smoothie inoculum was prepared. *Rhizoctonia solani* mycelium inocoulum was prepared by the same method.

*Sclerotinia homoeocarpa* cultures were maintained on PDA. After 1 week of growth, four agar blocks (1 inch long and 1 inch wide) were extracted and added to a flask containing 100 mL autoclaved PDB. After 1-2 weeks of incubation at 27° C. with constant agitation (120 rpm), the mycelium smoothie inoculum was prepared.

*Fusarium graminearum* cultures were maintained on carnation leaf water agar (CLA). After 1 week of growth, four agar blocks (1 inch long and 1 inch wide) were extracted and added to a flask containing 100 mL autoclaved 25% PDB. After 1-2 weeks of incubation at 27° C. with constant agitation (120 rpm), the mycelium smoothie inoculum was prepared.

*Pythium aphanodermatum* cultures were maintained on PDA. After 1 week of growth, four agar blocks (1 inch long and 1 inch wide) were extracted and added to a flask containing 100 mL autoclaved 25% PDB. After 1-2 weeks of incubation at 27° C. with constant agitation (120 rpm), the mycelium smoothie inoculum was prepared. Alternatively, *Pythium* zoospores can be obtained by first covering a healthy agar culture of *Pythium* with 2 mM autoclaved sodium phosphate buffer for 2 hours at 10° C. before gently scraping the surface with a cell scraper. The zoospores can be collected by passing the liquid suspension through a filter paper with about 100 micro pore size. *Phytophthora pini* zoospores were collected this way.

Mycelium smoothie inocula were typically prepared fresh prior to the studies or stored at 4° C. for one week. For the antifungal susceptibility assays, the mycelium smoothies were carefully blended and vortexed to achieve a homogenous suspension in sterile distilled water with 0.1% Tween® 20. The inocula were appropriately diluted into 25% PDB so that when 40 μL of the inoculum was added to 160 μL of 25% PDB (final volume=200 mL) the optical density (OD) at 630 nm would be about 0.02-0.04 (value determined before each study) absorbance after correcting for the intrinsic absorbance from the medium and the microtiter plate.

Antifungal Susceptibility Testing, Synergy Testing, and Interpretation

The minimal inhibitory concentrations (MICs) for individual antifungal agents were determined by following a modified broth microdilution protocol CLSI (Clinical and Laboratory Standards Institute) M38-A2 [Clinical and Laboratory Standards Institute (2008) *Reference method for broth dilution antifungal susceptibility testing of filamentous fungi*—$2^{nd}$ edition: approved standard M38-A2, CLSI, Wayne, Pa.] where 25% potato dextrose broth (PDB) was used as the medium. The studies were performed in flat bottom, 96-well microtiter plates (Greiner Bio-One).

Initially, the individual MICs were determined in triplicate in a final volume of 0.2 mL/well with antifungal concentrations of 0-400 μg/mL (12 serial dilutions down from 200 μg/mL [200, 100, 50, 25, 12.5, 6.25, 3.13, 1.56, 0.78, 0.39, 0.20, and 0.098 μg/mL] or 400 μg/mL [400, 200, 100, 50, 25, 12.5, 6.25, 3.13, 1.56, 0.78, 0.39, and 0.20 μg/mL]; control studies with 0 μg/mL of antifungals were performed in parallel for each plate). Plates sealed with clear polyester film (VWR) were incubated at a temperature of about 25° C. The progress of fungal growth was monitored at 48 hours, 72 hours, 7 days, and 15 days. The MICs were determined as the lowest antifungal concentrations that completely inhibited fungal growth (no visible growth) or the concentrations that inhibited fungal growth by greater than 95% (determined as relative absorbance using the Bio-Tek® PowerWave™ HT microplate reader at 530 or 630 nm) relative to the corresponding antifungal-free control. The measurements obtained at 530 nm or 630 nm are identical because fungal growth will significantly increase the turbidity of the solution. In order to establish appropriate comparison between the different fungi, the FICI (thus, the MICs used) determination was done at 72 hours for all cases discussed herein. Examples of similar antifungal susceptibility testing can be seen in the following publications: Silverira et al., (2009) *J. Med. Microbio.* 58: 1607-1610; Arikan et al., (1999) *J. Clin. Microbiol.* 27: 3946-3951.

The MICs of the individual antifungals ($MIC_{Boron}$ and $MIC_A$) and in combination ($MIC_{BA}$) were determined after 72 hours of incubation. $MIC_{Boron}$ is defined as the MIC value BO, B18, B90 or other related benzoxaboroles. $MIC_A$ is defined as the MIC value of every other individual non-benzoxaborole-based antifungal. $MIC_{BA}$ is defined as the MIC value when the benzoxaborole antifungal is combined with another non-benzoxaborole antifungal. The MICs (unless >200 μg/mL or otherwise specified) of each species were determined in at least two independent experiments, each with three replicates. For the combination setup, the two mixed antifungals (benzoxaboroles and other antifungal) were kept at a constant ratio of $MIC_{Boron}$:$MIC_A$ as recommended by the established fixed ratio method [Chou, (2006) *Pharmacol. Rev.* 58:621-681]. The combination studies were performed in triplicate in flat bottom 96-well microtiter plates with a final media volume of 0.2 mL/well.

The antifungal concentration was set so that the highest [benzoxaborole]=100-80% of the $MIC_{Boron}$ value, while the [A]=[benzoxaborole]·($MIC_A$/$MIC_{Boron}$), where A is defined as the other antifungal used in combination with a benzoxaborole. For example, if a benzoxaborole antifungal and antifungal A exhibit individual MIC values of 1 μg/mL and 25 μg/mL, respectively, the ratio of the benzoxaborole:A combination is kept at 1:25 through the synergy study.

A typical study consisted of 9 serial dilutions down from the highest concentration (10 concentrations in total), with each dilution containing one-half of the reagents used in the prior concentration. Repeated determination of the individual MICs ($MIC_{Boron}$ and $MIC_A$) were performed along with each synergism study. In other words, for each synergism study where the $MIC_{BA}$ value was determined, the individual $MIC_{Boron}$ and $MIC_A$ values were re-determined in parallel studies to serve as internal standards. This ensures a fair comparison between the effect of the combination systems (A+B) and the individual effect of A and B alone, while avoiding misinterpretation due to external experimental variables between measurements done on a different date or with different stock solutions (e.g., incubation temperature fluctuations, slight differences in antifungal concentrations, differences in light intensity, differences in inoculum or antifungal stock, differences in media batches, or an inoculum's vitality).

The fractional inhibitory concentration index (FICI) was calculated for each combination using the equation: FICI=($MIC_{Boron\ (in\ the\ presence\ of\ A)}$/$MIC_{Boron\ (alone)}$)+($MIC_{A\ (in\ the\ presence\ of\ benzoxaborole)}$/$MIC_{A\ (alone)}$) [Chou, (2006) *Pharmacol. Rev.* 58:621-681; Barbee et al., (2014) *J. Antimicrob. Chemother* 69:1572-1578]. The FICI or CI (combination index) can be interpreted according to an established scale for synergy [synergism to very strong synergism; Chou, *Pharmacol. Rev.* 58:621-681 (2006)]. A more conservative interpretation of the FICI values is as follows: FICI ≤0.50=synergy; 4>FICI >0.50 (indifference or no interaction); FICI >4 (antagonism) [Johnson et al., (2004) *Antimicrob. Agents Chemother.*, 48:693-715; Odds, (2003) *J. Antimicrob. Chemother.* 52:1].

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

The invention claimed is:

1. An anti-fungal composition for the growth reduction of one or more target fungi whose growth is reduced by an anti-fungal compound having a preselected MOA as described by a FRAC Target Site Code, said composition comprising a diluent medium having dissolved or dispersed therein a synergistic effective amount of a first anti-fungal compound and a second anti-fungal compound, wherein said first anti-fungal compound is a benzoxaborole of Formula I, and said second anti-fungal compound is other than a benzoxaborole and is known to reduce growth of said one or more target species of fungus when utilized as a sole anti-fungal compound at a concentration greater than said synergistic effective amount and has a preselected FRAC Target Site Code selected from the group consisting of B, C, D, E, G, H, and M

I

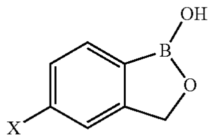

where X is a substituent having a Hammett sigma value for a meta substituent that is greater than about −0.1.

2. The anti-fungal composition according to claim 1, wherein the ratio of the minimum inhibitory concentration (MIC) of one of said anti-fungal agents alone to the concentration of that agent in an anti-fungal composition is greater than about 1.6.

3. The anti-fungal composition according to claim 1, wherein said one or more target fungi to be controlled include one or more members of the phyla of Ascomycota, Oomycota, Basidiomycota and the subphylum Mucoromycotina.

4. An anti-fungal composition for the growth reduction of one or more target fungi of the phyla Ascomycota, Oomycota, Basidiomycota and the subphylum Mucoromycotina whose growth is reducable by an anti-fungal compound having a preselected FRAC Target Site Code, said composition comprising a diluent medium having dissolved or dispersed therein a synergistic effective amount of a first anti-fungal compound and a second anti-fungal compound, wherein said first anti-fungal compound is a benzoxaborole of Formula I, said second anti-fungal compound is other than a benzoxaborole and is known to reduce growth of said one or more target species of fungus when utilized as a sole anti-fungal compound at a concentration greater than said synergistic effective amount and has a preselected FRAC Target Site Code selected from the group consisting of B, C, D, E, G, H, and M

I

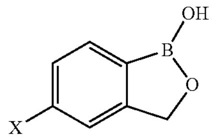

where X is a H, $C_1$-$C_6$ hydrocarbyl, or halo group and wherein the ratio of the minimum inhibitory concentration (MIC) of one of said anti-fungal agents alone to the concentration of that agent in said anti-fungal composition is greater than about 1.6.

5. The anti-fungal composition according to claim 4, wherein said one or more target fungi whose growth to be reduced is of the phylum Ascomycota whose subphylum is selected from the group consisting of Dothideomycetes, Eurotiomycetes, Leotiomycetes and Sordariomycetes.

6. The anti-fungal composition according to claim 4, wherein said one or more target fungi whose growth is to be reduced is selected from one or more of the group of genera consisting of *Aspergillus, Rhizopus, Mucor, Botrytis, Alternaria, Mycosphaerella, Sclerotinia, Rhizoctonia, Colletotrichum, Magnaporthe, Pythium, Phytophthora, Fusarium, Verticillium, Podosphaera, Peronospora, Pseudoperonospora, Golovinomyces, Corynespora, Phakopsora, Cercospora, Didymella, Bipolaris, Puccinia, Bremia, Erysiphe, Albugo, Leviella, Septoria, Uncinula*, and *Phomopsis*.

7. The anti-fungal composition according to claim 4, wherein said preselected FRAC Target Site Code is selected from the group consisting of B1, B3, C3, C4, C6, D1, E1, E2, E3, G1, H5, M4 and M5.

8. The anti-fungal composition according to claim 4, wherein said second antifungal compound is selected from one or more of the group consisting of carbendazim, thiabendazole, thiophanate, thiophanate-methyl, diethofencarb, zoxamide, ethaboxam, pencycuron, flupicolide, flutolanil, fluopyram, fluxapyroxad, penthiopyrad, benodanil, mepronil, isofetamid, fenfuram, carboxin, oxycarboxin, thifluzamide, benzovindiflupyr, bixafen, furametpyr, isopyrazam, penflufen, sedaxane, boscalid, benomyl, fuberidazole, diflumetorim, tolfenpyrad, azoxystrobin, coumoxystrobin, enoxastrobin, flufenoxystrobin, picoxystrobin, pyraoxystrobin, mandestrobin, pyraclostrobin, pyrametostrobin, triclopyricarb, kresoxim-methyl, trifloxystrobin, dimeoxystrobin, fenamistrobin, methominostrobin, orysastrobin, famoxadone, fluoxastrobin, fenamidone, pyribencarb, cyazofamid, amisulbrom, binapacryl, meptyldinocap, dinocap, fluazinam, fentin chloride, fentin acetate, fentin hydroxide, silthiofam, ametoctradin, cyprodinil, mepanipyrim, pyrimethanil, kasugamycin, quinoxyfen, proquinazid, fenpiclonil, fludioxonil, chlozolinate, dimethachlone, iprodione, procymidone, vinclozolin, triforine, pyrifenox, pyrisoxazole, fenarimol, nuarimol, imazalil, oxpoconazole, pefurazoate, prochloraz, triflumizole, azaconazole, bitertanol, bromuconazole, cyproconazole, diniconazole, epoxiconazole, etanconazole, fenbuconazole, fluquinconazole, flusilazole, flutriafol, hexaconazole, imibenconazole, ipconazole, metconazole, myclobutanil, penconazole, propiconazole, simeconazole, tebuconazole, tetraconazole, triadimefon, triadimenol, triticonazole, prothioconazole, aldimorph, dodemorph, fenpropimorph, tridemorph, fenpropidin, piperalin, spiroxamine, fenhexamid, fenpyrazamine, pyributicarb, naftifine, terbinafine, validamycin, polyoxin, dimethomorph, flumorph, pyrimorph, benthiavalicarb, iprovalicarb, valifenalate, mandipropamid, ferbam, macozeb, maneb, metiram, propineb, thiram, zineb, ziram, captan, captafol, folpet, dichlofluanid, tolylfluanid, and chlorothalonil.

9. The anti-fungal composition according to claim 4, wherein said second antifungal compound is selected from one or more of the group consisting of carbendazim, thiabendazole, thiophanate, thiophanate-methyl, zoxamide, ethaboxam, benomyl, fuberidazole, azoxystrobin, coumoxystrobin, enoxastrobin, flufenoxystrobin, picoxystrobin, pyraoxystrobin, mandestrobin, pyraclostrobin, pyrametostrobin, triclopyricarb, kresoxim-methyl, trifloxystrobin, dimeoxystrobin, fenamistrobin, methominostrobin, orysastrobin, famoxadone, fluoxastrobin, fenamidone, pyribencarb, cyazofamid, amisulbrom, fentin chloride, fentin acetate, fentin hydroxide, cyprodinil, mepanipyrim, pyrimethanil, quinoxyfen, proquinazid, fenpiclonil, fludioxonil, chlozolinate, dimethachlone, iprodione, procymidone, vinclozolin, triforine, pyrifenox, pyrisoxazole, fenarimol, nuarimol, imazalil, oxpoconazole, pefurazoate, prochloraz, triflumizole, azaconazole, bitertanol, bromuconazole, cyproconazole, diniconazole, epoxiconazole, etanconazole, fenbuconazole, fluquinconazole, flusilazole, flutriafol, hexaconazole, imibenconazole, ipconazole, metconazole, myclobutanil, penconazole, propiconazole, simeconazole, tebuconazole, tetraconazole, triadimefon, triadimenol, triticonazole, prothioconazole, dimethomorph, flumorph, pyrimorph, benthiavalicarb, iprovalicarb, valifenalate, mandipropamid, captan, captafol, folpet, and chlorothalonil.

10. The anti-fungal composition according to claim 4, wherein the ratio of the MIC of one of said anti-fungal agents alone to the concentration of that agent in said anti-fungal composition is greater than about 2.

11. The anti-fungal composition according to claim 4 that is formulated for topical, soil, foliar or systemic administration.

12. The anti-fungal composition according to claim 4, wherein diluent medium is water-based.

13. The anti-fungal composition according to claim 4, wherein diluent medium is a particulate solid.

14. An anti-fungal concentrate composition that upon dilution provides the anti-fungal composition of claim 1.

15. The anti-fungal concentrate composition according to claim 14, wherein said anti-fungal agents are present dissolved or dispersed in a diluent medium in the same proportion that they are present in the anti-fungal composition.

16. The anti-fungal concentrate composition according to claim 14 that upon dilution with a solvent provides a composition for the growth reduction of one or more target fungi of the phyla Ascomycota, Oomycota, Zygomycota and Basidiomycota that is controllable by an anti-fungal compound having a preselected FRAC Target Site Code, said composition having dissolved or dispersed therein a synergistic effective amount of a first anti-fungal compound and a second anti-fungal compound, wherein said first anti-fungal compound is a benzoxaborole of Formula I, said second anti-fungal compound is other than a benzoxaborole and is known to reduce growth of said one or more target species of fungus when utilized as a sole anti-fungal compound at a concentration greater than said synergistic effective amount and has a preselected FRAC Target Site Code selected from the group consisting of B, C, D, E, G, H, and M

I

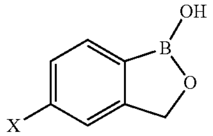

where X is a H, $C_1$-$C_6$ hydrocarbyl or halo group, and wherein the ratio of the minimum inhibitory concentration (MIC) of one of said anti-fungal agents alone to the concentration of that agent in said anti-fungal composition is greater than about 1.6.

17. A method of reducing growth of one or more target fungi whose growth is reducable by an anti-fungal compound having a preselected FRAC Target Site Code, that comprises contacting said one or more target fungi with a synergistic effective amount of a composition comprising a first anti-fungal compound and a second anti-fungal compound, wherein said first anti-fungal compound is a benzoxaborole of Formula I, said second anti-fungal compound is other than a benzoxaborole and is known to reduce growth of said one or more target species of fungus when utilized as a sole anti-fungal compound at a concentration greater than said synergistic effective amount and has a preselected FRAC Target Site Code selected from the group consisting of B, C, D, E, G, H, and M

I

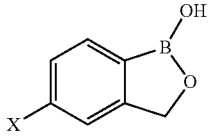

where X is a substituent having a Hammett sigma value for a meta substituent that is greater than about −0.1; and maintaining said contact for a period of time sufficient to inhibit growth of one or more target fungi.

18. The method according to claim 17, wherein said first anti-fungal compound and said second anti-fungal compounds are dissolved or dispersed in a diluent medium when said one or more target fungi is contacted.

19. The method according to claim 17, wherein the ratio of the minimum inhibitory concentration (MIC) of one of said anti-fungal agents alone to the concentration of that agent in an anti-fungal composition is greater than about 1.6.

20. The method according to claim 17, wherein said one or more target fungi whose growth is to be reduced include one or more of a member of the phyla of Ascomycota, Oomycota, Basidiomycota and subphylum Mucoromycotina.

21. The method according to claim 18, wherein said one or more target whose growth is to be reduced is of the phylum Ascomycota whose subphylum is selected from the group consisting of Dothideomycetes, Eurotiomycetes, Leotiomycetes and Sordariomycetes.

22. The method according to claim 18, wherein said one or more target fungi whose growth is to be reduced is selected from one or more of the group of genera consisting of *Aspergillus, Rhizopus, Mucor, Botrytis, Alternaria, Mycosphaerella, Sclerotinia, Rhizoctonia, Colletotrichum, Magnaporthe, Pythium, Phytophthora, Fusarium, Verticillium, Podosphaera, Peronospora, Pseudoperonospora,*

*Golovinomyces, Corynespora, Phakopsora, Cercospora, Didymella, Bipolaris, Puccinia, Bremia, Erysiphe, Albugo, Leviella, Septoria, Uncinula*, and *Phomopsis.*

23. The method according to claim 17, wherein said preselected FRAC Target Site Code is selected from the group consisting of B1, B3, C3, C4, C6, D1, E1, E2, E3, G1, H5, M4 and M5.

24. The method according to claim 17, wherein a benzoxaborole of Formula I is in mixture with a second anti-fungal compound that is selected from one or more of the group consisting of carbendazim, thiabendazole, thiophanate, thiophanate-methyl, diethofencarb, zoxamide, ethaboxam, pencycuron, flupicolide, flutolanil, fluopyram, fluxapyroxad, penthiopyrad, benodanil, mepronil, isofetamid, fenfuram, carboxin, oxycarboxin, thifluzamide, benzovindiflupyr, bixafen, furametpyr, isopyrazam, penflufen, sedaxane, boscalid, benomyl, fuberidazole, diflumetorim, tolfenpyrad, azoxystrobin, coumoxystrobin, enoxastrobin, flufenoxystrobin, picoxystrobin, pyraoxystrobin, mandestrobin, pyraclostrobin, pyrametostrobin, triclopyricarb, kresoxim-methyl, trifloxystrobin, dimeoxystrobin, fenamistrobin, methominostrobin, orysastrobin, famoxadone, fluoxastrobin, fenamidone, pyribencarb, cyazofamid, amisulbrom, binapacryl, meptyldinocap, dinocap, fluazinam, fentin chloride, fentin acetate, fentin hydroxide, silthiofam, ametoctradin, cyprodinil, mepanipyrim, pyrimethanil, kasugamycin, quinoxyfen, proquinazid, fenpiclonil, fludioxonil, chlozolinate, dimethachlone, iprodione, procymidone, vinclozolin, triforine, pyrifenox, pyrisoxazole, fenarimol, nuarimol, imazalil, oxpoconazole, pefurazoate, prochloraz, triflumizole, azaconazole, bitertanol, bromuconazole, cyproconazole, diniconazole, epoxiconazole, etanconazole, fenbuconazole, fluquinconazole, flusilazole, flutriafol, hexaconazole, imibenconazole, ipconazole, metconazole, myclobutanil, penconazole, propiconazole, simeconazole, tebuconazole, tetraconazole, triadimefon, triadimenol, triticonazole, prothioconazole, aldimorph, dodemorph, fenpropimorph, tridemorph, fenpropidin, piperalin, spiroxamine, fenhexamid, fenpyrazamine, pyributicarb, naftifine, terbinafine, validamycin, polyoxin, dimethomorph, flumorph, pyrimorph, benthiavalicarb, iprovalicarb, valifenalate, mandipropamid, ferbam, macozeb, maneb, metiram, propineb, thiram, zineb, ziram, captan, captafol, folpet, dichlofluanid, tolylfluanid, and chlorothalonil.

25. The method according to claim 17, wherein a benzoxaborole of Formula T is in mixture with a second anti-fungal compound that is selected from one or more of the group consisting of carbendazim, thiabendazole, thiophanate, thiophanate-methyl, zoxamide, ethaboxam, benomyl, fuberidazole, azoxystrobin, coumoxystrobin, enoxastrobin, flufenoxystrobin, picoxystrobin, pyraoxystrobin, mandestrobin, pyraclostrobin, pyrametostrobin, triclopyricarb, kresoxim-methyl, trifloxystrobin, dimeoxystrobin, fenamistrobin, methominostrobin, orysastrobin, famoxadone, fluoxastrobin, fenamidone, pyribencarb, cyazofamid, amisulbrom, fentin chloride, fentin acetate, fentin hydroxide, cyprodinil, mepanipyrim, pyrimethanil, quinoxyfen, proquinazid, fenpiclonil, fludioxonil, chlozolinate, dimethachlone, iprodione, procymidone, vinclozolin, triforine, pyrifenox, pyrisoxazole, fenarimol, nuarimol, imazalil, oxpoconazole, pefurazoate, prochloraz, triflumizole, azaconazole, bitertanol, bromuconazole, cyproconazole, diniconazole, epoxiconazole, etanconazole, fenbuconazole, fluquinconazole, flusilazole, flutriafol, hexaconazole, imibenconazole, ipconazole, metconazole, myclobutanil, penconazole, propiconazole, simeconazole, tebuconazole, tetraconazole, triadimefon, triadimenol, triticonazole, prothioconazole, dimethomorph, flumorph, pyrimorph, benthiavalicarb, iprovalicarb, valifenalate, mandipropamid, captan, captafol, folpet, and chlorothalonil.

* * * * *